US012708609B2

(12) United States Patent
Mrsny et al.

(10) Patent No.: US 12,708,609 B2
(45) Date of Patent: *Aug. 18, 2026

(54) METHODS AND COMPOSITIONS FOR TREATING INFLAMMATION

(71) Applicants: UNIVERSITY OF MASSACHUSETTS, Boston, MA (US); UNIVERSITY OF BATH, Bath (GB)

(72) Inventors: Randall Mrsny, Los Altos Hills, CA (US); Beth McCormick, Haverhill, MA (US); Roland Ellwood Dolle, Ashland, MA (US)

(73) Assignees: UNIVERSITY OF BATH, Bath (GB); UNIVERSITY OF MASSACHUSETTS, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/517,596

(22) Filed: Nov. 22, 2023

(65) Prior Publication Data

US 2024/0207212 A1 Jun. 27, 2024

Related U.S. Application Data

(63) Continuation of application No. 16/631,023, filed as application No. PCT/US2018/042116 on Jul. 13, 2018, now Pat. No. 11,865,093.

(60) Provisional application No. 62/532,539, filed on Jul. 14, 2017.

(51) Int. Cl.

| | |
|---|---|
| ***A61K 31/195*** | (2006.01) |
| ***A61K 47/59*** | (2017.01) |
| ***A61K 47/60*** | (2017.01) |
| ***A61K 47/61*** | (2017.01) |

(52) U.S. Cl.

CPC .......... *A61K 31/195* (2013.01); *A61K 47/593* (2017.08); *A61K 47/60* (2017.08); *A61K 47/61* (2017.08)

(58) Field of Classification Search

CPC .... A61K 31/195; A61K 47/593; A61K 47/61; A61K 47/60

See application file for complete search history.

(56) References Cited

U.S. PATENT DOCUMENTS

| | | | | |
|---|---|---|---|---|
| 3,854,480 | A | 12/1974 | Zaffaroni | 424/424 |
| 4,452,775 | A | 6/1984 | Kent | 424/19 |
| 4,675,189 | A | 6/1987 | Kent et al. | 424/490 |
| 5,075,109 | A | 12/1991 | Tice et al. | 424/88 |
| 5,133,974 | A | 7/1992 | Paradissis et al. | 424/480 |
| 5,407,686 | A | 4/1995 | Patel et al. | 424/468 |
| 5,736,152 | A | 4/1998 | Dunn | 424/426 |
| 11,865,093 | B2 * | 1/2024 | Mrsny | A61K 47/60 |
| 2004/0265323 | A1 | 12/2004 | McCormick et al. | 424/184.1 |
| 2006/0073196 | A1 | 4/2006 | Benoit et al. | 424/450 |
| 2010/0029755 | A1 | 2/2010 | Chung et al. | 514/11 |
| 2015/0306123 | A1 | 10/2015 | Li et al. | |
| 2016/0114054 | A1 | 4/2016 | Kuebelbeck et al. | 514/15.4 |

FOREIGN PATENT DOCUMENTS

| | | |
|---|---|---|
| CN | 105062034 | 11/2015 |
| JP | 2003-525243 | 8/2003 |
| JP | 2015-534954 | 12/2015 |
| WO | WO-01/64214 | 9/2001 |
| WO | WO/2002/030915 | 4/2002 |
| WO | WO/2004/009584 | 1/2004 |
| WO | WO/2004/071498 | 8/2004 |
| WO | WO/2005/033101 | 4/2005 |
| WO | WO-2007/136857 A2 | 11/2007 |
| WO | WO/2014/106021 | 7/2014 |
| WO | WO/2015/089268 | 6/2015 |

OTHER PUBLICATIONS

Agbor, T. A. et al. (2011) "The ERM protein, ezrin, regulates neutrophil transmigration by modulating the apical localization of MRP2 in response to the SipA effector protein during *Salmonella typhimurium* infection," *Cellular Microbiology* 13(12), 2007-2021.

Annese, V. et al. (2006) "Multidrug resistance 1 gene in inflammatory bowel disease: a meta-analysis," *World Journal of Gastroenterology* 12(23), 3636-3644.

Anton, R. et al. (1998) "Occurrence of hepoxilins and trioxilins in psoriatic lesions," *Journal of Investigative Dermatology* 110(4), 303-310.

Attali, C. et al. (2008) "The interaction of *Streptococcus pneumoniae* with plasmin mediates transmigration across endothelial and epithelial monolayers by intercellular junction cleavage," *Infection and Immunity* 76(11), 5350-5356.

Baird, B. R. et al. (1986) "O2 metabolites and neutrophil elastase synergistically cause edematous injury in isolated rat lungs," *Journal of Applied Physiology* 61(6), 2224-2229.

Bakos, E. et al. (2000) "Characterization of the amino-terminal regions in the human multidrug resistance protein (MRP1)," *Journal of Cell Science* 113(24), 4451.

(Continued)

*Primary Examiner* — Paul V Ward

(74) *Attorney, Agent, or Firm* — Medlen & Carroll, LLP

(57) ABSTRACT

Disclosed herein are methods and compositions for treating neutrophil-mediated inflammation by targeting, in any combination, the pro-inflammatory MRP2/HXA3 pathway and/or the anti-inflammatory P-gp/endocannabinoid pathway and/or the anti-inflammatory MRP 1/L-AMEND pathway, comprising administering to the subject a therapeutically effective amount of (a) one or more first compound that inhibits the activity and/or level of one or more of multidrug resistance protein 2 (MRP2) and hepoxilin A3 (HXA3) synthase, and/or (b) one or more second compound that increases the level and/or activity of one or more N-acylethanolamines (NAEs), and/or (c) one or more third compound that increases the level and/or activity of multidrug resistance protein 1 (MRP1), wherein the therapeutic amount of the first, second, and third compounds reduces migration of neutrophils into the target tissue.

6 Claims, 28 Drawing Sheets

Specification includes a Sequence Listing.

(56) References Cited

OTHER PUBLICATIONS

Bakos, É et al. (2007) "Portrait of multifaceted transporter, the multidrug resistance-associated protein 1 (MRP1/ABCC1)," *Pflügers Archiv—European Journal of Physiology* 453(5), 621-641.
Bhowmick, R. et al. (2013) "Systemic Disease during *Streptococcus pneumoniae* Acute Lung Infection Requires 12-Lipoxygenase-Dependent Inflammation," *Journal of Immunology* 191(10), 5115.
Blokzijl, H. et al. (2008) "Up-regulation and Cytoprotective Role of Epithelial Multidrug Resistance-associated Protein 1 in Inflammatory Bowel Disease," *Journal of Biological Chemistry* 283(51), 35630-35637.
Boll, E. J. et al. (2012) "Enteroaggregative *Escherichia coli* promotes transepithelial migration of neutrophils through a conserved 12-lipoxygenase pathway," *Cellular Microbiology* 14(1), 120-132.
Branger, J. et al. (2004) "Role of Toll-like receptor 4 in gram-positive and gram-negative pneumonia in mice," *Infection and Immunity* 72(2), 788-794.
Brant, S. R. et al. (2003) "*MDR1* Ala893 Polymorphism is Associated with Inflammatory Bowel Disease," *American Journal of Human Genetics* 73(6), 1282-1292.
Brinar, M. et al. (2013) "MDR1polymorphisms are associated with inflammatory bowel disease in a cohort of Croatian IBD patients," *BMC Gastroenterology* 13(1), 57.
Chiavolini, D. et al. (2008) "Animal Models of *Streptococcus pneumoniae* Disease," *Clinical Microbiology Reviews* 21(4), 666.
Chicca, A. et al. (2012) "Evidence for Bidirectional Endocannabinoid Transport across Cell Membranes," *Journal of Biological Chemistry* 287(41), 34660-34682.
Clark, R. T. et al. (2009) "Bacterial particle endocytosis by epithelial cells is selective and enhanced by tumor necrosis factor receptor ligands," *Clinical and Vaccine Immunology* 16(3), 397-407.
Clarke, Thomas B. et al. (2011) "Invasive Bacterial Pathogens Exploit TLR-Mediated Downregulation of Tight Junction Components to Facilitate Translocation across the Epithelium," *Cell Host & Microbe* 9(5), 404-414.
Dinh, T. P. et al. (2002) "Brain monoglyceride lipase participating in endocannabinoid inactivation," *Proceedings of the National Academy of Sciences* 99(16), 10819.
Doyle, N. A. et al. (1997) "Neutrophil margination, sequestration, and emigration in the lungs of L-selectin-deficient mice," *Journal of Clinical Investigation* 99(3), 526-533.
Eliasson, M. et al. (2010) "*Streptococcus pneumoniae* induces expression of the antibacterial CXC chemokine MIG/CXCL9 via MyD88-dependent signaling in a murine model of airway infection," *Microbes and Infection* 12(7), 565-573.
Englund, G. et al. (2006) "Efflux transporters in ulcerative colitis Decreased expression of BCRP (ABCG2) and Pgp (ABCB1)," *Inflammatory Bowel Diseases* 13(3), 291-297.
Flick, M. R. et al. (1981) "Leukocytes are required for increased lung microvascular permeability after microembolization in sheep," *Circulation Research* 48(3), 344-351.
Furugen, A. et al. (2013) "Contribution of multidrug resistance-associated proteins (MRPs) to the release of prostanoids from A549 cells," *Prostaglandins & Other Lipid Mediators* 106, 37-44.
Galka, F. et al. (2008) "Proteomic characterization of the whole secretome of Legionella pneumophila and functional analysis of outer membrane vesicles," *Infection and Immunity* 76(5), 1825-1836.
Gennuso, F. et al. (2004) "Bilirubin protects astrocytes from its own toxicity by inducing up-regulation and translocation of multidrug resistance-associated protein 1 (Mrp1)," *Proceedings of the National Academy of Sciences of the United States of America* 101(8), 2470-2475.
Hao, Z. et al. (2006) "CIAPIN1 confers multidrug resistance by upregulating the expression of MDR-1 and MRP-1 in gastric cancer cells," *Cancer Biology & Therapy* 5(3), 261-266.
He, S. M. et al. (2011) "Structural and functional properties of human multidrug resistance protein 1 (MRP1/ABCC1)," *Current Medicinal Chemistry* 18(3), 439-481.
Hicks, D. et al. (1985) "Localization of lectin receptors on bovine photoreceptor cells using dextran-gold markers," *Investigative Ophthalmology & Visual Science* 26(7), 1002-1013.
Ho, G.-T. et al. (2005) "Multidrug Resistance (MDR1) Gene in Inflammatory Bowel Disease: A Key Player?," *Inflammatory Bowel Diseases* 11(11), 1013-1019.
Hurley, B. P. et al. (2004) "Polymorphonuclear Cell Transmigration Induced by Pseudomonas aeruginosa Requires the Eicosanoid Hepoxilin A3," *Journal of Immunology* 173(9), 5712.
Jones, M. R. et al. (2005) "Lung NF-κB Activation and Neutrophil Recruitment Require IL-1 and TNF Receptor Signaling during Pneumococcal Pneumonia," *Journal of Immunology* 175(11), 7530-7535.
Knapp, S. et al. (2004) "Toll-Like Receptor 2 Plays a Role in the Early Inflammatory Response to Murine Pneumococcal Pneumonia but Does Not Contribute to Antibacterial Defense," *Journal of Immunology* 172(5), 3132.
Kozhin, P. M. et al. (2015) "Effects of Liposomal Compositions with Oxidized Dextrans on Functional Activity of U937 Macrophage-Like Cells In Vitro," *Bulletin of Experimental Biology and Medicine* 160(1), 57-60.
Lin, Z. P. et al. (2008) "Disruption of cAMP and Prostaglandin E2 Transport by Multidrug Resistance Protein 4 Deficiency Alters CAMP-Mediated Signaling and Nociceptive Response," *Molecular Pharmacology* 73(1), 243.
Loosli, C. G. et al. (1962) "Acute Experimental Pneumococcal (Type I) pneumonia in the Mouse: The Migration of Leucocytes from the Pulmonary Capillaries into the Alveolar Spaces as Revealed by the Electron Microscope," *Transactions of the American Clinical and Climatological Association* 74, 15-28.
Marks, M. et al. (2007) "Influence of neutropenia on the course of serotype 8 pneumococcal pneumonia in mice," *Infection and Immunity* 75(4), 1586-1597.
Menendez, R. et al. (2008) "Markers of treatment failure in hospitalised community acquired pneumonia," *Thorax* 63(5), 447-452.
Mizgerd, J. P. et al. (1999) "Effects of CD18 Deficiency on the Emigration of Murine Neutrophils During Pneumonia," *Journal of Immunology* 163(2), 995.
Mizgerd, J. P. et al. (1996) "Selectins and neutrophil traffic: margination and *Streptococcus pneumoniae*-induced emigration in murine lungs," *Journal of Experimental Medicine* 184(2), 639-645.
Mizgerd, J. P. et al. (1998) "Combinatorial requirements for adhesion molecules in mediating neutrophil emigration during bacterial peritonitis in mice," *Journal of Leukocyte Biology* 64(3), 291-297.
Moore et al. (2015) "Pneumococcal Disease," in *Epidemiology and Prevention of Vaccine-Preventable Diseases Centers for Disease Control and Prevention*. (Hamborsky, et al., Eds.) 13th ed., Public Health Foundation, Washington D.C.
Mrsny, R. J. et al. (2004) "Identification of hepoxilin A3 in inflammatory events: A required role in neutrophil migration across intestinal epithelia," *Proceedings of the National Academy of Sciences of the United States of America* 101(19), 7421.
Mumy, K. L. et al. (2008) "Distinct isoforms of phospholipase A2 mediate the ability of *Salmonella enterica* serotype typhimurium and Shigella flexneri to induce the transepithelial migration of neutrophils," *Infection and Immunity* 76(8), 3614-3627.
Okayasu, I. et al. (1990) "A Novel Method in the Induction of Reliable Experimental Acute and Chronic Ulcerative Colitis in Mice," *Gastroenterology* 98, 694-702.
Pace-Asciak, C. R. et al. (1986) "Epoxide hydratase assay in human platelets using hepoxilin A3 as a lipid substrate," *Biochimica et Biophysica Acta* 875(2), 406-409.
Panwala, C. M. et al. (1998) "A Novel Model of Inflammatory Bowel Disease: Mice Deficient for the Multiple Drug Resistance Gene, *mdr1a*, Spontaneously Develop Colitis," *Journal of Immunology* 161(10), 5733.
Parkos, C. A. et al. (1996) "Expression and Polarization of Intercellular Adhesion Molecule-1 on Human Intestinal Epithelia: Consequences for CD11b/CD18-Mediated Interactions with Neutrophils," *Molecular Medicine* 2(4), 489-505.
Parkos, C. A. et al. (1991) "Neutrophil migration across a cultured intestinal epithelium. Dependence on a CD11b/CD18-mediated

(56) References Cited

OTHER PUBLICATIONS event and enhanced efficiency in physiological direction," *Journal of Clinical Investigation* 88(5), 1605-1612.
Pasut, G. (2014) "Polymers for Protein Conjugation," *Polymers* 6(1), 160-178.
Patricelli, M. P. et al. (2001) "Characterization and Manipulation of the Acyl Chain Selectivity of Fatty Acid Amide Hydrolase," *Biochemistry* 40(20), 6107-6115.
Pazos, M. et al. (2008) "Multidrug Resistance-Associated Transporter 2 Regulates Mucosal Inflammation by Facilitating the Synthesis of Hepoxilin A3," *Journal of Immunology* 181(11), 8044.
Pilishvili, T. et al. (2012) "Chapter 11. Pneumococcal Disease," in *Manual for the surveillance of vaccine-preventable diseases* (Roush, et al., Eds.) 5th ed ed., Centers for Disease Control and Prevention,, Atlanta, GA.
Pulli, B. et al. (2013) "Measuring Myeloperoxidase Activity in Biological Samples," *PLoS One* 8(7), e67976.
Raza, A. et al. (2016) "Increased expression of ATP binding cassette transporter genes following exposure of Haemonchus contortus larvae to a high concentration of monepantel in vitro," *Parasites & Vectors* 9(1), 522.
Robbiani, D. F. et al. (2000) "The Leukotriene C4 Transporter MRP1 Regulates CCL19 (MIP-3β, ELC)—Dependent Mobilization of Dendritic Cells to Lymph Nodes," *Cell* 103(5), 757-768.
Rosenberg, M. F. et al. (2001) "The Structure of the Multidrug Resistance Protein 1 (MRP1/ABCC1): Crystallization and Single-Particle Analysis," *Journal of Biological Chemistry* 276(19), 16076-16082.
Ryberg, E. et al. (2007) "The orphan receptor GPR55 is a novel cannabinoid receptor," *British Journal of Pharmacology* 152(7), 1092-1101.
Sakamoto, A. et al. (2015) "Drug Transporter Protein Quantification of Immortalized Human Lung Cell Lines Derived from Tracheobronchial Epithelial Cells (Calu-3 and BEAS2-B), Bronchiolar-Alveolar Cells (NCI-H292 and NCI-H441), and Alveolar Type II-like Cells (A549) by Liquid Chromatography—Tandem Mass Spectrometry," *Journal of Pharmaceutical Sciences* 104(9), 3029-3038.
Sanchis, J. et al. (2010) "Polymer-drug conjugates for novel molecular targets," *Nanomedicine* (*Lond*) 5(6), 915-935.
Sandborn, W. J. (2016) "The Present and Future of Inflammatory Bowel Disease Treatment," *Gastroenterology & hepatology* 12(7), 438-441.
Schultz, M. J. et al. (2001) "Mice Lacking the Multidrug Resistance Protein 1 are Resistant to *Streptococcus pneumoniae*-Induced Pneumonia," *Journal of Immunology* 166(6), 4059.
Seyoum, B. et al. (2011) "The innate immune response to *Streptococcus pneumoniae* in the lung depends on serotype and host response," *Vaccine* 29(45), 8002-8011.
Singh, U. P. et al. (2012) "Cannabinoid receptor-2 (CB2) agonist ameliorates colitis in IL-10-/-mice by attenuating the activation of T cells and promoting their apoptosis," *Toxicology and Applied Pharmacology* 258(2), 256-267.
Staley, E. M. et al. (2008) "Differential Susceptibility of P-glycoprotein Deficient Mice to Colitis Induction by Environmental Insults," *Inflammatory Bowel Diseases* 15(5), 684-696.
Stolarczyk, E. I. et al. (2011) "Regulation of ABC transporter function via phosphorylation by protein kinases," *Current Pharmaceutical Biotechnology* 12(4), 621-635.
Strohmeier, G. R. et al. (1997) "Surface expression, polarization, and functional significance of CD73 in human intestinal epithelia," *Journal of Clinical Investigation* 99(11), 2588-2601.
Syed, S. K. et al. (2012) "Regulation of GPR119 receptor activity with endocannabinoid-like lipids," *American Journal of Physiology—Endocrinology and Metabolism* 303(12), E1469-1478.
Tasaka, S. et al. (2003) "Platelet Endothelial Cell Adhesion Molecule-1 in Neutrophil Emigration during Acute Bacterial Pneumonia in Mice and Rats," *American Journal of Respiratory and Critical Care Medicine* 167(2), 164-170.
Tasaka, S. et al. (2002) "Very Late Antigen-4 in CD18-Independent Neutrophil Emigration during Acute Bacterial Pneumonia in Mice," *American Journal of Respiratory and Critical Care Medicine* 166(1), 53-60.
Torky, A.-R. W. et al. (2005) "Immuno-histochemical detection of MRPs in human lung cells in culture," *Toxicology* 207(3), 437-450.
Van Der Deen, M. et al. (2006) "Diminished expression of multidrug resistance-associated protein 1 (MRP1) in bronchial epithelium of COPD patients," *Virchows Archiv* 449(6), 682-688.
Van Schilfgaarde, M. et al. (1995) "Paracytosis of Haemophilus influenzae through cell layers of NCI-H292 lung epithelial cells, " *Infection and Immunity* 63(12), 4729-4737.
Westlake, C. J. et al. (2005) "Role of the NH2-terminal membrane spanning domain of multidrug resistance protein 1/ABCC1 in protein processing and trafficking," *Molecular Biology of the Cell* 16(5), 2483-2492.
Wijnholds, J. et al. (1997) "Increased sensitivity to anticancer drugs and decreased inflammatory response in mice lacking the multidrug resistance-associated protein," *Nature Medicine* 3(11), 1275-1279.
Wilk, J. N. et al. (2005) "The mdr1a-/- mouse model of spontaneous colitis," *Immunologic Research* 31(2), 151-159.
World Health Organization. (2012) "Pneumococcal Vaccines (Position paper on pneumococcal vaccines)," *Weekly Epidemiological Record* 87(14), 129-144.
Yacyshyn, B. et al. (1999) "Differences in P-glycoprotein-170 expression and activity between Crohn's disease and ulcerative colitis," *Human Immunology* 60(8), 677-687.
Yin, J.-Y. et al. (2009) "Characterization and analyses of multidrug resistance-associated protein 1 (MRP1/ABCC1) polymorphisms in Chinese population," *Pharmacogenetics and Genomics* 19(3), 206-216.
Yusa, K. et al. (1989) "Reversal Mechanism of Multidrug Resistance by Verapamil: Direct Binding of Verapamil to P-Glycoprotein on Specific Sites and Transport of Verapamil Outward across the Plasma Membrane of K562/ADM Cells," *Cancer Research* 49(18), 5002.
PCT International Search Report of International Application No. PCT/US2018/042116 dated Mar. 11, 2019.
Andrade-Silva, et al. "The Cannabinoid 2 receptor agonist B-caryophyllene modulates the inflammatory reaction induced by Bycobacterium bovis BCG by inhibiting netrophil migration." 4. Inflamm. Res., 2016, vol. 65, pp. 869-879.
Blokzijl et al., "Up-regulation and Cytoprotective Role of Epithelial Multidrug Resistance-associated Protein 1 in Inflammatory Bowel Disease." J. of Biological Chemistry. 2008, vol. 283, No. 51, pp. 35630-35637.
Qing Hai et al., "Synthesis of polymeric drug nanomicrospheres containing probenecid", retrieved from STN Database accession No. 2004:763411.
Qing-Hai et al., "Synthesis and characterization of macromolecular prodrugs carrying probenecid group", retrieved from STN Database accession No. 2004:122914.
Qing-Hai et al., "Synthesis and Characterization of Macromolecular Prodrugs Carrying Probenecid Group", Chinese Journal of Synthetic Chemistry, 2003, vol. 11, pp. 517-519.
Rajesh, et al., "Pivotal Advance: Cannabinoid-2 receptor agonist HU-308 protects against hepatic ischemia/reperfusion injury by attenuating oxidative stress, inflammatory response, and apoptosis." Journal of Leukocyte Biology. 2007, vol. 82, pp. 1382-1389.
Yanling et al., "Effect of Tanreging on Expression of Multidrug Resistance related Protein 1 in Bronchial Epithelium of Rats with Chronic Obstructive Pulmonary Disease", Chinese Journal of Gerontology, 2017, vol. 37, pp. 318-320.
Zheng-Cui et al., "Synthesis of amphiphilic macromolecular prodrugs anchored with probenecid", retrieved from STN Database accession No. 2005:17809.

* cited by examiner

Relative Migration
1.0
0.8
0.6
0.4
0.2
0.0
HXA3 + Veh
1:50
1:100
1:200
AMEND
ns
PMN migrated (normalized)
1.5
1.0
0.5
0.0
HXA3 + veh
control
B4-mdr1
B5-mdr1
ns
ns
Fold migration (normalized to HXA)
2.0
1.5
1.0
0.5
0.0
HXA3 + Veh
+AMEND
+AMEND /FAAH
+AMEND /MAGL
ns
***
Anandamide Na+ adduct
Scrambled control RNA
Pgp RNA knock-down Percent of D0 weight
3% DSS
p=.0053
wt
cnr2-/-
Day Histopathology Score
*p=0.0214

MPO activity
(slope of linear regression)
**p=0.0087 mpo activity(slope)/
µg total protein
p=0.4710

Number of PMN
(live/CD45+CD11b+Ly6G+)
p=0.4825

Percent PMN
(CD11b+Ly6G+
among live CD45+)
p=0.0954

Human 12-lipoxygenase (Alox12) mRNA, complete cds
>gi|187170|gb|M58704.1|HUMLIPXYG (SEQ ID NO:01)

CGGCTCCCCTCGCCTAAGCTGCTGGGGGGCGCCATGGGCCGCTACCGCATCCGCGTGGCCACCGGGGCCT
GGCTCTTCTCCGGGTCGTACAACCGCGTGCAGCTTTGGCTGGTCGGGACGCGCGGGGAGGCGGAGCTGGA
GCTGCAGCTGCGGCCGGCGCGGGGCGAGGAGGAGGAGTTTGATCATGACGTTGCAGAGGACTTGGGGCTC
CTGCAGTTCGTGAGGCTGCGCAAGCACCACTGGCTGGTGGACGACGCGTGGTTCTGCGACCGCATCACGG
TGCAGGGCCCTGGAGCCTGCGCGGAGGTGGCCTTCCCGTGCTACCGCTGGGTGCAGGGCGAGGACATCCT
GAGCCTGCCCGAGGGCACCGCCCGCCTGCCAGGAGACAATGCTTTGGACATGTTCCAGAAGCATCGAGAG
AAGGAACTGAAAGACAGACAGCAGATCTACTGCTGGGCCACCTGGAAGGAAGGGTTACCCCTGACCATCG
CTGCAGACCGTAAGGATGATCTACCTCCAAATATGAGATTCCATGAGGAGAAGAGGCTGGACTTTGAATG
GACACTGAAGGCAGGGGCTCTGGAGATGGCCCTCAAACGTGTTTACACCCTCCTGAGCTCCTGGAACTGC
CTAGAAGACTTTGATCAGATCTTCTGGGGCCAGAAGAGTGCCCTGGCTGAGAAGGTTCGCCAGTGCTGGC
AGGATGATGAGTTGTTCAGCTACCAGTTCCTCAATGGTGCCAACCCCATGCTGTTGAGACGCTCGACCTC
TCTGCCCTCCAGGCTAGTGCTGCCCTCAGGGATGGAAGAGCTTCGGGCTCAACTGGAGAAAGAACTTCAG
AATGGTTCCCTGTTTGAAGCTGACTTCATCCTTCTGGATGGAATTCCAGCCAACGTGATCCGAGGAGAGA
AGCAATACCTGGCTGCCCCCCTCGTTATGCTGAAGATGGAGCCCAATGGGAAGCTGCAGCCCATGGTCAT
CCAGATTCAGCCTCCCAACCCCAGCTCTCCAACCCCAACACTGTTCCTGCCCTCAGACCCCCCACTTGCC
TGGCTCCTGGCAAAGTCCTGGGTCCGAAATTCAGATTTCCAACTGCACGAGATCCAGTATCACTTGCTGA
ACACGCACCTGGTGGCTGAGGTCATCGCTGTCGCCACCATGCGGTGCCTCCCAGGACTGCACCCCATCTT
CAAGTTCCTGATCCCCCATATCCGCTACACCATGGAAATCAACACCCGGGCCCGGACCCAACTCATCTCA
GATGGAGGAATTTTTGATAAGGCAGTGAGCACAGGTGGAGGGGGCCATGTACAGTTGCTCCGTCGGGCGG
CAGCTCAGCTGACCTACTGCTCCCTCTGTCCTCCTGACGACCTGGCTGACCGGGGCCTGCTGGGACTCCC
AGGTGCTCTCTATGCCCATGATGCTTTACGGCTCTGGGAGATCATTGCCAGGTATGTGGAGGGGATCGTC
CACCTCTTCTACCAAAGGGATGACATAGTGAAGGGGGACCCTGAGCTGCAGGCCTGGTGTCGGGAGATCA
CGGAGGTGGGGCTGTGCCAGGCCCAGGACCGAGGTTTCCCTGTCTCCTTCCAGTCCCAGAGTCAACTCTG
CCATTTCCTCACCATGTGCGTCTTCACGTGCACTGCCCAGCATGCCGCCATCAACCAGGGCCAGCTGGAC
TGGTATGCCTGGGTCCCTAATGCTCCATGCACAATGCGGATGCCCCCACCCACCACCAAGGAAGATGTGA
CGATGGCCACAGTGATGGGGTCACTACCTGATGTCCGGCAGGCCTGTCTTCAAATGGCCATCTCATGGCA
TCTGAGTCGCCGCCAGCCAGACATGGTGCCTCTGGGGCACCACAAAGAAAAATATTTCTCAGGCCCCAAG
CCCAAAGCTGTGCTAAACCAATTCCGAACAGATTTGGAAAAGCTGGAAAAGGAGATTACAGCCCGGAATG
AGCAACTTGACTGGCCCTATGAATATCTGAAGCCCAGCTGCATAGAGAACAGTGTCACCATCTGAGCCCT
AGAGTGACTCTACCTGCAAGATTTCACATCAGCTTTAGGACTGACATTTCTATCTTGAATTTCATGCTTT
CCTAAAGTCTCTGCTGCTAAGGCTCTATTTCCTCCCCCAGTTAAACCCCCTACATTAGTATCCCACTAGC
CCAGGGGAGCAGTAAACTTTCTCTGCAAAGACTAGATCCTTTTTTACGCTTTGCAGACCGCATAGTCACT
GTCTCAACTACTCAGCTCTCCTGCTGCAGCATGAAGGCAGCCACAGACAACATGGAAATGAGTGTGACTA
TGTTCCAATAAAACTTTATGGACAC

FIG. 12

Homo sapiens ATP binding cassette subfamily C member 2 (ABCC2), mRNA
>gi|594191052|ref|NM_000392.4| (SEQ ID NO:02)

TACTTTGGGAACTGGTGAGTCTCCCTGTCCCTAGGGCTTTTTAGTCACATGTCCATCCACTGTTTCAATG
TAACATGCATCTAGGCAAGGTTAACGATTAAATGGTTGGGATGAAAGGTCATCCTTTACGGAGAACATCA
GAATGGTAGATAATTCCTGTTCCACTTTCTTTGATGAAACAAGTAAAGAAGAAACAACACAATCATATTA
ATAGAAGAGTCTTCGTTCCAGACGCAGTCCAGGAATCATGCTGGAGAAGTTCTGCAACTCTACTTTTTGG
AATTCCTCATTCCTGGACAGTCCGGAGGCAGACCTGCCACTTTGTTTTGAGCAAACTGTTCTGGTGTGGA
TTCCCTTGGGCTTCCTATGGCTCCTGGCCCCCTGGCAGCTTCTCCACGTGTATAAATCCAGGACCAAGAG
ATCCTCTACCACCAAACTCTATCTTGCTAAGCAGGTATTCGTTGGTTTTCTTCTTATTCTAGCAGCCATA
GAGCTGGCCCTTGTACTCACAGAAGACTCTGGACAAGCCACAGTCCCTGCTGTTCGATATACCAATCCAA
GCCTCTACCTAGGCACATGGCTCCTGGTTTTGCTGATCCAATACAGCAGACAATGGTGTGTACAGAAAAA
CTCCTGGTTCCTGTCCCTATTCTGGATTCTCTCGATACTCTGTGGCACTTTCCAATTTCAGACTCTGATC
CGGACACTCTTACAGGGTGACAATTCTAATCTAGCCTACTCCTGCCTGTTCTTCATCTCCTACGGATTCC
AGATCCTGATCCTGATCTTTTCAGCATTTTCAGAAAATAATGAGTCATCAAATAATCCATCATCCATAGC
TTCATTCCTGAGTAGCATTACCTACAGCTGGTATGACAGCATCATTCTGAAAGGCTACAAGCGTCCTCTG
ACACTCGAGGATGTCTGGGAAGTTGATGAAGAGATGAAAACCAAGACATTAGTGAGCAAGTTTGAAACGC
ACATGAAGAGAGAGCTGCAGAAAGCCAGGCGGGCACTCCAGAGACGGCAGGAGAAGAGCTCCCAGCAGAA
CTCTGGAGCCAGGCTGCCTGGCTTGAACAAGAATCAGAGTCAAAGCCAAGATGCCCTTGTCCTGGAAGAT
GTTGAAAAGAAAAAAAAGAAGTCTGGGACCAAAAAAGATGTTCCAAAATCCTGGTTGATGAAGGCTCTGT
TCAAAACTTTCTACATGGTGCTCCTGAAATCATTCCTACTGAAGCTAGTGAATGACATCTTCACGTTTGT
GAGTCCTCAGCTGCTGAAATTGCTGATCTCCTTTGCAAGTGACCGTGACACATATTTGTGGATTGGATAT
CTCTGTGCAATCCTCTTATTCACTGCGGCTCTCATTCAGTCTTTCTGCCTTCAGTGTTATTTCCAACTGT
GCTTCAAGCTGGGTGTAAAAGTACGGACAGCTATCATGGCTTCTGTATATAAGAAGGCATTGACCCTATC
CAACTTGGCCAGGAAGGAGTACACCGTTGGAGAAACAGTGAACCTGATGTCTGTGGATGCCCAGAAGCTC
ATGGATGTGACCAACTTCATGCACATGCTGTGGTCAAGTGTTCTACAGATTGTCTTATCTATCTTCTTCC
TATGGAGAGAGTTGGGACCCTCAGTCTTAGCAGGTGTTGGGGTGATGGTGCTTGTAATCCCAATTAATGC
GATACTGTCCACCAAGAGTAAGACCATTCAGGTCAAAAATATGAAGAATAAAGACAAACGTTTAAAGATC
ATGAATGAGATTCTTAGTGGAATCAAGATCCTGAAATATTTTGCCTGGGAACCTTCATTCAGAGACCAAG
TACAAAACCTCCGGAAGAAAGAGCTCAAGAACCTGCTGGCCTTTAGTCAACTACAGTGTGTAGTAATATT
CGTCTTCCAGTTAACTCCAGTCCTGGTATCTGTGGTCACATTTTCTGTTTATGTCCTGGTGGATAGCAAC
AATATTTTGGATGCACAAAAGGCCTTCACCTCCATTACCCTCTTCAATATCCTGCGCTTTCCCCTGAGCA
TGCTTCCCATGATGATCTCCTCCATGCTCCAGGCCAGTGTTTCCACAGAGCGGCTAGAGAAGTACTTGGG
AGGGGATGACTTGGACACATCTGCCATTCGACATGACTGCAATTTTGACAAAGCCATGCAGTTTTCTGAG
GCCTCCTTTACCTGGGAACATGATTCGGAAGCCACAGTCCGAGATGTGAACCTGGACATTATGGCAGGCC
AACTTGTGGCTGTGATAGGCCCTGTCGGCTCTGGGAAATCCTCCTTGATATCAGCCATGCTGGGAGAAAT
GGAAAATGTCCACGGGCACATCACCATCAAGGGCACCACTGCCTATGTCCCACAGCAGTCCTGGATTCAG
AATGGCACCATAAAGGACAACATCCTTTTTGGAACAGAGTTTAATGAAAAGAGGTACCAGCAAGTACTGG
AGGCCTGTGCTCTCCTCCCAGACTTGGAAATGCTGCCTGGAGGAGATTTGGCTGAGATTGGAGAGAAGGG
TATAAATCTTAGTGGGGGTCAGAAGCAGCGGATCAGCCTGGCCAGAGCTACCTACCAAAATTTAGACATC
TATCTTCTAGATGACCCCCTGTCTGCAGTGGATGCTCATGTAGGAAAACATATTTTTAATAAGGTCTTGG
GCCCCAATGGCCTGTTGAAAGGCAAGACTCGACTCTTGGTTACACATAGCATGCACTTTCTTCCTCAAGT
GGATGAGATTGTAGTTCTGGGGAATGGAACAATTGTAGAGAAAGGATCCTACAGTGCTCTCCTGGCCAAA
AAAGGAGAGTTTGCTAAGAATCTGAAGACATTTCTAAGACATACAGGCCCTGAAGAGGAAGCCACAGTCC
ATGATGGCAGTGAAGAAGAAGACGATGACTATGGGCTGATATCCAGTGTGGAAGAGATCCCCGAAGATGC
AGCCTCCATAACCATGAGAAGAGAGAACAGCTTTCGTCGAACACTTAGCCGCAGTTCTAGGTCCAATGGC
AGGCATCTGAAGTCCCTGAGAAACTCCTTGAAAACTCGGAATGTGAATAGCCTGAAGGAAGACGAAGAAC
TAGTGAAAGGACAAAAACTAATTAAGAAGGAATTCATAGAAACTGGAAAGGTGAAGTTCTCCATCTACCT
GGAGTACCTACAAGCAATAGGATTGTTTTCGATATTCTTCATCATCCTTGCGTTTGTGATGAATTCTGTG
GCTTTTATTGGATCCAACCTCTGGCTCAGTGCTTGGACCAGTGACTCTAAAATCTTCAATAGCACCGACT
ATCCAGCATCTCAGAGGGACATGAGAGTTGGAGTCTACGGAGCTCTGGGATTAGCCCAAGGTATATTTGT

FIG. 12 CONT'D

GTTCATAGCACATTTCTGGAGTGCCTTTGGTTTCGTCCATGCATCAAATATCTTGCACAAGCAACTGCTG
AACAATATCCTTCGAGCACCTATGAGATTTTTGACACAACACCCACAGGCCGGATTGTGAACAGGTTTG
CCGGCGATATTTCCACAGTGGATGACACCCTGCCTCAGTCCTTGCGCAGCTGGATTACATGCTTCCTGGG
GATAATCAGCACCCTTGTCATGATCTGCATGGCCACTCCTGTCTTCACCATCATCGTCATTCCTCTTGGC
ATTATTTATGTATCTGTTCAGATGTTTTATGTGTCTACCTCCCGCCAGCTGAGGCGTCTGGACTCTGTCA
CCAGGTCCCCAATCTACTCTCACTTCAGCGAGACCGTATCAGGTTTGCCAGTTATCCGTGCCTTTGAGCA
CCAGCAGCGATTTCTGAAACACAATGAGGTGAGGATTGACACCAACCAGAAATGTGTCTTTTCCTGGATC
ACCTCCAACAGGTGGCTTGCAATTCGCCTGGAGCTGGTTGGGAACCTGACTGTCTTCTTTTCAGCCTTGA
TGATGGTTATTTATAGAGATACCCTAAGTGGGGACACTGTTGGCTTTGTTCTGTCCAATGCACTCAATAT
CACACAAACCCTGAACTGGCTGGTGAGGATGACATCAGAAATAGAGACCAACATTGTGGCTGTTGAGCGA
ATAACTGAGTACACAAAAGTGGAAAATGAGGCACCCTGGGTGACTGATAAGAGGCCTCCGCCAGATTGGC
CCAGCAAAGGCAAGATCCAGTTTAACAACTACCAAGTGCGGTACCGACCTGAGCTGGATCTGGTCCTCAG
AGGGATCACTTGTGACATCGGTAGCATGGAGAAGATTGGTGTGGTGGGCAGGACAGGAGCTGGAAAGTCA
TCCCTCACAAACTGCCTCTTCAGAATCTTAGAGGCTGCCGGTGGTCAGATTATCATTGATGGAGTAGATA
TTGCTTCCATTGGGCTCCACGACCTCCGAGAGAAGCTGACCATCATCCCCCAGGACCCCATCCTGTTCTC
TGGAAGCCTGAGGATGAATCTCGACCCTTTCAACAACTACTCAGATGAGGAGATTTGGAAGGCCTTGGAG
CTGGCTCACCTCAAGTCTTTTGTGGCCAGCCTGCAACTTGGGTTATCCCACGAAGTGACAGAGGCTGGTG
GCAACCTGAGCATAGGCCAGAGGCAGCTGCTGTGCCTGGGCAGGGCTCTGCTTCGGAAATCCAAGATCCT
GGTCCTGGATGAGGCCACTGCTGCGGTGGATCTAGAGACAGACAACCTCATTCAGACGACCATCCAAAAC
GAGTTCGCCCACTGCACAGTGATCACCATCGCCCACAGGCTGCACACCATCATGGACAGTGACAAGGTAA
TGGTCCTAGACAACGGGAAGATTATAGAGTGCGGCAGCCCTGAAGAACTGCTACAAATCCCTGGACCCTT
TTACTTTATGGCTAAGGAAGCTGGCATTGAGAATGTGAACAGCACAAAATTCTAGCAGAAGGCCCCATGG
GTTAGAAAAGGACTATAAGAATAATTTCTTATTTAATTTTATTTTTTATAAAATACAGAATACATACAAA
AGTGTGTATAAAATGTACGTTTTAAAAAAGGATAAGTGAACACCCATGAACCTACTACCCAGGTTAAGAA
AATAAATGTCACCAGGTACTTGAGAAACCCCTCGATTGTCTACCTCGATCGTACTTCCTTGCTACCCACC
CCTCCCAGGGACAACCACTGTCCTGAATTTCACGATAATTATTCCTTTGCCTTTCATTTCTGTTTTATCA
CCTTTGTATGTATCTTTAAACAACATATACCCTTTTTTACTTATGTAAATGGACTGACTCATACTGCATA
CATCTTCTATGACTTGATTCTTTTGTTCAATATTATATCTGAGATTCATCCATGGTGATGCAAATAGGTG
CATTATTTTTTTTCACTGCTCTGTAGTCTGGCATTGTATGAATACAGCACAATGTATCAGTTTTAATATT
GGGGATCATTAGCATTATTCTCAGGTTTTTAAAAATTATAAGCAGTACTACTATGG

FIG. 13

Homo sapiens ATP-binding cassette, sub-family B (MDR/TAP), member 1
(ABCB1), mRNA
>gi|318037598|ref|NM_000927.4| (SEQ ID NO:03)

AAACACTTGTATTACCATTTTAAAGGCTATCATTACTCTTTACCTGTGAAGAGTAGAACATGAAGAAATC
TACTTTATTCAGATATTCTCCAGATTCCTAAAGATTAGAGATCATTTCTCATTCTCCTAGGAGTACTCAC
TTCAGGAAGCAACCAGATAAAAGAGAGGTGCAACGGAAGCCAGAACATTCCTCCTGGAAATTCAACCTGT
TTCGCAGTTTCTCGAGGAATCAGCATTCAGTCAATCCGGGCCGGGAGCAGTCATCTGTGGTGAGGCTGAT
TGGCTGGGCAGGAACAGCGCCGGGGCGTGGGCTGAGCACAGCCGCTTCGCTCTCTTTGCCACAGGAAGCC
TGAGCTCATTCGAGTAGCGGCTCTTCCAAGCTCAAAGAAGCAGAGGCCGCTGTTCGTTTCCTTTAGGTCT
TTCCACTAAAGTCGGAGTATCTTCTTCCAAAATTTCACGTCTTGGTGGCCGTTCCAAGGAGCGCGAGGTC
GGAATGGATCTTGAAGGGGACCGCAATGGAGGAGCAAAGAAGAAGAACTTTTTTAAACTGAACAATAAAA
GTGAAAAAGATAAGAAGGAAAAGAAACCAACTGTCAGTGTATTTTCAATGTTTCGCTATTCAAATTGGCT
TGACAAGTTGTATATGGTGGTGGGAACTTTGGCTGCCATCATCCATGGGGCTGGACTTCCTCTCATGATG
CTGGTGTTTGGAGAAATGACAGATATCTTTGCAAATGCAGGAAATTTAGAAGATCTGATGTCAAACATCA
CTAATAGAAGTGATATCAATGATACAGGGTTCTTCATGAATCTGGAGGAAGACATGACCAGGTATGCCTA
TTATTACAGTGGAATTGGTGCTGGGGTGCTGGTTGCTGCTTACATTCAGGTTTCATTTTGGTGCCTGGCA
GCTGGAAGACAAATACACAAAATTAGAAAACAGTTTTTTCATGCTATAATGCGACAGGAGATAGGCTGGT
TTGATGTGCACGATGTTGGGGAGCTTAACACCCGACTTACAGATGATGTCTCCAAGATTAATGAAGGAAT
TGGTGACAAAATTGGAATGTTCTTTCAGTCAATGGCAACATTTTTCACTGGGTTTATAGTAGGATTTACA
CGTGGTTGGAAGCTAACCCTTGTGATTTTGGCCATCAGTCCTGTTCTTGGACTGTCAGCTGCTGTCTGGG
CAAAGATACTATCTTCATTTACTGATAAAGAACTCTTAGCGTATGCAAAAGCTGGAGCAGTAGCTGAAGA
GGTCTTGGCAGCAATTAGAACTGTGATTGCATTTGGAGGACAAAAGAAAGAACTTGAAAGGTACAACAAA
AATTTAGAAGAAGCTAAAAGAATTGGGATAAAGAAAGCTATTACAGCCAATATTTCTATAGGTGCTGCTT
TCCTGCTGATCTATGCATCTTATGCTCTGGCCTTCTGGTATGGGACCACCTTGGTCCTCTCAGGGGAATA
TTCTATTGGACAAGTACTCACTGTATTCTTTTCTGTATTAATTGGGGCTTTTAGTGTTGGACAGGCATCT
CCAAGCATTGAAGCATTTGCAAATGCAAGAGGAGCAGCTTATGAAATCTTCAAGATAATTGATAATAAGC
CAAGTATTGACAGCTATTCGAAGAGTGGGCACAAACCAGATAATATTAAGGGAAATTTGGAATTCAGAAA
TGTTCACTTCAGTTACCCATCTCGAAAAGAAGTTAAGATCTTGAAGGGTCTGAACCTGAAGGTGCAGAGT
GGGCAGACGGTGGCCCTGGTTGGAAACAGTGGCTGTGGGAAGAGCACAACAGTCCAGCTGATGCAGAGGC
TCTATGACCCCACAGAGGGGATGGTCAGTGTTGATGGACAGGATATTAGGACCATAAATGTAAGGTTTCT
ACGGGAAATCATTGGTGTGGTGAGTCAGGAACCTGTATTGTTTGCCACCACGATAGCTGAAAACATTCGC
TATGGCCGTGAAAATGTCACCATGGATGAGATTGAGAAAGCTGTCAAGGAAGCCAATGCCTATGACTTTA
TCATGAAACTGCCTCATAAATTTGACACCCTGGTTGGAGAGAGAGGGGCCCAGTTGAGTGGTGGGCAGAA
GCAGAGGATCGCCATTGCACGTGCCCTGGTTCGCAACCCCAAGATCCTCCTGCTGGATGAGGCCACGTCA
GCCTTGGACACAGAAAGCGAAGCAGTGGTTCAGGTGGCTCTGGATAAGGCCAGAAAAGGTCGGACCACCA
TTGTGATAGCTCATCGTTTGTCTACAGTTCGTAATGCTGACGTCATCGCTGGTTTCGATGATGGAGTCAT
TGTGGAGAAAGGAAATCATGATGAACTCATGAAAGAGAAAGGCATTTACTTCAAACTTGTCACAATGCAG
ACAGCAGGAAATGAAGTTGAATTAGAAAATGCAGCTGATGAATCCAAAAGTGAAATTGATGCCTTGGAAA
TGTCTTCAAATGATTCAAGATCCAGTCTAATAAGAAAAAGATCAACTCGTAGGAGTGTCCGTGGATCACA
AGCCCAAGACAGAAAGCTTAGTACCAAAGAGGCTCTGGATGAAAGTATACCTCCAGTTTCCTTTTGGAGG
ATTATGAAGCTAAATTTAACTGAATGGCCTTATTTTGTTGTTGGTGTATTTTGTGCCATTATAAATGGAG
GCCTGCAACCAGCATTTGCAATAATATTTTCAAAGATTATAGGGGTTTTTACAAGAATTGATGATCCTGA
AACAAAACGACAGAATAGTAACTTGTTTTCACTATTGTTTCTAGCCCTTGGAATTATTTCTTTTATTACA
TTTTTCCTTCAGGGTTTCACATTTGGCAAAGCTGGAGAGATCCTCACCAAGCGGCTCCGATACATGGTTT
TCCGATCCATGCTCAGACAGGATGTGAGTTGGTTTGATGACCCTAAAAACACCACTGGAGCATTGACTAC
CAGGCTCGCCAATGATGCTGCTCAAGTTAAAGGGGCTATAGGTTCCAGGCTTGCTGTAATTACCCAGAAT
ATAGCAAATCTTGGGACAGGAATAATTATATCCTTCATCTATGGTTGGCAACTAACACTGTTACTCTTAG
CAATTGTACCCATCATTGCAATAGCAGGAGTTGTTGAAATGAAAATGTTGTCTGGACAAGCACTGAAAGA
TAAGAAAGAACTAGAAGGTTCTGGGAAGATCGCTACTGAAGCAATAGAAAACTTCCGAACCGTTGTTTCT
TTGACTCAGGAGCAGAAGTTTGAACATATGTATGCTCAGAGTTTGCAGGTACCATACAGAAACTCTTTGA

FIG. 13 CONT'D

GGAAAGCACACATCTTTGGAATTACATTTTCCTTCACCCAGGCAATGATGTATTTTTCCTATGCTGGATG
TTTCCGGTTTGGAGCCTACTTGGTGGCACATAAACTCATGAGCTTTGAGGATGTTCTGTTAGTATTTTCA
GCTGTTGTCTTTGGTGCCATGGCCGTGGGGCAAGTCAGTTCATTTGCTCCTGACTATGCCAAAGCCAAAA
TATCAGCAGCCCACATCATCATGATCATTGAAAAAACCCCTTTGATTGACAGCTACAGCACGGAAGGCCT
AATGCCGAACACATTGGAAGGAAATGTCACATTTGGTGAAGTTGTATTCAACTATCCCACCCGACCGGAC
ATCCCAGTGCTTCAGGGACTGAGCCTGGAGGTGAAGAAGGGCCAGACGCTGGCTCTGGTGGGCAGCAGTG
GCTGTGGGAAGAGCACAGTGGTCCAGCTCCTGGAGCGGTTCTACGACCCCTTGGCAGGGAAAGTGCTGCT
TGATGGCAAAGAAATAAAGCGACTGAATGTTCAGTGGCTCCGAGCACACCTGGGCATCGTGTCCCAGGAG
CCCATCCTGTTTGACTGCAGCATTGCTGAGAACATTGCCTATGGAGACAACAGCCGGGTGGTGTCACAGG
AAGAGATTGTGAGGGCAGCAAAGGAGGCCAACATACATGCCTTCATCGAGTCACTGCCTAATAAATATAG
CACTAAAGTAGGAGACAAAGGAACTCAGCTCTCTGGTGGCCAGAAACAACGCATTGCCATAGCTCGTGCC
CTTGTTAGACAGCCTCATATTTTGCTTTTGGATGAAGCCACGTCAGCTCTGGATACAGAAAGTGAAAAGG
TTGTCCAAGAAGCCCTGGACAAAGCCAGAGAAGGCCGCACCTGCATTGTGATTGCTCACCGCCTGTCCAC
CATCCAGAATGCAGACTTAATAGTGGTGTTTCAGAATGGCAGAGTCAAGGAGCATGGCACGCATCAGCAG
CTGCTGGCACAGAAAGGCATCTATTTTTCAATGGTCAGTGTCCAGGCTGGAACAAAGCGCCAGTGAACTC
TGACTGTATGAGATGTTAAATACTTTTTAATATTTGTTTAGATATGACATTTATTCAAAGTTAAAAGCAA
ACACTTACAGAATTATGAAGAGGTATCTGTTTAACATTTCCTCAGTCAAGTTCAGAGTCTTCAGAGACTT
CGTAATTAAAGGAACAGAGTGAGAGACATCATCAAGTGGAGAGAAATCATAGTTTAAACTGCATTATAAA
TTTTATAACAGAATTAAAGTAGATTTTAAAAGATAAAATGTGTAATTTTGTTTATATTTTCCCATTTGGA
CTGTAACTGACTGCCTTGCTAAAAGATTATAGAAGTAGCAAAAAGTATTGAAATGTTTGCATAAAGTGTC
TATAATAAAACTAAACTTTCATGTGAAA

FIG. 14

TGCAAGATGGGTGTCTACCGCATCCGCGTCTCCACCGGAGACTCCAAGTACGCGGGCTCCAACAACGAGG
TCTACCTGTGGTTGGTTGGACAGCATGGAGAGGCATCTCTCGGGAAGCTGCTACGACCCTGTCGGGACTC
GGAAGCAGAATTCAAAGTGGATGTGTCAGGATACCTTGGGCCACTGCTGTTCGTAAGAGTGCAGAAATGG
CATTATCTCACGGATGACGCCTGGTTCTGCAACTGGATTTCTGTGAAGGGCCCCGGAGACCAAGGATCAG
AGTACATGTTCCCCTGTTACCGATGGGTTCAGGGCAGAAGCATCCTGAGCCTCCCTGAGGGCACTGGCTG
CACCGTGGTTGAAGATTCTCAAGGACTGTTCAGGAAACATAGGGAAGAGGAGCTTGAAGAGAGGAGGAGT
CTGTACAGGTGGGGCAACTGGAAGGATGGCTCAATCCTGAATGTGGCGGCGGCCAGTATATCTGACCTCC
CTGTAGACCAACGATTTCGAGAGGACAAAAGAATTGAATTTGAAGCTTCACAGGTTATAGGGGTAATGGA
TACTGTTGTCAACTTTCCTATAAACACTGTGACCTGCTGGAAAAGCCTAGATGACTTCAACTGCGTTTTC
AAGAGTGGCCATACCAAAATGGCTGAGCGGGTTCGAAACTCCTGGAAGGAAGATGCGTTCTTTGGGTACC
AATTCCTCAATGGTGCTAACCCCATGGTGCTGAAGCGCTCTACTTGTCTTCCTGCCCGCCTGGTATTCCC
TCCAGGAATGGAGAAGCTACAGGCCCAGCTGAACAAGGAGCTCCAGAAAGGCACTCTGTTTGAAGCGGAT
TTCTTCCTTCTGGATGGGATCAAGGCCAATGTCATCCTTTGTAGCCAGCAGTACCTGGCTGCCCCTCTCG
TCATGCTGAAGCTGATGCCTGATGGACAACTCTTGCCCATAGCCATCCAGCTTGAACTTCCCAAAACTGG
GTCTACTCCACCACCTATTTTCACGCCCTCGGATCCCCCAATGGACTGGCTCCTAGCCAAATGCTGGGTC
CGGAGCTCCGACTTACAGCTCCATGAGCTGCAGGCTCATCTTCTGAGGGGACACTTGATGGCTGAGGTCT
TTGCTGTGGCCACCATGAGGTGCCTGCCTTCCGTGCACCCTGTTTTTAAGCTTCTAGTTCCTCATCTGCT
TTACACCATGGAAATTAATGTCCGGGCCAGGAGTGACCTGATCTCAGAGAGAGGCTTTTTTGACAAGGCA
ATGAGCACAGGTGGGGGAGGCCACCTGGATCTTCTCAAGCAAGCTGGAGCCTTTCTGACCTATTGCTCAT
TGTGTCCCCCCGATGACTTGGCTGAGCGAGGACTCTTGGATATCGAGACTTGCTTCTATGCTAAAGACGC
CCTGCGACTCTGGCAGATCATGAATCGGTACGTGGTGGGAATGTTCAATCTCCACTACAAGACCGACAAA
GCTGTGCAAGACGACTATGAACTGCAGAGCTGGTGTCGAGAGATCACTGACATTGGTCTTCAAGGGGCCC
AGGACAGAGGCTTCCCTACCTCTCTTCAGTCCCGGGCTCAGGCTTGCTACTTCATCACCATGTGCATCTT
CACGTGCACCGCACAGCACTCTTCCGTCCATCTTGGCCAGCTGGATTGGTTCTACTGGGTTCCTAATGCA
CCCTGCACCATGCGGCTGCCACCACCCACCACCAAGGAAGCAACAATGGAGAAGCTGATGGCTACACTGC
CCAACCCTAATCAGTCTACTCTCCAGATAAATGTCGTTTGGCTCCTGGGCAGACGCCAGGCTGTTATGGT
GCCCCTGGGCCAGCATTCAGAGGAACACTTTCCAAACCCTGAGGCCAAGGCTGTGCTGAAGAAGTTCAGA
GAGGAACTGGCTGCCTTGGATAAGGAAATTGAGATTCGTAATAAGAGCTTGGACATACCTTATGAGTACC
TGCGGCCCAGCATGGTGGAAAACAGCGTGGCCATATGAGCATCCCCAGACTCCTGCTTTGTTGTTTAGTT
AAGACCACCCAAGTACATCCCTGTGCTTGAGTGGTGGCAGTCCTGCCCTCCCAAGCCCCGCCCTCTGACC
CTCAAAGCCCCACCCCCTGCCCATGTGGGACCCTCCTCCAAGCTGTCCATTGTCTGCTGCAATGAATACA
TTTTGCTTTGGATGCATTAAAAAAAAAAAAAAAAAAAAAAAAAAAA

FIG. 15

Human FAAH: Homo sapiens fatty acid amide hydrolase (FAAH), mRNA
>gi|166795286|ref|NM_001441.2| (SEQ ID NO:05)

TCCGGGTTTTGCGGCGGAGCGGGCGGGCTGCGCGTGCGGCGGCTTCAACTGTCGCGGTAGGCAGCAGCAG
GCTGAAGGGATCATGGTGCAGTACGAGCTGTGGGCCGCGCTGCCTGGCGCCTCCGGGGTCGCCCTGGCCT
GCTGCTTCGTGGCGGCGGCCGTGGCCCTGCGCTGGTCCGGGCGCCGGACGGCGCGGGGCGCGGTGGTCCG
GGCGCGACAGAGGCAGCGAGCGGGCCTGGAGAACATGGACAGGGCGGCGCAGCGCTTCCGGCTCCAGAAC
CCAGACCTGGACTCAGAGGCGCTGCTAGCCCTGCCCCTGCCTCAGCTGGTGCAGAAGTTACACAGTAGAG
AGCTGGCCCCTGAGGCCGTGCTCTTCACCTATGTGGGAAAGGCCTGGGAAGTGAACAAAGGGACCAACTG
TGTGACCTCCTATCTGGCTGACTGTGAGACTCAGCTGTCTCAGGCCCCAAGGCAGGGCCTGCTCTATGGC
GTCCCTGTGAGCCTCAAGGAGTGCTTCACCTACAAGGGCCAGGACTCCACGCTGGGCTTGAGCCTGAATG
AAGGGGTGCCGGCGGAGTGCGACAGCGTAGTGGTGCATGTGCTGAAGCTGCAGGGTGCCGTGCCCTTCGT
GCACACCAATGTTCCACAGTCCATGTTCAGCTATGACTGCAGTAACCCCCTCTTTGGCCAGACCGTGAAC
CCATGGAAGTCCTCCAAAAGCCCAGGGGGCTCCTCAGGGGGTGAAGGGGCCCTCATCGGGTCTGGAGGCT
CCCCCCTGGGCTTAGGCACTGATATCGGAGGCAGCATCCGCTTCCCCTCCTCCTTCTGCGGCATCTGCGG
CCTCAAGCCCACAGGGAACCGCCTCAGCAAGAGTGGCCTGAAGGGCTGTGTCTATGGACAGGAGGCAGTG
CGTCTCTCCGTGGGCCCCATGGCCCGGGACGTGGAGAGCCTGGCACTGTGCCTGCGAGCCCTGCTGTGCG
AGGACATGTTCCGCTTGGACCCCACTGTGCCTCCCTTGCCCTTCAGAGAAGAGGTCTACACCAGCTCTCA
GCCCCTGCGTGTGGGGTACTATGAGACTGACAACTATACCATGCCCTCCCCGGCCATGAGGCGGGCCGTG
CTGGAGACCAAACAGAGCCTTGAGGCTGCGGGGCACACGCTGGTTCCCTTCTTGCCAAGCAACATACCCC
ATGCTCTGGAGACCCTGTCAACAGGTGGGCTCTTCAGTGATGGTGGCCACACCTTCCTACAGAACTTCAA
AGGTGATTTCGTGGACCCCTGCCTGGGGGACCTGGTCTCAATTCTGAAGCTTCCCCAATGGCTTAAAGGA
CTGCTGGCCTTCCTGGTGAAGCCTCTGCTGCCAAGGCTGTCAGCTTTCCTCAGCAACATGAAGTCTCGTT
CGGCTGGAAAACTCTGGGAACTGCAGCACGAGATCGAGGTGTACCGCAAAACCGTGATTGCCCAGTGGAG
GGCGCTGGACCTGGATGTGGTGCTGACCCCCATGCTGGCCCCTGCTCTGGACTTGAATGCCCCAGGCAGG
GCCACAGGGGCCGTCAGCTACACTATGCTGTACAACTGCCTGGACTTCCCTGCAGGGGTGGTGCCTGTCA
CCACGGTGACTGCTGAGGACGAGGCCCAGATGGAACATTACAGGGGCTACTTTGGGGATATCTGGGACAA
GATGCTGCAGAAGGGCATGAAGAAGAGTGTGGGGCTGCCGGTGGCCGTGCAGTGTGTGGCTCTGCCCTGG
CAAGAAGAGTTGTGTCTGCGGTTCATGCGGGAGGTGGAGCGACTGATGACCCCTGAAAAGCAGTCATCCT
GATGGCTCTGGCTCCAGAGGACCTGAGACTCACACTCTCTGCAGCCCAGCCTAGTCAGGGCACAGCTGCC
CTGCTGCCACAGCAAGGAAATGTCCTGCATGGGGCAGAGGCTTCCGTGTCCTCTCCCCCAACCCCCTGCA
AGAAGCGCCGACTCCCTGAGTCTGGACCTCCATCCCTGCTCTGGTCCCCTCTCTTCGTCCTGATCCCTCC
ACCCCCATGTGGCAGCCCATGGGTATGACATAGGCCAAGGCCCAACTAACAGTCAAGAAACAGCTAAAAA
AAAAA

FIG. 20A
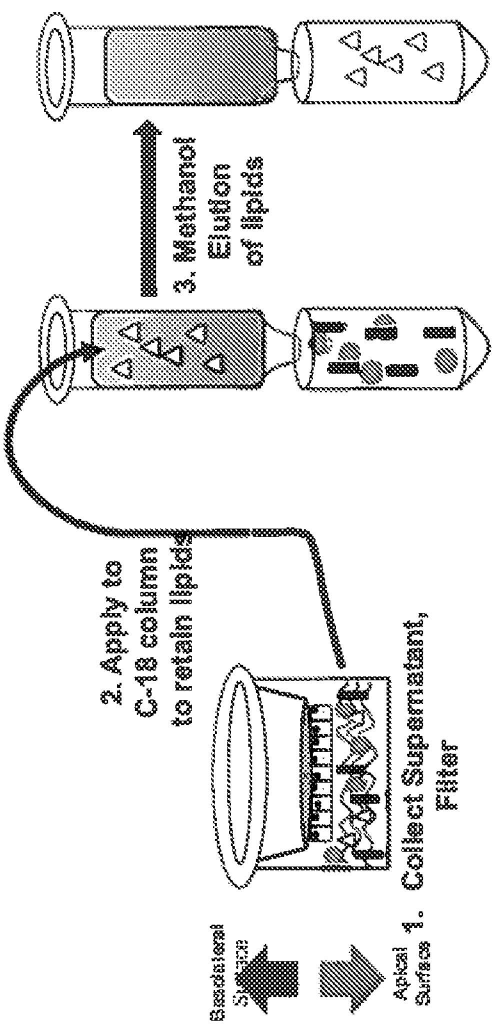
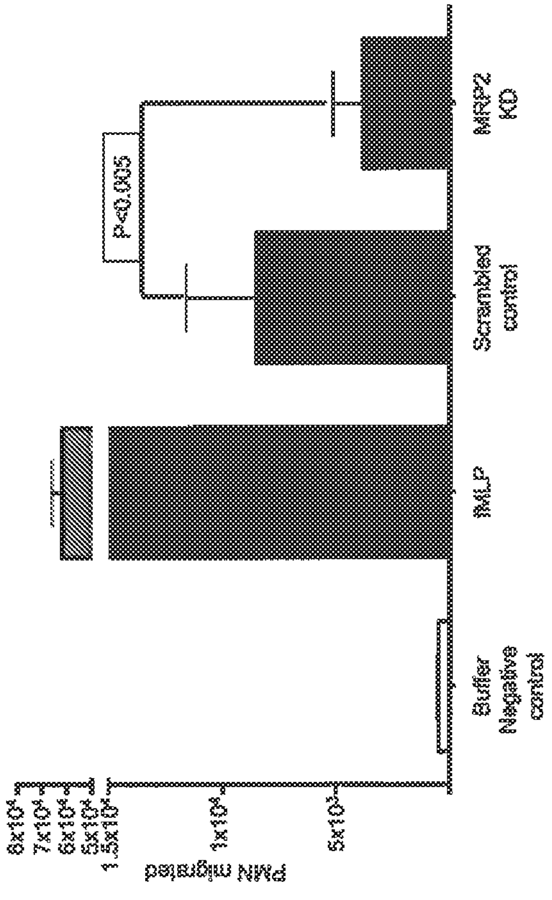
FIG. 20B
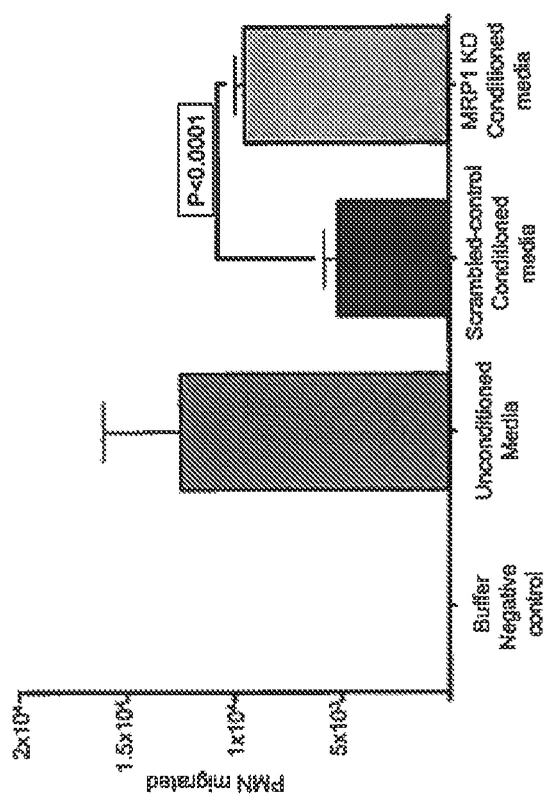
FIG. 20C
Basolateral Surface
Apical Surface
1. Collect Supernatant, Filter
2. Apply to C-18 column to retain lipids
3. Methanol Elution of lipids
PMN migrated
8x10⁴
7x10⁴
6x10⁴
5x10⁴
1.5x10⁴
1x10⁴
5x10³
P<0.005
Buffer Negative control
fMLP
Scrambled control
MRP2 KD
PMN migrated
2x10⁴
1.5x10⁴
1x10⁴
5x10³
P<0.0001
Buffer Negative control
Unconditioned Media
Scrambled-control Conditioned media
MRP1 KD Conditioned media

FIG. 23

Human protein sequence of MRP1, NCBI Reference Sequence: NP_004987.2 (SEQ ID NO:06)

```
1    malrgfcsad gsdplwdwnv twntsnpdft kcfqntvlvw vpcfylwacf pfyflylsrh
61   drgyiqmtpl nktktalgfl lwivcwadlf ysfwersrgi flapvflvsp tllgitmlla
121  tfliqlerrk gvqssgimlt fwlvalvcal ailrskimta lkedaqvdlf rditfyvyfs
181  llliqlvlsc fsdrsplfse tihdpnpcpe ssasflsrit fwwitgliv r gyrqplegsd
241  lwslnkedts eqvvpvlvkn wkkecaktrk qpvkvvyssk dpaqpkessk vdaneeveal
301  ivkspqkewn pslfkvlykt fgpyflmsff fkaihdlmmf sgpqilklli kfvndtkapd
361  wqgyfytvll fvtaclqtlv lhqyfhicfv sgmriktavi gavyrkalvi tnsarksstv
421  geivnlmsvd aqrfmdlaty inmiwsaplq vilalyllwl nlgpsvlagv avmvlmvpvn
481  avmamktkty qvahmkskdn riklmneiln gikvlklyaw elafkdkvla irqeelkvlk
541  ksaylsavgt ftwvctpflv alctfavyvt idennildaq tafvslalfn ilrfplnilp
601  mvissivqas vslkrlrifl sheelepdsi errpvkdggg tnsitvrnat ftwarsdppt
661  lngitfsipe galvavvgqv gcgkssllsa llaemdkveg hvaikgsvay vpqqawiqnd
721  slrenilfgc qleepyyrsv iqacallpdl eilpsgdrte igekgvnlsg gqkqrvslar
781  avysnadiyl fddplsavda hvgkhifenv igpkgmlknk trilvthsms ylpqvdviiv
841  msggkisemg syqellardg afaeflrtya steqeqdaee ngvtgvsgpg keakqmengm
901  lvtdsagkql qrqlssssy sgdisrhhns taelqkaeak keetwklmea dkaqtgqvkl
961  svywdymkai glfisflsif lfmcnhvsal asnywlslwt ddpivngtqe htkvrlsvyg
1021 algisqgiav fgysmavsig gilasrclhv dllhsilrsp msffertpsg nlvnrfskel
1081 dtvdsmipev ikmfmgslfn vigacivill atpiaaiiip plgliyffvq rfyvassrql
1141 krlesvsrsp vyshfnetll gvsvirafee qerfihqsdl kvdenqkayy psivanrwla
1201 vrlecvgnci vlfaalfavi srhslsaglv glsvsyslqv ttylnwlvrm ssemetniva
1261 verlkeyset ekeapwqiqe tappsswpqv grvefrnycl ryredldfvl rhinvtingg
1321 ekvgivgrtg agkssltlgl frinesaege iiidginiak iglhdlrfki tiipqdpvlf
1381 sgslrmnldp fsqysdeevw tslelahlkd fvsalpdkld hecaeggenl svgqrqlvcl
1441 arallrktki lvldeataav dletddliqs tirtqfedct vltiahrlnt imdytrvivl
1501 dkgeiqeyga psdllqqrgl fysmakdagl v
```

METHODS AND COMPOSITIONS FOR TREATING INFLAMMATION

This application is a continuation application of U.S. patent application Ser. No. 16/631,023, filed Nov. 21, 2023, which issued as U.S. Pat. No. 11,865,093 on Jan. 9, 2024, which is the U.S. National stage filing under 35 U.S.C § 371 of, and claims priority to, International Application No. PCT/US2018/042116 filed on Jul. 13, 2018, which claims priority to U.S. Provisional Application Ser. No. 62/532,539, filed Jul. 14, 2017, each of which is herein incorporated by reference.

STATEMENT OF FEDERALLY FUNDED RESEARCH

This invention was made with government support under grant number DK056754 awarded by the National Institutes of Health (NIH). The government has certain rights in the invention.

SEQUENCE LISTING

A Sequence Listing has been submitted in an XML file named "20475," created on Feb. 7, 2024, consisting of 29,602 bytes, the entire content of which is herein incorporated by reference.

TECHNICAL FIELD

The technology of the present disclosure relates to methods for treating neutrophil-mediated inflammation by targeting, in any combination, the pro-inflammatory MRP2/$HXA_3$ pathway and/or the anti-inflammatory P-gp/endocannabinoid pathway and/or the anti-inflammatory MRP1/L-AMEND pathway, comprising administering to the subject a therapeutically effective amount of (a) one or more first compound that inhibits the activity and/or level of one or more of multidrug resistance protein 2 (MRP2) and hepoxilin $A_3$ ($HXA_3$) synthase, and/or (b) one or more second compound that increases the level and/or activity of one or more N-acylethanolamines (NAEs), and/or (c) one or more third compound that increases the level and/or activity of multidrug resistance protein 1 (MRP1), wherein the therapeutic amount of the first, second, and third compounds reduces migration of neutrophils into the target tissue.

BACKGROUND

Inflammation, and in particular chronic inflammatory disease (CID), is globally highly prevalent and is viewed as one of the major causes for the development of different diseases like cancer, cardiovascular disease, diabetes, obesity, osteoporosis, rheumatoid arthritis, inflammatory bowel disease, asthma, and CNS related diseases such as depression and Parkinson's disease. Epithelial cells dramatically increase surface expression of the membrane ABC transporter multidrug resistance protein 2 (MRP2) in response to infection with *Salmonella enterica* serovar *Typhimurium* (*Salmonella typhimurium*) or a variety of other pathogens. The intracellular biosynthetic pathway of the eicosanoid $HXA_3$ is concurrently upregulated, and increased MRP2 at the surface serves to transport $HXA_3$ into the intestinal lumen. This establishes a concentration gradient of $HXA_3$ across the epithelium that directs chemotaxis of neutrophils from the basolateral side into the lumen, resulting in a critical inflammatory process. This MRP/$HXA_3$ pathway is conserved during infection with multiple pathogens in both lung and intestinal epithelia. However, there is no evidence whether it also drives inflammation in the absence of infection.

In parallel with increased MRP2 levels, another ABC transporter, P-glycoprotein (P-gp), is actively reduced at the surface by *Salmonella typhimurium*, the significance of which was previously unclear. Defects in P-gp are linked to inflammatory bowel disease (IBD), with decreased P-gp observed in the epithelium of IBD patients and single-nucleotide polymorphisms in the mdr1 gene encoding P-gp associated with increased risk of IBD. Mice lacking the mdr1a gene that encodes P-gp develop spontaneous intestinal inflammation. However, the mechanisms underlying this process of inflammation are unclear. Thus, there remains a need for compositions and methods that reduce inflammation.

SUMMARY

In one aspect, the present disclosure provides a method for treating neutrophil-mediated inflammation in a target tissue of a mammalian subject in need thereof, comprising administering to the subject a therapeutically effective amount of one or more first compound that inhibits of one or more of multidrug resistance protein 2 (MRP2), and hepoxilin A3 ($HXA_3$) synthase, wherein the therapeutic amount of the first compound reduces migration of neutrophils into the target tissue.

In some embodiments, the method further comprises administering to the subject a therapeutically effective amount of one or more second compound that increases one or more N-acylethanolamines (NAEs), wherein the therapeutic amount of the second compound reduces migration of neutrophils into the target tissue.

In some embodiments, the method further comprises administering to the subject a therapeutically effective amount of one or more third compound that increases multidrug resistance protein 1 (MRP1), wherein the therapeutic amount of the third compound reduces migration of neutrophils into the target tissue.

In some embodiments, the method further comprises administering to the subject a therapeutically effective amount of one or more second compound that increases multidrug resistance protein 1 (MRP1), wherein the therapeutic amount of the second compound reduces migration of neutrophils into the target tissue.

In some embodiments, the administering step is selected from the group consisting of topical administration and administration at a luminal surface of the target tissue.

In some embodiments, the first compound that reduces migration of neutrophils into the target tissue is conjugated to a polymer.

In some embodiments, the inflammation is non-infectious inflammation.

In one aspect, the present disclosure provides a method for treating neutrophil-mediated inflammation in a target tissue of a mammalian subject in need thereof, comprising administering to the subject a therapeutically effective amount of one or more first compound that increases one or more N-acylethanolamines (NAEs), wherein the therapeutic amount of the first compound reduces migration of neutrophils into the target tissue.

In some embodiments, the method further comprises administering to the subject a therapeutically effective amount of one or more second compound that inhibits one or more of multidrug resistance protein 2 (MRP2), and $HXA_3$ synthase, wherein the therapeutic amount of the second compound reduces migration of neutrophils into the target tissue.

In some embodiments, the method further comprises administering to the subject a therapeutically effective amount of one or more third compound that increases multidrug resistance protein 1 (MRP1), wherein the therapeutic amount of the third compound reduces migration of neutrophils into the target tissue.

In some embodiments, the one or more first compound that increases the one or more NAEs is a cannabinoid receptor type 2 (CB2) agonist.

In some embodiments, the first compound that reduces migration of neutrophils into the target tissue is conjugated to a polymer.

In some embodiments, the method further comprises administering to the subject a therapeutically effective amount of one or more second compound that increases multidrug resistance protein 1 (MRP1), wherein the therapeutic amount of the second compound reduces migration of neutrophils into the target tissue In one aspect, the present disclosure provides a method for treating neutrophil-mediated inflammation in a target tissue of a mammalian subject in need thereof, comprising administering to the subject a therapeutically effective amount of one or more first compound that increases multidrug resistance protein 1 (MRP1), wherein the therapeutic amount of the first compound reduces migration of neutrophils into the target tissue.

In some embodiments, the method further comprises administering one or more second compound that inhibits of one or more of multidrug resistance protein 2 (MRP2), and hepoxilin A3 ($HXA_3$) synthase, wherein the therapeutic amount of the second compound reduces migration of neutrophils into the target tissue.

In some embodiments, the method further comprises administering to the subject a therapeutically effective amount of one or more third compound that increases one or more N-acylethanolamines (NAEs), wherein the therapeutic amount of the third compound reduces migration of neutrophils into the target tissue.

In some embodiments, the method further comprises administering to the subject a therapeutically effective amount of one or more second compound that increases one or more N-acylethanolamines (NAEs), wherein the therapeutic amount of the second compound reduces migration of neutrophils into the target tissue.

In some embodiments, the administering is one or more of topical and at a luminal surface of the target tissue.

In some embodiments, the first compound that reduces migration of neutrophils into the target tissue is conjugated to a polymer.

In some embodiments of the methods disclosed herein, the inflammation is non-infectious inflammation. In some embodiments, the inflammation is infectious inflammation.

In some embodiments of the methods disclosed herein, the compound that inhibits MRP2 comprises a probenecid-polymer conjugate having the formula:

(Formula I)

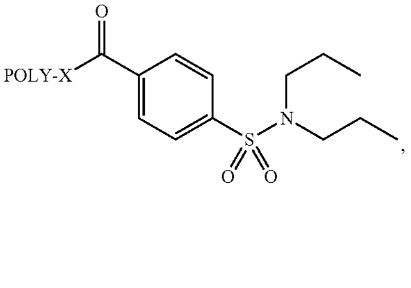

wherein X is a linker comprising one or more atoms and POLY is a polymer.

In some embodiments, X is a linker selected from substituted or unsubstituted $C_1$-$C_X$ alkylene, heteroalkylene, alkenylene, or heteroalkenylene group, wherein x may be any integer from 1 to 12.

In some embodiments, POLY is a polymer selected from the group consisting of: dextran, polyethylene glycol (PEG), periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly (hydroxyalkylmethaacrylamide), polyglycerol, 25 polyamidoamine (PAMAM), polyethylenimine (PEI), polypeptides, and any combination thereof. In some embodiments, POLY is a 40 kDa dextran. In some embodiments, POLY is a 10 kDa dextran. In some embodiments, X is hexylamine and POLY is periodate-oxidized 40 kDa dextran. In some embodiments, POLY is 40 kDa 2-arm branched PEG amine.

In one aspect, the present disclosure provides a compound having the formula:

(Formula I)

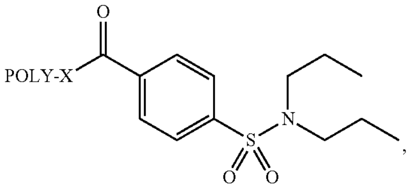

wherein X is a linker and POLY is a polymer.

In some embodiments, X is a linker selected from substituted or unsubstituted $C_1$-$C_X$ alkylene, cycloakylene, cycloalkylalkylene, heteroalkylene, alkenylene, or heteroalkenylene group, wherein x may be any integer from 1 to 12.

In some embodiments, POLY is a polymer selected from the group consisting of: dextran, polyethylene glycol (PEG), periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly (hydroxyalkylmethaacrylamide), polyglycerol, 25 polyamidoamine (PAMAM), polyethylenimine (PEI), polypeptides, and any combination thereof. In some embodiments, POLY is a 40 kDa dextran. In some embodiments, X is hexylamine and POLY is periodate-oxidized 40 kDa dextran. In some embodiments, POLY is a 10 kDa dextran.

In some embodiments, X is a linker selected from substituted or unsubstituted $C_1$-$C_X$ alkylene, cycloakylene, cycloalkylalkylene, heteroalkylene, alkenylene, or heteroalkenylene group, wherein x may be any integer from 1 to 12, and POLY is periodate-oxidized 10 kDa dextran.

In some embodiments, POLY is PEG. In some embodiments, POLY is 40 kDa 2-arm branched PEG amine.

In some embodiments, the compound of the present disclosure is capable of reducing neutrophil-mediated inflammation in a subject in need thereof relative to an untreated control.

In some embodiments, the present disclosure relates to a pharmaceutical composition comprising a therapeutically effective amount of the compound of Formula I and a pharmaceutically acceptable carrier.

In some embodiments, the present disclosure relates to a method for treating or preventing inflammation in a subject in need thereof, comprising administering to the subject a therapeutically effective amount of the compound of Formula I.

In some embodiments, the inflammation results from an inflammatory condition selected from the group consisting of: intestinal disease, including proctitis, orchitis, Crohn's disease, colitis, such as ulcerative colitis, also known as colitis ulcerosa, infectious/non-infectious enterocolitis, and inflammatory bowel disease (IBD); inflammatory lung conditions, including pneumococcal infection, asthma, chronic obstructive pulmonary disease (COPD), and pulmonary fibrosis; inflammatory skin diseases, including dermatitis (eczema), rosacea, seborrheic dermatitis, and psoriasis; ocular disease, such as uveitis, retinitis, keratitis, and macular degeneration; urogenital disease, including urinary tract infection; sexually transmitted diseases, including pelvic inflammatory disease, gonorrhea infection, chlamydia infection, and herpes; and urethritis.

In some embodiments, the inflammation comprises neutrophil-mediated inflammation.

In some embodiments, the administering comprises contacting an epithelial cell with an effective amount of the compound.

In some embodiments, the treatment reduces the number of neutrophils migrating in a basolateral-to-apical direction.

In some embodiments, the inflammation is associated with inflammatory bowel disease (IBD), ulcerative colitis (UC), Crohn's disease (CD), or infectious and/or non-infectious enterocolitis.

In some embodiments, the inflammation is associated with Crohn's disease and the treatment or prevention further comprises administering one or more mesalamine products, corticosteroid formulations, ileal-release budesonide, glucocorticosteroids/EEN immunomodulatives, including azathioprine, 6-mercaptopurine, and methotrexate, anti-tumor necrosis factor (TNF) drugs, including infliximab, adalimumab, and certolizumab, pegol, anti-alpha-4 beta-7 integrin antibody vedolizumab, ABT-494, and filgotinib.

In some embodiments, the inflammation is associated with ulcerative colitis and the treatment or prevention further comprises administering one or more of 5-aminosalycylates, mesalamine, corticosteroids, multimatrix budesonide, azathioprine, 6-mercaptopurine, anti-TNF drugs, including infliximab, adalimumab, and golimumab, vedolizumab, tofacitinib, ABT-494, and filgotinib.

In some embodiments, the inflammation is associated with an infectious and/or non-infectious inflammatory lung condition selected from the group consisting of: pneumococcal infection, asthma, chronic obstructive pulmonary disease (COPD), and pulmonary fibrosis.

In some embodiments, the inflammation is associated with inflammatory skin disease selected from the group consisting of: dermatitis (eczema), rosacea, seborrheic dermatitis, and psoriasis.

In some embodiments, the method further comprises administering one or more antibiotic and/or anti-inflammatory agents selected from the group consisting of: Dalbavancin, Oritavancin, Cubicin, Tedizolid, Ceftobiprole, Ceftobiprole, Ceftolozane-tazobactam, mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluorometha-lone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppresant agents such as cyclosporin, and cytokine synthesis inhibitors, tetracycline, minocycline, and doxycycline, or any combination thereof.

In some embodiments, the method further comprises administering one or more antibodies selected from the group consisting of: antibodies targeting *Clostridium difficile* toxins, antibodies targeting tumor necrosis factor (TNF), antibodies targeting interleukins, and antibodies targeting metalloproteinase-9.

BRIEF DESCRIPTION OF THE DRAWINGS

FIGS. 1A-1I. $HXA_3$ drives inflammation during DSS colitis. Mucosal scrapings from mice treated with 5% DSS for 7 days were enriched for lipids and the amount of $HXA_3$ quantified by LC/MS/MS (FIG. 1A). C57BL/6 mice were treated with 3% DSS for 7 days and sacrificed at day 9 (FIGS. 1B-1I). Starting at day 4, daily rectal administration was performed of PBS control (vehicle) or probenecid conjugate. All data are mean+/−S.E.M., n=10 mice per group, statistical significance by Mann-Whitney one-tailed nonparametric U test. Paraffin-embedded sections of mid and distal colon were stained for H&E and scored by a trained investigator blinded to sample identity (FIGS. 1C and 1D). Arrows highlight accumulation of neutrophils in intestinal lumen (FIG. 1D). Myeloperoxidase (mpo) activity was measured by ADHP assay over 8 min (see methods) from feces (FIG. 1E) or colonic tissue (FIG. 1F) and slopes calculated by linear regression. For tissue, slopes were normalized to total protein content. Total lamina propria leukocytes were isolated and stained for flow cytometry (FIGS. 1G-1I). Neutrophils were characterized as Live/CD45+/CD11bhi/Ly6G+. FIG. 1G shows the percent neutrophils; FIG. 1H shows the number of neutrophils; and FIG. 1I shows representative plots of neutrophils in colon tissue.

FIG. 2B performed as in FIG. 2A, with supernatants from cell lines expressing different shRNA constructs to knock down P-gp expression (B4-mdr1 and B5-mdr1). FIG. 2C performed as in FIG. 2A, but prior to use in the migration assays enriched T84 supernatants were pretreated with FAAH or MAGL at 37° C. for 30 min. T84 monolayers were treated with vehicle or verapamil to inhibit P-gp function, followed by supernatant collection and lipid enrichment. Preparations were separated by HPLC, oval highlights peak that is absent in verapamil-treated cells (FIG. 2D). Enriched T84 supernatants from control or B4-mdr1 knockdown cell lines were subjected to electrospray ionization mass spectrometry. Arrow indicates peak of anandamide Na+ adduct (FIG. 2E). Commercially available endocannabinoids and related compounds were tested in the 96 well migration assay (FIG. 2F). Compounds were used at the highest concentration at which they were soluble in PBS. Data are mean+/−SEM of at least 3 independent experiments, *=p<0.05 and =p<0.01 by one-way ANOVA. See Methods for more information FIGS. 3A and 3B. AMEND is present in mouse intestine. Colonic scrapings from 5 wild-type (wt) or mdr1a−/− mice were pooled, enriched for lipids and tested in the 96-well migration assay as in FIG. 2A. Data are mean+/−SEM from three independent experiments, =p<0.01 by one-way ANOVA.

FIGS. 4B and 4C: Histopathology of mid and distal colon as in FIG. 1. Arrows highlight accumulation of neutrophils in intestinal lumen (FIG. 4C). Tissue mpo activity, n=13 wt and 11 cnr2−/− mice (FIG. 4E). Fecal mpo activity, n=14 wt and 12 cnr2−/− mice (FIG. 4D). Number (FIG. 4F) and percentage (FIG. 4G) of tissue neutrophils by flow cytometry analysis. Representative plots of lamina propria neutrophils (FIG. 4H). FIGS. 4F-4H: n=13 wt and 12 cnr2−/− mice.

FIG. 12. *Homo sapiens* ATP binding cassette subfamily C member 2 (ABCC2), mRNA>gi|594191052|ref|NM_000392.4| (SEQ ID NO: 02).

FIG. 13. *Homo sapiens* ATP-binding cassette, sub-family B (MDR/TAP), member 1 (ABCB1), mRNA>gi|318037598|ref|NM_000927.4| (SEQ ID NO: 03).

FIG. 14. Rat ALOX15: *Rattus norvegicus* arachidonate 15-lipoxygenase (Alox15), mRNA>gi|31542124|ref|NM_031010.2| (SEQ ID NO: 04).

FIG. 15. Human FAAH: *Homo sapiens* fatty acid amide hydrolase (FAAH), mRNA>gi|166795286|ref|NM_001441.2| (SEQ ID NO: 05).

In FIG. 17A, red boxed regions represent the region of interest on the apical surface of the cell monolayer. F-actin was used to examine cellular borders and localize the apical surface. The percentage of the area taken up by the protein expression of the given gene via calculations completed in Fiji was determined. Shown in FIG. 17A are the MRP2 and F-actin sections of uninfected and *Streptococcus pneumoniae* H292 cells. The process was repeated for MRP1, MRP4, and MRP5 (FIG. 17B). When uninfected to infected samples are compared, *S. pneumoniae* infection decreases MRP1 surface expression, increases MRP2 surface expression, but has no effect on MRP4 or MRP5, confirming the biotinylation data of FIG. 1. (n=8 per sample).

FIGS. 20A-20D. Secreted supernatants confer anti-inflammatory (MRP1) or inflammatory (MRP2) phenotype. Pro-inflammatory lipids (represented by triangles in FIG. 20A) were isolated by pooling the apical supernatants from infected H292 monolayers. This was applied to C-18 columns and eluted in methanol for storage (FIG. 20A). Methanol was evaporated under a constant stream of nitrogen and resuspended in HBSS to be used as neutrophil chemoattractant. Shown are the numbers of neutrophils that migrate from the basolateral-to-apical chamber of an H292 monolayer to the stimuli indicated. Lipid extracts were isolated from either scrambled control or MRP2 knockdown cells and applied to the apical chamber of naïve H292 cells (FIG. 20B). Lipids from MRP2 knockdown cells showed reduced neutrophil migration as compared to scrambled control, implying MRP2 effluxes pro-inflammatory stimuli. fMLP acted as a positive control. HBSS+ was applied to the apical surface of scrambled control cells or MRP1 knockdown cells to produce conditioned media (FIG. 20C). Proinflammatory lipids were resuspended with unconditioned media, conditioned media from scrambled control, or conditioned media from MRP1 knockdown cells (MRP1 KD). Unconditioned media promoted the maximal amount of neutrophil migration; scrambled control cells with intact MRP1 showed a reduced number of neutrophils; MRP1 knockdown cells induced an equivalent number of neutrophil as the unconditioned media, indicating MRP1 likely assists in a neutrophil-inhibition activity. In a similar model utilizing bacterial infection in lieu of proinflammatory lipids, the MRP2 inhibitor Probenecid (100 μM) reduces neutrophil migration with approximately the same efficiency (FIG. 20D).

FIG. 23. Human protein sequence of MRP1, NCBI Reference Sequence: NP_004987.2 (SEQ ID NO: 06).

DETAILED DESCRIPTION

I. Definitions

Figure 1A:
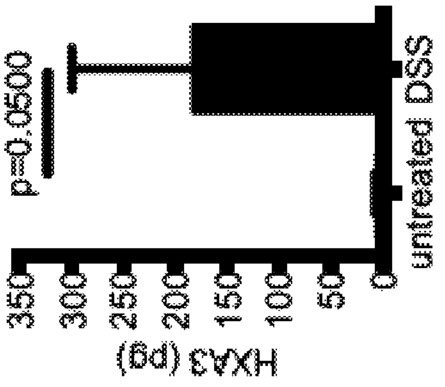

The following terms are used herein, the definitions of which are provided for guidance.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. It will be understood by those of skill in the art that substituted groups of the present technology are chemically stable groups that allow isolation of the compounds in which they appear. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; sulfonamides; amines; N-oxides; azides; amides; ureas; amidines; guanidines; nitro groups; nitriles (i.e., CN); and the like.

Alkyl groups include straight chain and branched chain alkyl groups having (unless indicated otherwise) from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like. In some embodiments the alkyl group is substituted with 1, 2, or 3 substituents.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, $-CH=CH(CH_3)$, $-CH=C(CH_3)_2$, $-C(CH_3)=CH_2$, $-C(CH_3)=CH(CH_3)$, $-C(CH_2CH_3)=CH_2$, among others. Representative substituted alkenyl groups may be mono-substituted or substituted more than once, such as, but not limited to, mono-, di- or tri-substituted with substituents such as those listed above.

Heteroalkyl groups and heteroalkenyl groups are, respectively, alkyl groups (as defined herein) and alkenyl groups (as defined herein) that include from 1 to 6 heteroatoms selected from N, O and S. It will be understood that each heteroatom present is bonded to at least one carbon atom within the heteroalkyl or heteroalkenyl group. In some embodiments the heteroaklyl or heteteroalkenyl groups include 1, 2, or 3 heteroatoms. Heteroalkyl and heteroalkenyl groups may be substituted or unsubstituted. Examples of heteroalkyl groups include but are not limited to $CH_3CH_2OCH_2$, $CH_3NHCH_2$, $CH_3CH_2N(CH_3)CH_2$, $CH_3CH_2SCH_2$, $CH_3CH_2OCH_2CH_2OCH_2CH_2$. Examples of heteroalkenyl groups include but are not limited to $CH_2$—$CHOCH_2$, $CH_2=CHN(CH_3)CH_2$, and $CH_2=CHSCH_2$. Representative substituted heteroalkyl or heteroalkeneyl groups may be substituted one or more times with substituents such as those listed above (e.g., 1, 2 or 3 times), and include without limitation haloheteroalkyl (e.g., trifluoromethyloxyethyl), carboxyalkylaminoalkyl, methyl acrylate and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1]hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent cycloalkyl groups are cycloalkylene groups, divalent heteroalkyl groups are heteroalkylene groups, divalent alkenyl groups are alkenylene groups, and so forth. Substituted groups having a single point of attachment to the compound of the present technology are not referred to with the "ene" designation. Thus, e.g., chloroethyl is not referred to herein as chloroethylene.

The term "administering" a molecule to a subject means delivering the molecule to the subject. "Administering" includes prophylactic administration of the composition (i.e., before the disease and/or one or more symptoms of the disease are detectable) and/or therapeutic administration of the composition (i.e., after the disease and/or one or more symptoms of the disease are detectable). The methods of the present technology include administering one or more compounds. If more than one compound is to be administered, the compounds may be administered together at substantially the same time, and/or administered at different times in any order. Also, the compounds of the present technology may be administered before, concomitantly with, and/or after administration of another type of drug or therapeutic procedure (e.g., surgery).

The terms "alter" and "modify" when in reference to the level of any molecule (e.g., multidrug resistance protein 2 (MRP2), multidrug resistance protein 1 (MRP1), hepoxilin A3 ($HXA_3$) synthase, N-acyl ethanolamine (NAE), amino acid sequence, nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 ($HXA_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), refer to an increase and/or decrease.

"Cannabinoid receptor type 2" ("CB2") is a G protein-coupled receptor from the cannabinoid receptor family that in humans is encoded by the CNR2 gene. The principal endogenous ligand for the CB2 receptor is 2-arachidonoylglycerol (2-AG).

The term "conjugating," and grammatical equivalents, when made in reference to conjugating a molecule of interest and a polymer means covalently linking the molecule of interest to the polymer. Linkage may be direct. Alternatively, linkage may be indirect via a linking group or moiety. Methods for conjugation to polymers are known in the art, including methods for conjugation to a polypeptide to produce a fusion protein (Pasut, *Polymers* 6:160-178

(2014); Medscape, *Nanomedicine* 5(6):915-935 (2010)). In some embodiments, the conjugate is exemplified by the chemically conjugated probenecid to periodate-oxidized 40 kDa dextran (Example 3) via a linking group, diamino hexane.

As used herein, the terms “effective amount” or “therapeutically effective amount,” or “pharmaceutically effective amount” refer to a quantity sufficient to achieve a desired therapeutic and/or prophylactic effect, e.g., an amount which results in the full or partial amelioration of inflammation (e.g., inflammation associated with neutrophil migration into a target tissue) or disease or disorders or symptoms associated with inflammation in a subject in need thereof. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds. In some embodiments, multiple doses are administered. Additionally or alternatively, in some embodiments, multiple therapeutic compositions or compounds are administered. In the methods described herein, the therapeutic compounds may be administered to a subject having one or more signs or symptoms of a disease or disorder associated with inflammation (e.g., inflammation associated with increased neutrophil migration into a tissue).

Figures 2A, 2B, 2C, 2D, 2E:
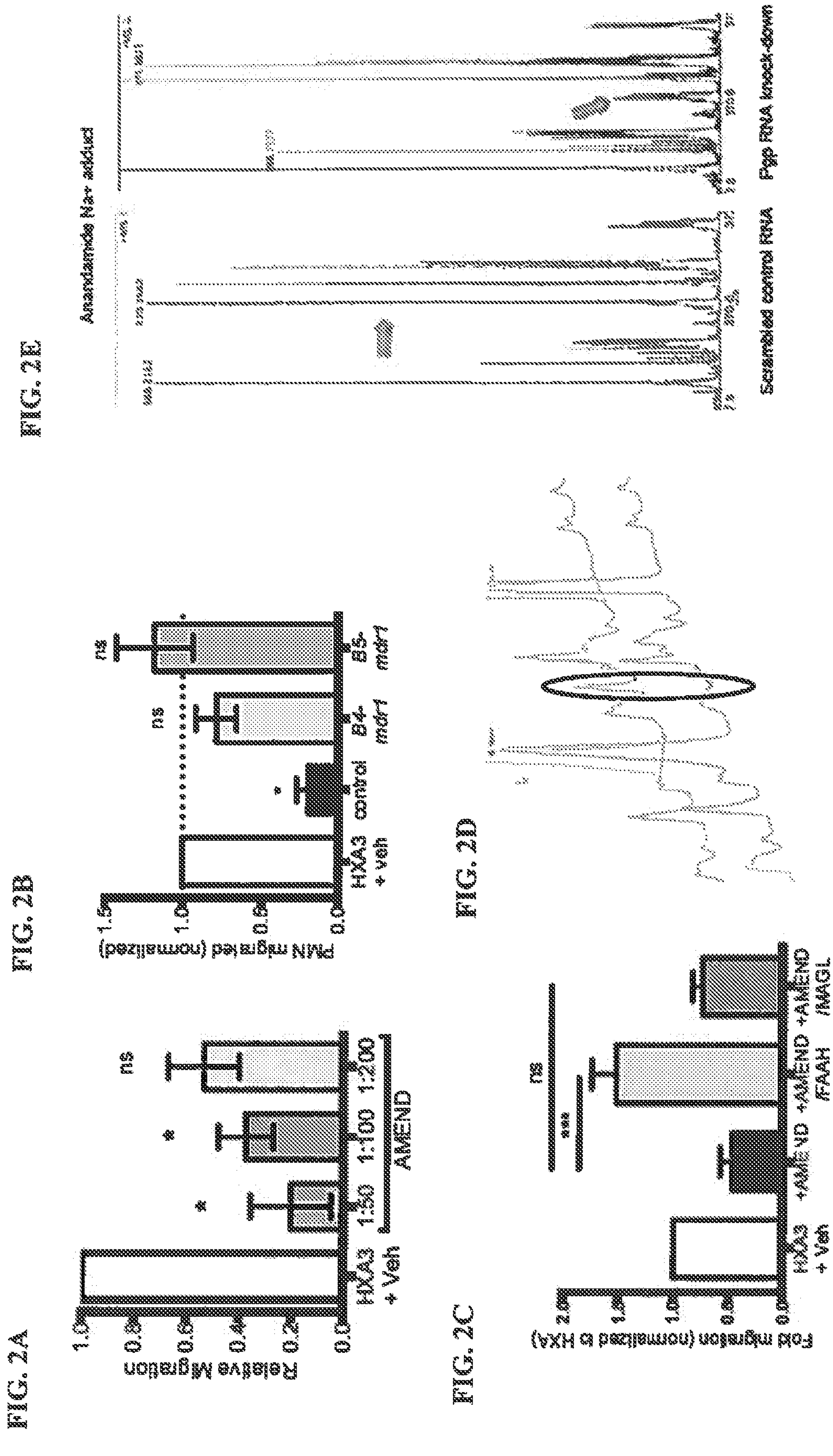
FIGS. 2A-2F. Epithelial cells secrete P-gp dependent endocannabinoids that inhibit neutrophil migration. Supernatants from T84 epithelial monolayers were enriched for lipids and tested for ability to inhibit $HXA_3$-induced migration in a 96-well modified Boyden chamber assay (FIG. 2A). In order to compare across experiments with different donors, migration values within individual experiments were normalized to enriched $HXA_3$ with vehicle treatment. For FIGS. 2A-2C, data are mean ratios+/−S.E.M. of 3 independent experiments, *=$p<0.05$ by one-way ANOVA.
Figure 2F:
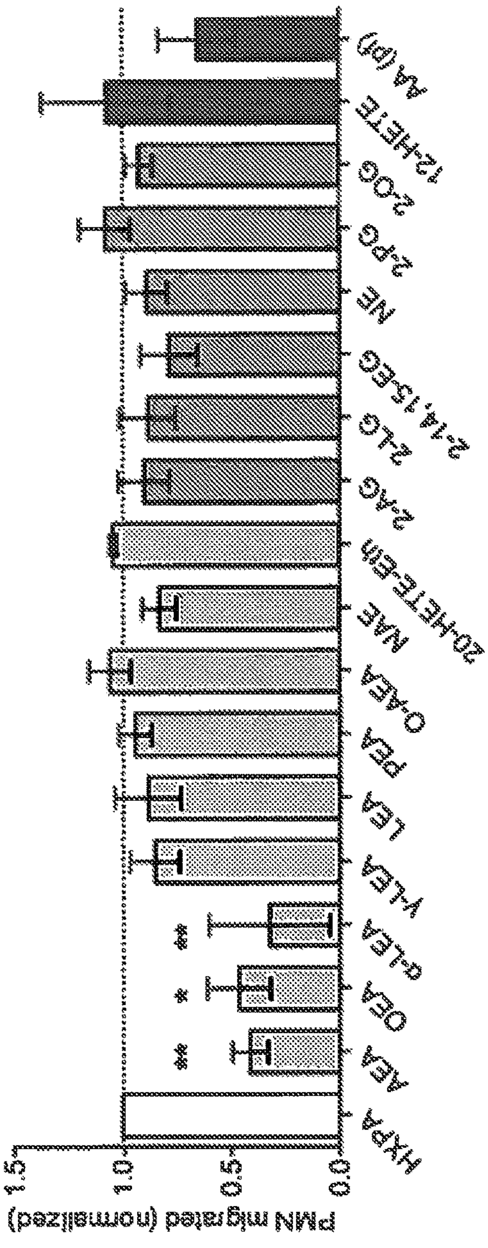

“Endocannabinoids” (“ECs”) are compounds that bind to the cannabinoid receptors, CB1 and CB2, as well as more recently described atypical receptors GPR55 and GPR119. The two main classes of eicosanoid-type ECs are “N-acylethanolamines” (“NAEs”) and monoacylglycerols (MAGs), which are metabolized by fatty acid amide hydrolase (FAAH) and monoacyl glycerol lipase (MAGL), respectively. “N-acylethanolamine” is an endocannabinod and is a type of fatty acid amide formed when one of several types of acyl group is linked to the nitrogen atom of ethanolamine. N-acylethanolamines are metabolized by fatty acid amide hydrolase (FAAH). Exemplary N-acylethanolamine endocannabinoids include ethanolamine, anandamide (AEA) (N-arachidonoylethanolamine), which is the amide of arachidonic acid (20:4 ω-6) (FIG. 2E), oleoyl ethanolamide (OEA), and alpha-linolenoyl ethanolamide (α-LEA) (FIG. 2F).

“Epithelial tissue” contains epithelial cells, i.e., a polarized cell type featuring distinct apical, lateral and basal plasma membrane regions/domains. Epithelial cells connect to one another via their lateral membranes to form epithelial sheets that line cavities and surfaces throughout the animal body. Each plasma membrane domain has a distinct protein composition, giving them distinct properties and allowing directional transport of molecules across the epithelial sheet. The “apical” region of an epithelial cell is defined as the area lying above the tight junctions and contains the apical membrane which faces the lumen or the outer surface of the tissue. The “basolateral” region of an epithelial cell is the side that is below the tight junctions and contains the basolateral membrane which is in contact with the basal lamina.

“Fatty acid amide hydrolase,” “FAAH,” and “EC 3.5.1.99” interchangeably refer to a member of the serine hydrolase family of enzymes. It was first shown to break down anandamide. In humans, it is encoded by the gene FAAH and is exemplified by human FAAH encoded by mRNA SEQ ID NO: 05 (FIG. 15).

Figure 11:
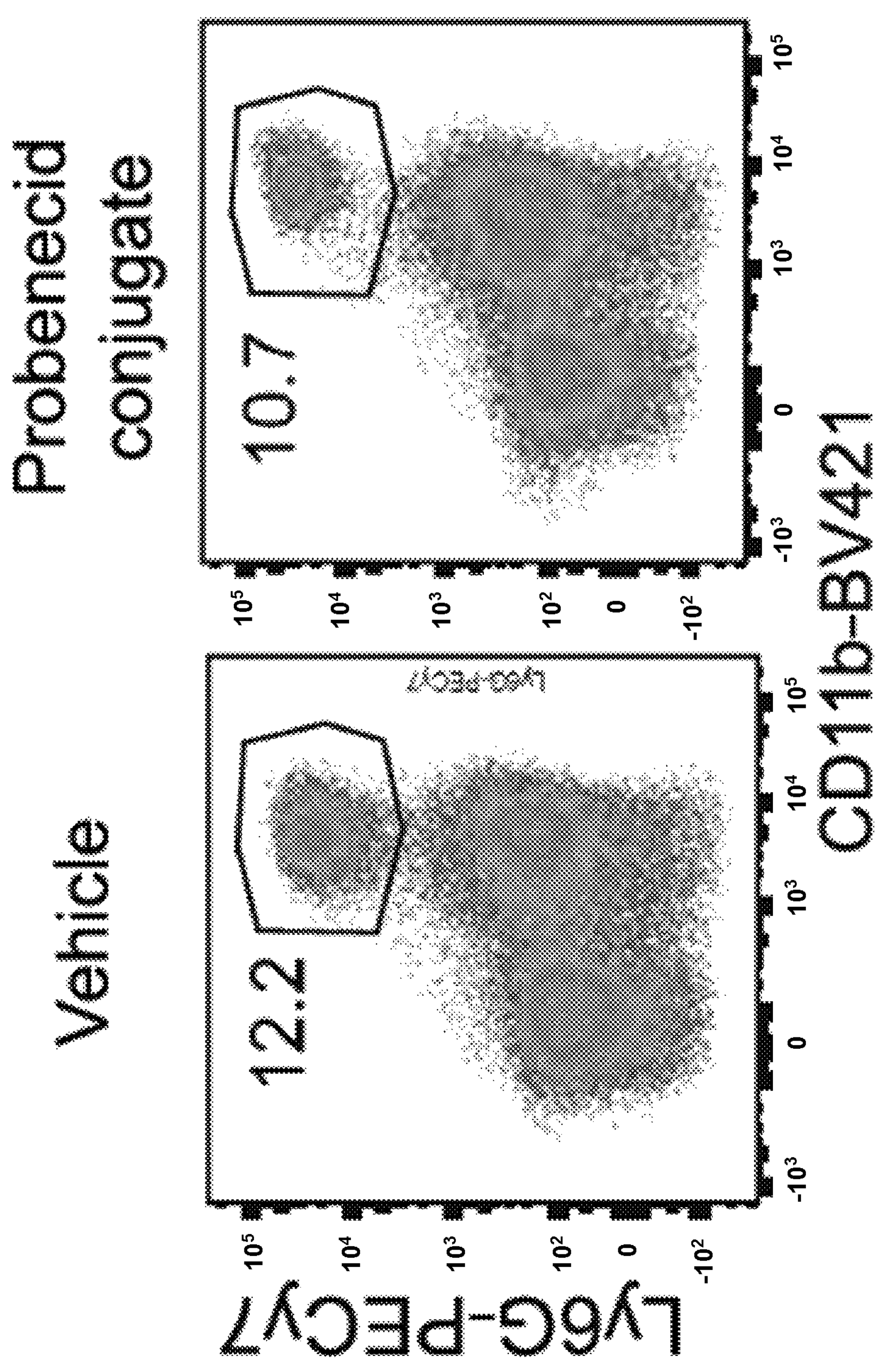
FIG. 11. Human 12-lipoxygenase (Alox12) mRNA, complete cds, gi|187170|gb|M58704.1|HUMLIPXYG (SEQ ID NO: 01).

“Hepoxilin A3 synthase,” “$HXA_3$ synthase,” “ALOX12,” “12-lipoxygenase,” “arachidonate 12-lipoxygenase,” “12S-Lipoxygenase,” “12-LOX,” and “12S-LOX” interchangeably refer to a lipoxygenase-type enzyme (i.e., an enzyme that catalyzes the dioxygenation of polyunsaturated fatty acids in lipids containing a cis,cis-1,4-pentadiene structure) that in humans is encoded by the ALOX12 gene, which is located along with other lipoyxgenases on chromosome 17p13.3. Alox12 is exemplified by human Alox12 encoded by mRNA SEQ ID NO: 01 (FIG. 11). Alox12 is also exemplified by rat Alox15, which converts arachidonic acid to 15S-hydroperoxyeicosatetraenoic acid and acts on C-12 of arachidonate as well as on linoleic acid. Rat Alox15 is encoded by mRNA SEQ ID NO: 04 (FIG. 14).

The term “increase” when in reference to a compound e.g., N-acylethanolamine, means increase the level and/or activity of N-acylethanolamine. The terms “increase,” “elevate,” “raise,” and grammatical equivalents (including “higher,” “greater,” etc.) when in reference to the level of any molecule (e.g., multidrug resistance protein 2 (MRP2), multidrug resistance protein 1 (MRP1), hepoxilin A3 ($HXA_3$) synthase, N-acyl ethanolamine (NAE), amino acid sequence, and nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 ($HXA_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first sample (or the first subject) is exemplified by, but not limited to, a sample (or subject) that has been manipulated using the compositions and/or methods of the present technology. In a further embodiment, the second sample (or the second subject) is exemplified by, but not limited to, a sample (or subject) that has not been manipulated using the compositions and/or methods of the present technology. In an alternative embodiment, the second sample (or the second subject) is exemplified by, but not limited to, a sample (or subject) that has been manipulated, using the compositions and/or methods of the present technology, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the compositions and/or methods of the present technology is sought to be determined on one sample (or subject). In another embodiment, the first and second samples (or subjects) may be different, such as when comparing the effect of the compositions and/or methods of the present technology on one sample (subject), for example a patient participating in a clinical trial and another individual in a hospital.

The term "inhibit" when used in reference to a compound, e.g., multidrug resistance protein 2 (MRP2), hepoxilin A3 ($HXA_3$) synthase, etc., means inhibit the activity and/or level of $HXA_3$. The terms "inhibit," "reduce," "diminish," "suppress," "decrease," and grammatical equivalents (including "lower," "smaller," etc.) when in reference to the level of any molecule (e.g., multidrug resistance protein 2 (MRP2), multidrug resistance protein 1 (MRP1), hepoxilin A3 ($HXA_3$) synthase, N-acyl ethanolamine (NAE), amino acid sequence, and nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 ($HXA_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) in a first sample (or in a first subject) relative to a second sample (or relative to a second subject), mean that the quantity of molecule, cell, and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first sample (or the first subject) is exemplified by, but not limited to, a sample (or subject) that has been manipulated using the compositions and/or methods of the present technology. In a further embodiment, the second sample (or the second subject) is exemplified by, but not limited to, a sample (or subject) that has not been manipulated using the compositions and/or methods of the present technology. In an alternative embodiment, the second sample (or the second subject) is exemplified by, but not limited to, a sample (or subject) that has been manipulated, using the compositions and/or methods of the present technology, at a different dosage and/or for a different duration and/or via a different route of administration compared to the first subject. In one embodiment, the first and second samples (or subjects) may be the same, such as where the effect of different regimens (e.g., of dosages, duration, route of administration, etc.) of the compositions and/or methods of the present technology is sought to be determined on one sample (or subject). In another embodiment, the first and second samples (or subjects) may be different, such as when comparing the effect of the compositions and/or methods of the present technology on one sample (subject), for example a patient participating in a clinical trial and another individual in a hospital.

"Mucosal tissue" refers to a mucous tissue that lines various tubular structures. Mucosal tissue includes epithelium, lamina propria, and, in the digestive tract, a layer of smooth muscle (muscularis mucosae).

"Multidrug resistance-associated protein 2," "multidrug resistance protein 2" ("MRP2"), "canalicular multispecific organic anion transporter 1" ("cMOAT"), "ATP-binding cassette sub-family C member 2" ("ABCC2") are interchangeably used to refer to protein that in humans is encoded by the ABCC2 gene. MRP2 is exemplified by human MRP2 encoded by mRNA SEQ ID NO:02 (FIG. 12).

"Multidrug resistance protein 1," "MRP1" and "ABCC1" are interchangeably used to refer to a uni-directional efflux transporter protein with a wide substrate specificity including important therapeutics. Some of the main roles of this transporter are: (i) efflux of xenobiotic and endogenous metabolites; (ii) transport of inflammatory mediators (e.g., LTC4); and (iii) defense against oxidative stress. The 190-kDa MRP1 has a core structure consisting of two transmembrane domains (TMD), each followed by a nucleotide binding domain (NBD). In common with MRP2, 3, 6, and 7, MRP1 contains a third TMD (TMDO) with five predicted trans membrane segments and an extra cytosolic $NH_2$ terminus connected to the core structure by a linker region (L0) (Rosenberg et al., *J. Biol. Chem.* 276(19):13076-16082 (2001)). The TMDO appears to be important for MRP1 trafficking to the plasma membrane (Bakos et al., *J. Cell Sci.* 113 (Pt 24):4451-4461 (2000)), and the precise roles, mechanisms, and dependencies of TMDO and L0 are the subject of significant research (Westlake et al. *Mol. Biol. Cell* 16(5):2483-2492 (2005)). MRP1 has broad substrate specificity, transporting hydrophobic and anionic molecules, glucuronide and glutathione conjugates, as well as endogenous glutathione. Although many MRP1 substrates are conjugated to glutathione, co-transport of free glutathione is often observed, and appears to stimulate transport of e.g., vincristine and daunorubicin (Hooijberga et al., *FEBS Letters* 469:47-51(2000)). Glutathione itself is a low affinity substrate of MRP1 (Km=1-5 mM). Multiple allosterically cooperative, non-overlapping substrate-binding sites are postulated, which may explain why various substrates both cross-inhibit and cross-stimulate (Bakos et al., *Pflugers Arch—Eur J Physiol* 453:621-641(2007)). The inflammatory cytokine LTC4 and its main metabolite LTD4 are some of the highest affinity MRP1 substrates, suggesting a key role for MRP1 in cytokine release from LTC4 producing cells. In fact, intracellular LTC4 accumulation was observed in mrp1 (−/−) mice (Robbiani et al., *Cell* 103:757-768 (2000)). Additionally, although viable, healthy, and fertile with normal phenotype, knockout mrp1 (−/−) mice were hypersensitive to cytotoxic drugs (Wijnholds et al., *Nat. Med.* 3:1275-1279 (1997)). MRP1 is exemplified by the human protein sequence NCBI Reference Sequence: NP_004987.2 (SEQ ID NO: 06) (FIG. 23) encoded by the DNA sequence NCBI Reference Sequence: NG_028268.1. There are at least 15 naturally occurring mutations identified in MRP1, and many of them have been found to affect its in vitro transport activity. Polymorphisms and mutagenesis studies have been reviewed in He et al., *Curr. Med. Chem.* 18:439-481 (2011). Although many MRP1 SNPs are known, their incidence in populations is reported to be relatively low. In mainland Chinese populations the MRP1 polymorphism allelic frequencies of Cys43Ser (128G>C), Thr73Ile (218C>T), Arg723Gln (2168G>A) and Arg1058Gln (3173G>A) were 0.5%, 1.4%, 5.8% and 0.5%, respectively (Ji-Ye Yin et al., *Pharmacogenet. Genomics* 19(3):206-216 (2009)).

"P-glycoprotein" ("P-gp") is an efflux membrane transporter, and is responsible for limiting cellular uptake and the distribution of xenobiotics and toxic substances. P-gp is exemplified by human P-gp encoded by mRNA SEQ ID NO: 03 (FIG. 13).

"Polymer" is a substance that has a molecular structure consisting chiefly or entirely of a large number of similar units bonded together. Polymers may occur naturally (e.g., cellulose, polypeptides, nucleotides sequences, etc.) or are artificial (e.g., plastics, resins, etc.). Polymers may be used as carriers of drugs to which they are conjugated, and may enhance the solubility of the conjugated drug, improve its pharmacokinetic profile, protect the drug against degradation, release the drug under certain conditions, such as change in pH or in the presence of enzymes, such as esterases, lipases or proteases. In addition, a targeting moiety or a solubilzer may also be introduced into the conjugate to boost its therapeutic index (Medscape, Nanomedicine 5(6):915-935(2010)). Polymers may also be utilized to restrict the distribution of the drug conjugated to it by, for example, preventing the conjugated drug from crossing into specific body compartments (e.g., from the gastrointestinal lumen to the underlying tissue). Polymers may be natural polymers and/or synthetic linear polymers, and include polyethylene glycol (PEG), dextran, periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly(hydroxyalkylmethaacrylamide), polyglycerol, 25 polyamidoamine (PAMAM), polyethylenimine (PEI), and polypeptides. In some embodiments, the polymer is periodate-oxidized 40 dextran, exemplified by the chemically conjugated probenecid to periodate-oxidized 40 kDa dextran (Example 3).

"SipA" and "*Salmonella* T3SS effector protein" are used interchangeably to refer to a protein produced by *Salmonella*, as exemplified by the amino acid sequence of *Salmonella enterica* subsp. *enterica* serovar *Typhimurium* str. SL1344 (GenBank: AAA86618.1) encoded by the DNA sequence (Locus taq) SL1344_2861 of the *Salmonella enterica* subsp. *enterica* serovar *Typhimurium* str. SL1344, complete genome sequence (NCBI Reference Sequence: NC_016810.1). The SipA sequence is provided by WO 2015/089268.

"Target tissue" that may suffer from inflammation includes, without limitation, epithelial tissue, mucosal tissue, etc. Exemplary epithelial tissue and/or mucosal tissue include gastrointestinal, lung (e.g., bronchial tissue), liver, stomach, colon, brain, gallbladder, renal, female genital tract, ocular, urinary tract, etc., resulting in "inflammatory diseases" such as intestinal disease (exemplified by proctitis, orchitis, Crohn's disease, colitis (such as ulcerative colitis, also known as colitis ulcerosa), infectious/non-infectious enterocolitis, inflammatory bowel disease (IBD), etc.), inflammatory lung conditions (such as pneumococcal infection, asthma, chronic obstructive pulmonary disease (COPD), and pulmonary fibrosis), inflammatory skin diseases (such as dermatitis (eczema), rosacea, seborrheic dermatitis, and psoriasis), ocular disease (exemplified by uveitis, retinitis, keratitis, macular degeneration, etc.), urogenital disease (such as urinary tract infection), sexually transmitted diseases (such as pelvic inflammatory disease that includes inflammatory disease exemplified by gonorrhea infection and/or chlamydia infection, and by ulceration disease exemplified by herpes), urethritis, etc. As used herein, "target tissue" also encompasses an anatomic space, e.g., the intestinal lumen.

"Treating," "treat," "treated," or "treatment" as used herein covers the treatment of a disease or disorder described herein (e.g., inflammation), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. Symptoms may be assessed by methods known in the art, for example, biopsy and histology, and blood tests to determine relevant enzyme levels, metabolites or circulating antigen or antibody (or other biomarkers), quality of life questionnaires, patient-reported symptom scores, and imaging tests.

As used herein, "prevention" or "preventing" of a disorder or condition refers to a compound that, in a statistical sample, reduces the occurrence of the disorder or condition in the treated sample relative to a control sample, or delays the onset of one or more symptoms of the disorder or condition relative to the control sample.

It is also to be appreciated that the various modes of treatment or prevention of medical diseases and conditions as described are intended to mean "substantial," which includes total but also less than total treatment or prevention, and wherein some biologically or medically relevant result is achieved.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, ave, etc. In some embodiments, the mammal is murine. In some embodiments, the mammal is human.

A subject "in need" of treatment according to the methods and/or compositions of the present technology includes a subject that is "suffering" from inflammation (i.e., a subject that is experiencing and/or exhibiting one or more clinical and/or subclinical symptoms of inflammation), and a subject "at risk" of inflammation. A subject "in need" of treatment includes animal models of inflammation. Subject "at risk" of inflammation refers to a subject that is not currently exhibiting inflammation symptoms and is predisposed to expressing one or more symptoms of the disease. This predisposition may be based on family history, genetic factors, environmental factors such as exposure to detrimental compounds present in the environment, etc. It is not intended that the present technology be limited to any particular signs or symptoms. Thus, it is intended that the present technology encompass subjects that are experiencing any range of disease, from sub-clinical symptoms to full-blown inflammatory disease, wherein the subject exhibits at least one of the indicia (e.g., signs and symptoms) associated with the inflammatory disease.

"Substantially the same," "without substantially altering," "substantially unaltered," and grammatical equivalents, when in reference to the level of any molecule (e.g., multidrug resistance protein 2 (MRP2), multidrug resistance protein 1 (MRP1), hepoxilin A3 ($HXA_3$) synthase, N-acyl ethanolamine (NAE), amino acid sequence, nucleic acid sequence, antibody, etc.), cell, and/or phenomenon (e.g., level of activity of multidrug resistance protein 2 (MRP2) and/or of multidrug resistance protein 1 (MRP1) and/or of hepoxilin A3 ($HXA_3$) synthase and/or N-acyl ethanolamine (NAE), level of expression of a gene, disease symptom, level of binding of two molecules such as binding of a hormone ligand to its hormone receptor, specificity of binding of two molecules, affinity of binding of two molecules, disease symptom, specificity to disease, sensitivity to disease, affinity of binding, enzyme activity, etc.) means that the quantity of molecule, cell, and/or phenomenon in the first sample (or in the first subject) is neither increased nor decreased by a statistically significant amount relative to the second sample (or in a second subject). Thus, in one embodiment, the quantity of molecule, cell, and/or phenomenon in the first sample (or in the first subject) is from 90% to 100% (including, for example, from 91% to 100%, from 92% to 100%, from 93% to 100%, from 94% to 100%, from 95% to 100%, from 96% to 100%, from 97% to 100%, from 98% to 100%, and/or from 99% to 100%) of the quantity in the second sample (or in the second subject).

As used herein, "weight percent" of a component, unless specifically stated to the contrary, is based on the total weight of the formulation or composition in which the component is included.

II. General

The present technology provides methods and compositions for treating neutrophil-mediated inflammation. In particular, the present technology provides a method for treating neutrophil-mediated inflammation in a target tissue of a mammalian subject in need thereof, comprising administering to the subject a therapeutically effective amount of one or more first compound that increases the level and/or activity of multidrug resistance protein 1 (MRP1), wherein the therapeutic amount of the first compound reduces migration of neutrophils into the target tissue, and/or administering a therapeutically effective amount of one or more second compound that inhibits one or more of multidrug resistance protein 2 (MRP2), and hepoxilin A3 ($HXA_3$) synthase, wherein the therapeutic amount of the second compound reduces migration of neutrophils into the target tissue, and/or administering a therapeutically effective amount of one or more third compound that increases one or more N-acylethanolamines (NAEs), wherein the therapeutic amount of the third compound reduces migration of neutrophils into the target tissue.

In one embodiment, the present disclosure provides methods for treating neutrophil-mediated inflammation by targeting the pro-inflammatory MRP2/$HXA_3$ pathway, comprising administering to the subject a therapeutically effective amount of one or more compound that inhibits the activity and/or level of one or more of multidrug resistance protein 2 (MRP2) and hepoxilin A3 ($HXA_3$) synthase, wherein the therapeutic amount of the compound reduces migration of neutrophils into the target tissue.

In another embodiment, the present disclosure also provides methods for treating neutrophil-mediated inflammation by targeting the anti-inflammatory P-gp/endocannabinoid pathway, comprising administering to the subject a therapeutically effective amount of one or more compound that increases the level and/or activity of one or more N-acylethanolamines (NAEs), wherein the therapeutic amount of the compound reduces migration of neutrophils into the target tissue.

In a further embodiment, the present disclosure further provides methods for treating neutrophil-mediated inflammation, comprising administering to the subject a therapeutically effective amount of one or more second compound that increases the level and/or activity of multidrug resistance protein 1 (MRP1), wherein the therapeutic amount of the compound reduces migration of neutrophils into the target tissue In yet another embodiment, the present disclosure provides methods for treating neutrophil-mediated inflammation by targeting both the anti-inflammatory P-gp/endocannabinoid, and the pro-inflammatory MRP2/$HXA_3$ pathway, the method comprising administering to the subject a therapeutically effective amount of (A) one or more first compound that inhibits the activity and/or level of one or more of multidrug resistance protein 2 (MRP2) and hepoxilin A3 ($HXA_3$) synthase, and (B) one or more second compound that increases the level and/or activity of one or more N-acylethanolamines (NAEs), wherein the therapeutic amount of the first and second compounds reduces migration of neutrophils into the target tissue.

Bacteria are the most common cause of lower respiratory tract infections and produce a greater disease burden throughout the world than many other infections, such as human immuno-deficiency virus (HIV) and malaria. The Centers for Disease Control and Prevention (CDC) estimate that *Streptococcus pneumoniae* (pneumococcus), the bacterium that causes the most bacterially derived community-acquired-pneumonia, causes 500,000 cases of pneumonia each year in the United States. As many as 30% of these cases also develop bacteremia, and overall case fatality can reach 5-7%, resulting in approximately 35,000 deaths, annually. Mortality after diagnosis of bacteremia is significantly higher—closer to 20% of cases (Moore and Pilishvilli, "Pneumococcal Disease". In: *Epidemiology and Prevention of Vaccine-Preventable Diseases*. Centers for Disease Control and Prevention. Epidemiology and Prevention of Vaccine-Preventable Diseases. Hamborsky and Wolfe, Eds. 13$^{th}$ ed. Washington D.C. Public Health Foundation, 2015; Pilishvili, et al., "Pneumococcal Disease". Chapter 11. 2012. In: *Manual for the surveillance of vaccine-preventable diseases*. Roush and Baldy, Eds. 5$^{th}$ ed. Centers for Disease Control and Prevention, Atlanta, GA, 2008). Furthermore, pneumococcal disease contributes to approximately 0.5-1 million juvenile deaths annually despite the availability of vaccines and antibiotic treatments (Moore and Pilishvilli, 2015; Pilishvili, et al., "Pneumococcal Disease". Chapter 11. 2012. In: *Manual for the surveillance of vaccine-preventable diseases*. Roush and Baldy, Eds. 5$^{th}$ ed. Centers for Disease Control and Prevention, Atlanta, GA, 2008; World Health Organization. "Pneumococcal Vaccines". No. 14, 2012, 87, 129-144. Position paper on pneumococcal vaccines (April 2012)).

During respiratory infection that leads to pneumonia, a hallmark pathology is the recruitment of polymorphonuclear cells (PMNs, or neutrophils) from the pulmonary capillaries into the luminal spaces (Loosli and Baker, *Trans. Am. Clin. Climatol. Assoc.* 74:15-28 (1962)). Although this response serves to initially clear the bacterial infection, it also contributes directly to lung injury and pulmonary dysfunction (Baird et al., *J. Appl. Physiol.* 61(6): 2224-2229 (1986); Flick et al., *Circ. Res.* 48(3):344-351 (1981); Menendez et al., *Thorax* 63(5):447-452 (2008)). Indeed, excessive inflammation is a major cause of early treatment failure and mortality in the treatment of pneumococcal pneumonia (Menendez et al., (2008)). Additionally, there is a growing body of literature that indicates that bacterial infiltration to the blood can be mediated by PMN infiltration to the luminal space during inflammation (Marks et al., *Infect. Immun.* 75(4): 1586-1597 (2007); Clarke et al., *Cell Host Microbe* 9(5):404-414 (2011); Attali et al., *Infect. Immun.* 76(11): 5350-5356 (2008); Bhowmick et al., *J. Immunol.* 191(10): 5115-5123 (2013)).

To better understand the mechanisms underlying the regulation of PMN influx during pneumococcal infection, host mediators of *S. pneumoniae*-induced PMN migration and the role of inflammation in septicemia following pneumococcal lung infection were examined. It was observed that PMN migration into the lung airways during pneumococcal infection required the production of the lipid chemoattractant hepoxilin $A_3$ ($HXA_3$), an eicosanoid derived from arachidonic acid via the action of 12-lipoxygenases (LOX) in lung epithelial cells (Bhowmick et al., (2013)). Pharmacologic inhibition or genetic ablation of 12-LOX profoundly decreased PMN influx into the lungs of *S. pneumoniae*-infected mice and resulted in uniform survival of mice to an otherwise lethal pneumococcal pulmonary challenge (Bhowmick et al., (2013)). These findings indicate that pneumococcal pulmonary inflammation is required for high-level bacteremia and systemic infection, at least in part, by disrupting lung epithelia through 12-LOX-dependent $HXA_3$ production and subsequent PMN transepithelial migration.

Studies initially focusing on the intestinal epithelium have revealed that the ATP-Binding Cassette (ABC) Transporter multi-drug resistance associated protein 2 (MRP2; also known as ABCC2 or c-MOAT) facilitates the release of $HXA_3$, and its secretion is regulated by conditions that modulate inflammatory events at mucosal surfaces (Pazos et al., *J. Immunol.* 181(11):8044-8052 (2008)). Secretion of $HXA_3$ to the apical surface of epithelial cells establishes a gradient across the intestinal epithelial tight junction complex and produces a chemotactic gradient used by PMNs to target the mucosal lumen at sites of inflammation (Mrsny et al., *Proc. Natl. Acad. Sci. USA* 101(19):7421-7426 (2004)). Although ABC transporters were originally identified for their contribution to clinical multi-drug resistance as a result of their capacity to extrude various cytotoxic drugs, emerging reports have further documented that ABC transporters might play a role in host defense and are involved in migration of immune effector cells to sites of inflammation. Moreover, many endogenous ABC transporter substrates exhibit immuno-regulatory effects (Furugen et al., *Prostaglandins Other Lipid Mediat* 106:37-44 (2013); Lin et al., *Mol. Pharmacol.* 73(1):243-251 (2008); van der Deen et al., *Virchows Arch* 449(6): 682-688 (2006); Blokzijl et al., *J. Biol. Chem.* 283(51):35630-35637 (2008); Englund et al., *Inflamm. Bowel Dis.* 13(3):291-297 (2007); Panwala et al., *J. Immunol.* 161(10):5733-5744 (1998); Yacyshyn et al., *Hum. Immunol.* 60(8):677-687 (1999)). Such ABC transporters that mediate this activity in the lung during inflammatory events, however, remain unidentified.

A hallmark immune reaction to bacterial-induced pneumonia is the invasion of PMNs from the vasculature to the luminal spaces of the lung (Loosli and Baker, (1962)). Although this response serves to reinforce innate immunity, it also contributes directly to lung injury and pulmonary dysfunction (Baird et al., *J. Appl. Physiol.* 61(6):2224-2229 (1986); Flick et al., *Circ Res,* 48(3):344-351 (1981)). While much is known about the mechanics of chemotaxis, and the microbicidal functions of PMNs, the mechanisms governing recruitment of PMNs to the lung/airway epithelium are not well understood. Indeed, many molecules mediating innate immune responses during pneumococcal pneumonia infection are redundant and/or dispensable for PMN recruitment. For example, TLRs mediate signaling from *S. pneumoniae*, but neither TLR2 nor TLR4 deficiency compromise PMN infiltration during pneumococcal pneumonia (Knapp et al., *J. Immunol.* 172(5):3132-3138 (2004); Branger et al., *Infect. Immun.* 72(2):788-794 (2004)). Selectins, VLA-4, and PCAM-1 are required for PMN recruitment during many inflammatory responses, but not during pneumococcal pneumonia (Mizgerd et al., *J. Exp. Med.* 184(2):639-645 (1996); Tasaka et al., *Am. J. Respir. Crit. Care Med.* 166(1):53-60 (2002); Doyle et al., *J. Clin. Invest.* 99(3):526-533 (1997); Tasaka et al., *Am. J. Respir. Crit. Care Med.* 167(2): 164-170 (2003)). CD11/CD18 and ICAM-2 are believed to play a role to maximize PMN recruitment elicited by a variety of stimuli in the lungs, but they do not make significant contributions to PMN recruitment during pneumococcal pneumonia (Mizgerd et al., *J. Immunol.* 163(2): 995-999 (1999); Mizgerd et al., *J. Leukoc. Biol.* 64(3):291-297 (1998)). ICAM-1 may play a role to fully elicit neutrophil emigration but this effect is believed lost at 24 hours (Mizgerd et al., (1998)). Also, while CXC chemokines are well documented to play roles in PMN trafficking in pneumococcal pneumonia, their functional redundancy in PMN recruitment limits their efficacy as therapeutic agents (Jones et al., *J. Immunol.* 175(11):7530-7535 (2005); Eliasson et al., *Microbes Infect.* 12(7):565-573 (2010); Seyoum et al., *Vaccine* 29(45):8002-8011 (2011)).

Having shown that the MRP/$HXA_3$ pathway is conserved during infection with multiple pathogens in both lung and intestinal epithelia, whether it also drives inflammation in the absence of infection was examined (Example 3).

Mice lacking the mdr1a gene that encodes P-gp develop spontaneous intestinal inflammation. The evidence that lack of P-gp promotes inflammation and the characteristics of known exogenous P-gp substrates led to the hypothesis that P-gp might secrete endogenous bioactive lipids, which could serve to antagonize $HXA_3$-mediated migration. The P-gp-dependent secreted lipidome of homeostatic epithelial cells was analyzed to identify lipids capable of inhibiting $HXA_3$-mediated neutrophil migration. (Example 4).

Data in Examples 3-10 have implications for understanding the regulation of neutrophil transmigration, such as the exemplified intestinal lumen (Examples 3-7) and exemplified lung (Examples 8-10).

Figure 10:
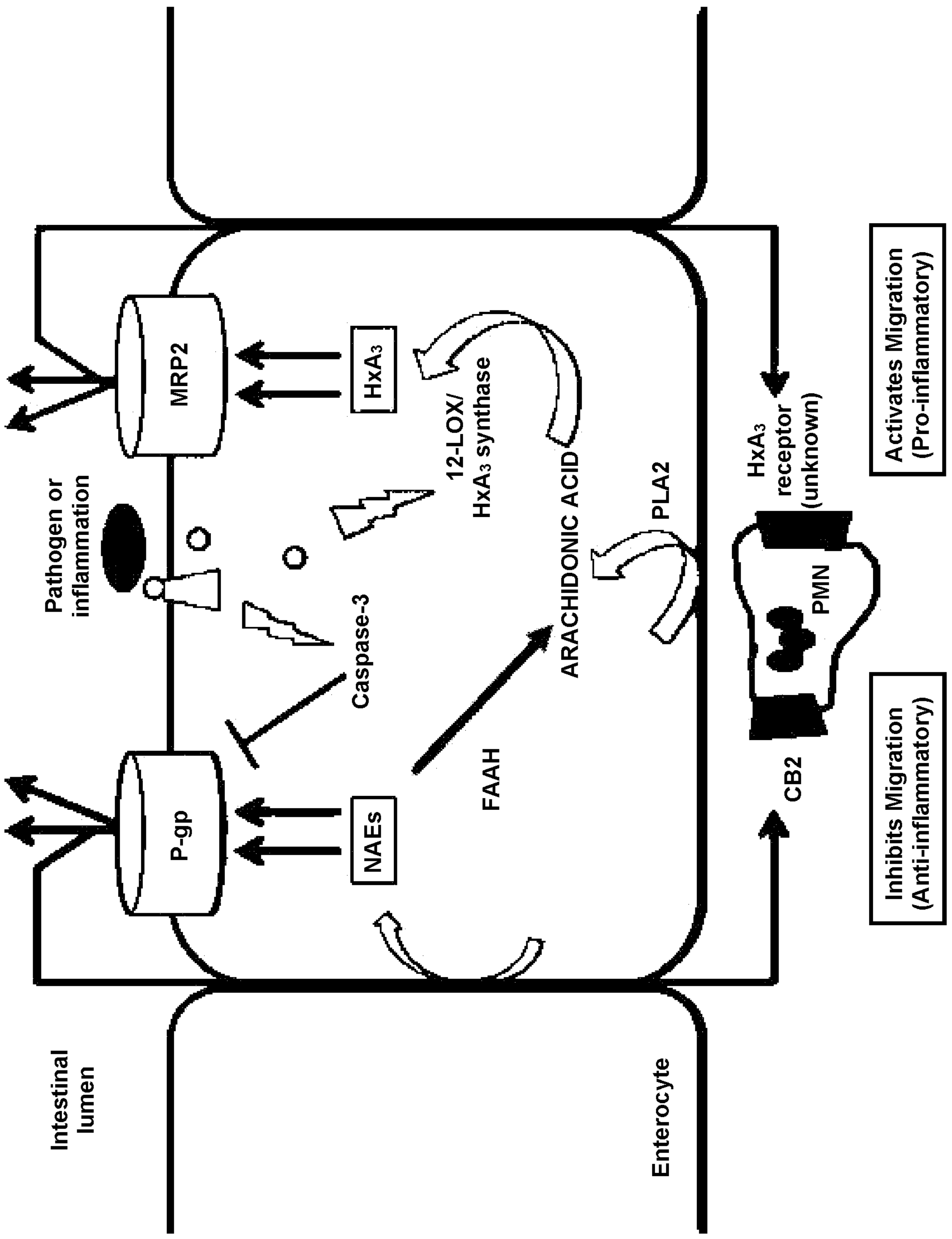
FIG. 10. The anti-inflammatory P-gp/endocannabinoid and pro-inflammatory MRP2/$HXA_3$ pathways in the intestinal epithelium. In the homeostatic intestine, P-glycoprotein secretes endocannabinoids from the epithelial surface. Secreted N-acyl ethanolamines (NAEs) act through the CB2 receptor on neutrophils to inhibit migration and maintain an anti-inflammatory state. During inflammation, P-gp is downregulated (by Caspase-3 degradation in the case of *Salmonella typhimurium*) and the MRP2/$HXA_3$ pathway is activated. Phospholipase A2 liberates arachidonic acid from the membrane and it is converted to $HXA_3$ and secreted into the lumen via surface MRP2. $HXA_3$ forms a concentration gradient that attracts neutrophils across the epithelial layer into the lumen, where they cause inflammatory damage and pathology. Of note, FAAH metabolism of NAEs yields arachadonic acid and may also feed into the pro-inflammatory MRP2/$HXA_3$ pathway.

Data herein (Examples 3-7) have defined an anti-inflammatory P-gp/endocannabinoid pathway that acts to counterbalance the pro-inflammatory MRP2/$HXA_3$ axis (FIG. 10). In addition, this proposed dynamic relationship provides potential explanations for several scientific questions including: 1) the correlation between P-gp dysfunction and colitis; 2) the existence of endogenous non-xenobiotic substrates for P-gp; and 3) the mechanism underlying reports of suppression of colitis symptoms by CB2 agonists. Thus, modulation of the pro-inflammatory MRP2/$HXA_3$ and/or the anti-inflammatory P-gp/endocannabinoid pathways at the luminal surface of the intestine represents a new avenue for development of topical therapeutics for the treatment of inflammatory disease, such as bowel disease. Furthermore, the MRP2/$HXA_3$ pathway is conserved in infectious and non-infectious lung inflammation, suggesting that this pathway and the P-gp/endocannabinoid pathway may similarly regulate inflammation at other mucosal surfaces.

Thus, in one embodiment, the present technology provides a method for treating neutrophil-mediated inflammation by targeting the pro-inflammatory MRP2/$HXA_3$ pathway (FIG. 10). In a particular embodiment, this method for treating neutrophil-mediated inflammation in a target tissue of a mammalian subject in need thereof, comprises administering to the subject a therapeutically effective amount of one or more first compound that inhibits the activity and/or level of one or more of: a) multidrug resistance protein 2 (MRP2); and b) hepoxilin A3 ($HXA_3$) synthase, wherein the therapeutic amount of the first compound reduces migration of neutrophils into the target tissue. Data herein show that the proinflammatory role of MRP2/$HXA_3$ is similar in both lung (Examples 8-10) and intestine (Examples 3-7), and in both in non-infectious (aseptic) as well as infectious (septic) inflammation that is caused by a pathogen.

In some embodiments, it may be desirable to treat inflammation by also targeting the anti-inflammatory P-gp/endocannabinoid pathway (FIG. 10). Thus, in one embodiment, the method further comprises administering to the subject a therapeutically effective amount of one or more second compound that increases the level and/or activity of one or more N-acylethanolamines (NAEs), wherein the therapeutic amount of the second compound reduces migration of neutrophils into the target tissue.

Data herein (Examples 8-10) was obtained to determine whether ABC transporters in the airway epithelium perform an immunomodulatory role that governs PMN migration during *S. pneumoniae* infection. As demonstrated herein, the ABC transporters MRP1 and MRP2 are not only divergently expressed during pneumococcal infection but also actively efflux substrates with opposing roles in the control PMN migration. Characterizing this unique relationship, MRP1 appears to efflux substrates during homeostasis that suppress PMN migration but during infection with *S. pneumonia* expression of this transporter at the apical surface is significantly diminished. In contrast, MRP2 effluxes substrates that promote PMN migration and during pneumococcal infection this transporter is highly enriched on the apical surface. Thus, data in Examples 8-10 establishes that ABC transporters in the pulmonary system may play a role in regulating the balance between homeostatic pathways that suppress PMN responses and the inflammatory pathways that activate during responses to pathogens, such as *S. pneumoniae*. Dysregulation of this balance governs a very specific but useful arm of the innate inflammatory response.

Data presented in Examples 8-10 has uncovered a system of epithelial-specific counterbalances in which efflux transporters coordinate PMN migration across lung epithelia during infection with *S. pneumoniae*. Specifically, at uninfected basal states, MRP1 expression mediates efflux of immunosuppressive molecule(s) (i.e., L-AMEND) to maintain homeostasis and to prevent any collateral damage from non-specific PMN migration. Under the same homeostatic state, MRP2 surface-expression is quite low, strengthening the anti-inflammatory arm of this pathway. However, upon introduction of *S. pneumoniae*, expression of MRP1 decreases, reducing the effective concentration of anti-inflammatory molecules at the site of infection. Conversely, the apical expression of MRP2 increases, facilitating the efflux of a lipid PMN chemoattractant, likely $HXA_3$; an eicosanoid that in turn, can attract PMNs to the site of infection/injury and has been shown to play a role in many other bacterial infections (Pazos\ et al., (2008); Mrsny et al., (2004); Hurley et al., *J. Immunol.* 173(9):5712-5720 (2004); Mumy et al., *Infect. Immun.* 76(8):3614-3627 (2008); Boll et al., *Cell Microbiol,* 14(1):120-132 (2012)). One contention that $HXA_3$ is a proinflammatory mediator that guides the recruitment of PMN across epithelial barriers is reinforced by recent reports of the increased presence and function of this potent PMN chemoattractant in inflammatory-based diseases such as psoriasis and infectious/non-infectious enterocolitis (Mrsny et al., (2004); Antón et al., *J. Invest. Dermatol.* 110(4):303-310 (1998)). $HXA_3$ has also been detected in the rat lung (Pace-Asciak et al., *Biochim. Biophys. Acta,* 875(2):406-409 (1986)), but its precise role in the process of PMN recruitment resulting from bacterial lung infection is still under appreciated.

The results in Examples 8-10 suggest that $HXA_3$/MRP2 and L-AMEND/MRP1 axes are part of universal mechanisms that may help control inflammation in the lung. Polarized expression of MRP2 and the activity of this $HXA_3$/MRP2 axis are greatly increased during inflammatory states, and this pathway is non-redundant with other chemoattractants driving PMN recruitment, such as IL-8. Data presented herein is in line with others showing that MRP1 expression and activity corresponds to an anti-inflammatory state while the $HXA_3$/MRP2 axis is a conserved mechanism at mucosal surfaces for protection from pathogenic bacteria (Pazos et al., (2008); Blokzijl et al., (2008); Agbor et al., (2011)). Moreover, in Examples 8-10, it was found that blockade of MRP2 during *S. pneumoniae* infection profoundly decreased PMN influx into the lungs of *S. pneumoniae*-infected mice and, in turn, reduced the amount of bacteria detected in the blood after infection. Such findings bolster the concept that PMN influx induced by pneumococcal pulmonary inflammation may contribute to the pathology of bacterial infection.

Figure 22B:
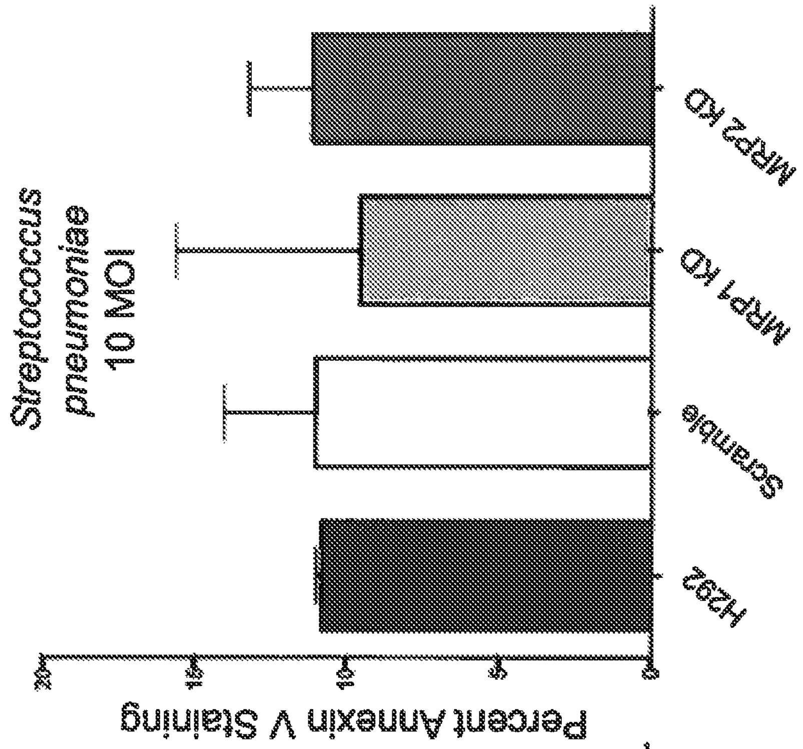
FIGS. 22A and 22B. Testing Apoptosis in MRP knockdown cells. H292 cells with control constructs, MRP1 shRNA, or MRP2 shRNA underwent staining for apoptosis either pre-infection (FIG. 22A) or post-infection (FIG. 22B). In both cases, there was no significant increase in apoptosis during the staining procedure.
Figure 22A:
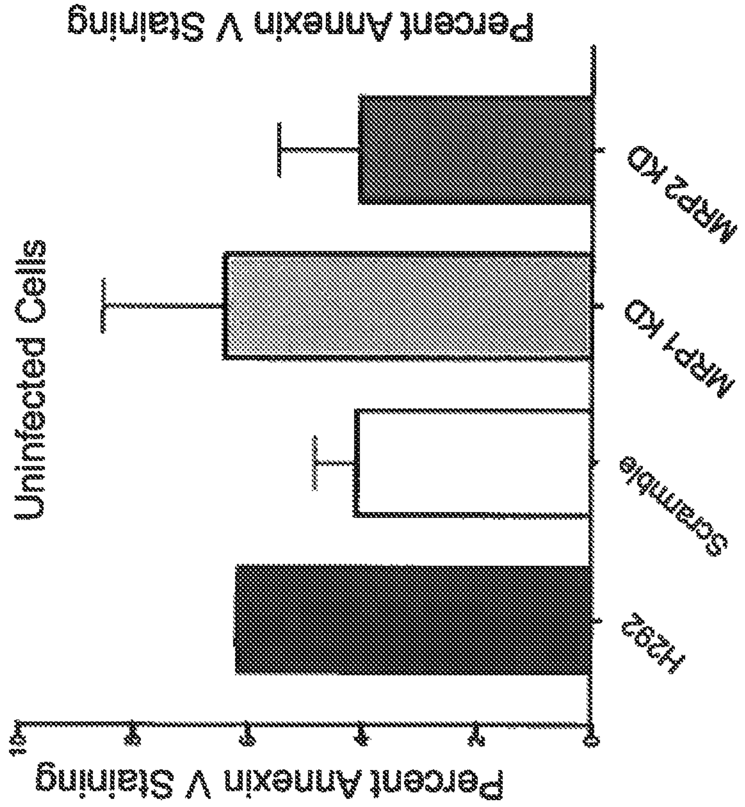

Schultz et al. previously reported that global Mrp1 knockout mice were protected during pneumococcal infection whereas wild-type littermates succumb to infection (Schultz, et al., *J. Immunol.* 166(6):4059-4064 (2001)). In Examples 8-10, it was shown that at 48 hours post-infection, extracellular leukotriene C4 ($LTC_4$) in Mrp1−/− BALF is lower than in wild-type mice. Intracellular $LTC_4$, understandably, was found to be higher, leading to the conclusion that release of $LTC_4$ is inhibited by the elimination of murine Mrp1. $LTC_4$ retention was suggested to be cytotoxic (Blokzijl et al., (2008)) in this particular study, which could lead to PMN apoptosis and reduced numbers of neutrophils in the BALF; the very result Schultz demonstrates 48 hours post-infection. In this instance, such reduced neutrophil numbers would prevent epithelial-wall breaches and reduce the bacterial infiltration, allowing other means of bacterial clearance to eliminate the pneumococcal infection, as implied by Marks et al. and Bhowmick et al. The apparent paradox presented by this data seems to align with our hypothesis that MRP1 activity is assisting in repression of PMN transmigration. To ensure that infected epithelium do not undergo an LTC4-induced apoptosis, Annexin V staining of both pre- and post-infection in the MRP1-deficient epithelium and control cells (FIGS. 22A and 22B) was tested, indicating that any increases in PMN migration associated with MRP1 deficiency is not caused by epithelial cytotoxicity.

The hypothesis that MRP1/L-AMEND dictates an anti-inflammatory state (Examples 8-10) while MRP2/$HXA_3$ a pro-inflammatory one (Examples 3-7) incorporates the concept that epithelial cells (through regulation of ABC efflux transporters) act as sensors that integrate signals in order to determine when to incite PMN transmigration. Thus, a steady-state set point is established that limits inappropriate inflammatory responses but which is poised to respond to the presence of pathogens, such as *S. pneumoniae* (or other pro-inflammatory stimuli). Although this PMN response may play a part in controlling the infection at hand, prolonged neutrophil activation is also believed to have deleterious effects on health, highlighting a cost-benefit relationship for the host. Data presented herein demonstrate that a better understanding of the mechanisms underlying the regulation of PMN influx during pneumococcal infection may be useful to design improved therapies that ultimately allow for containment of the infection but dampen detrimental lung inflammation at the same time.

Thus, in a further embodiment of the present technology, it may be desirable to administer to the subject a therapeutically effective amount of one or more compound that increases the level and/or activity of multidrug resistance protein 1 (MRP1), wherein the therapeutic amount of this one or more compound reduces migration of neutrophils into the target tissue (Examples 8-10). In some embodiments, MRP1 upregulation may be unnecessary (though it may be optionally included) when treating disease with L-AMEND and/or other cannabinoids that are anti-inflammatory.

Increased levels of multidrug resistance protein 1 (MRP1) may be achieved by, for example, using transfection of mRNA sequences that encode MRP-1, using viral vectors carrying a MRP-1 gene insert under a tissue specific promoter (Hao et al., *Cancer Biology & Therapy,* 5(3):261-266, DOI: 10.4161/cbt.5.3.2381), using small molecules such as Ivermectin (STROMECTOL®) (Raza et al., *Parasites & Vectors* 9:522, DOI: 10.1186/s13071-016-1806-9 (2016)), and such as anti-cancer drugs. Numerous chemotherapeutic agents, including, but not limited to, doxorubicin and vinblastine, have been reported to induce MRP1 expression, and a role for nuclear hormone regulation via CAR has been reported (Bakos et al., *Pflugers Arch—Eur J Physiol* 453: 621-641 (2007)).

In some embodiments, the methods of the present technology may optionally further comprise administering one or more antibiotic and/or anti-inflammatory agent. Examples of antibiotic/anti-inflammatory agents used singly or in combination in the methods of the present technology include, but are not limited to Dalbavancin (DALVANCEO, XYDALBAC), Oritavancin (ORBACTIVEC) Daptomycin (Cubicin®), Tedizolid (SIVEXTROC), Ceftobiprole (ZEVTERAC, MABELIOC), Ceftolozane-tazobactam (ZERBAXAC) mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppresant agents such as cyclosporin, and cytokine synthesis inhibitors, tetracycline, minocycline, and doxycycline, or any combination thereof.

In some embodiments, the methods of the present technology may optionally further comprise administering one or more antibodies, such antibodies targeting one or more of *Clostridium difficile* toxins, tumor necrosis factor (TNF), interleukins, metalloproteinase-9 (such as the antibody GS-5745, Gilead).

For example, in Crohn's disease, it may be desirable that any one of the methods of the present technology further comprise administering one or more mesalamine products, corticosteroid formulations, both conventional corticosteroids and ileal-release budesonide, glucocorticosteroids/EEN immunomodulatives (such as azathioprine, 6-mercaptopurine, and methotrexate), anti-tumor necrosis factor (TNF) drugs (such as infliximab (Remicade, Janssen), adalimumab (Humira, AbbVie), and certolizumab pegol (Cimzia, UCB)), the anti-alpha-4 beta-7 integrin antibody vedolizumab (Entyvio, Takeda), the JAK inhibitors ABT-494 (AbbVie), and filgotinib (GLPG0634, Galapagos and Gilead) (Sandborn, The Present and Future of Inflammatory Bowel Disease Treatment Gastroenterology & Hepatology, Volume 12, Issue 7, July 2016).

For ulcerative colitis, it may be desirable that any one of the methods of the present technology further comprise administering one or more of 5-aminosalycylates, mesalamine, conventional corticosteroids or multimatrix budesonide (Uceris, Salix), which delivers the drug to the colon, azathioprine, 6-mercaptopurine, anti-TNF drugs (such as infliximab, adalimumab, and golimumab (Simponi, Janssen)), vedolizumab, Janus kinase (JAK) inhibitors (e.g., Tofacitinib (Xeljanz, Pfizer) ABT-494 (AbbVie), and filgotinib (GLPG0634, Galapagos and Gilead)) (Sandborn 2016).

III. Compounds of the Present Technology

The present technology provides compositions for treating neutrophil-mediated inflammation and conditions associated therewith. In some embodiments, the present technology provides compositions comprising one or more of a first compound that increases the level and/or activity of multidrug resistance protein 1 (MRP1), a second compound that inhibits one or more of multidrug resistance protein 2 (MRP2) and hepoxilin A3 ($HXA_3$) synthase, and/or a third compound that increases one or more N-acylethanolamines (NAEs).

A. Compounds that Increase MRP1

In some embodiments, increased levels of multidrug resistance protein 1 (MRP1) may be achieved by, for example, using transfection of mRNA sequences that encode MRP-1, using viral vectors carrying a MRP-1 gene insert under a tissue specific promoter (Hao et al., *Cancer Biology & Therapy,* 5(3):261-266, DOI: 10.4161/cbt.5.3.2381), using small molecules such as Ivermectin (STROMECTOL®) (Raza et al., *Parasites & Vectors* 9:522, DOI: 10.1186/s13071-016-1806-9 (2016)), and such as anti-cancer drugs. Numerous chemotherapeutic agents, including, but not limited to, doxorubicin and vinblastine have been reported to induce MRP1 expression, and a role for nuclear hormone regulation via CAR has been reported (Bakos et al., *Pflugers Arch—Eur J Physiol* 453:621-641 (2007)).

B. MRP2 Inhibitors

In some embodiments, the compound that inhibits multidrug resistance protein 2 (MRP2) is exemplified by one or more of MRP2 RNAi; 3-([3-(2-[7-chloro-2-quinolinyl]ethenyl)phenyl-(3-dimethylamino-3-oxopropyl)-thio-methyl] thio)propanoic acid (also known as "MK571" and CysLT1 (LTD4) leukotriene receptor inverse agonist) (Tocris, Minneapolis, USA) (Genuuso et al. (2004) *PNAS* 101:2470-2475); Probenecid (also known as "PROBALAN™"), exemplified by probenecid inhibition of MRP2 (Example 3); FUROSEMIDE®; RITONAVIR®; SAQUINA VIR®; LAMIVUDINE®; ABACAVIR®; EMTRICITABINE®; EFAVIRENZ®; DELAVIRDINE®; NEVIRAPINE®; CIDOFOVIR®; ADEFOVIR®; and TENOFOVIR®.

In some embodiments, the compound that inhibits the MRP2 is exemplified by one or more of a compound that inhibits Hepoxilin A3 synthase, such as Hepoxilin A3 synthase RNAi.

In some embodiments, the compound that inhibits the MRP2 is exemplified by one or more compound that inhibits fatty acid amide hydrolase (FAAH), such as FAAH RNAi; FAAH Inhibitor I (PubChem CID: 295380) 4-phenylmethoxyphenyl)N-butylcarbamate); URB597 (PubChem CID: 1383884) 3'-Carbamoyl-[1,1'-biphenyl]-3-yl cyclohexylcarbamate; FAAH inhibitor 1 (PubChem CID: 1190414)N-(4-(6-methylbenzo[d]thiazol-2-yl)phenyl)-1-(thiophen-2-ylsulfonyl)piperidine-4-carboxamide; FAAH Inhibitor, 21 (PubChem CID:71699786); FAAH Inhibitor, 2i (PubChem CID: 71699785)N-Cyclohexylcarbamic acid 4-(dimethylamino)-3-phenylphenyl ester; FAAH Inhibitor, 2 h (PubChem CID: 71699784)N-Cyclohexylcarbamic acid 4-(hydroxymethyl)-3-phenylphenyl ester; FAAH Inhibitor, 2j (PubChem CID: 58801136); FAAH Inhibitor, 2e (PubChem CID: 58801135); FAAH Inhibitor, 2a (PubChem CID: 58801134); FAAH Inhibitor, 2b (PubChem CID: 58801129); FAAH Inhibitor, 2f (PubChem CID: 58801126) Carbamic acid, cyclohexyl-, 6-methyl[1,1'-biphenyl]-3-yl ester; FAAH Inhibitor, 2 k (PubChem CID: 58801125); FAAH Inhibitor, 2c (PubChem CID: 57582480); FAAH Inhibitor, 2 g (PubChem CID: 44626363); FAAH Inhibitor, 2d (PubChem CID: 44626362); AM374, palmitylsulfonyl fluoride; ARN2508, derivative of flurbiprofen; BIA 10-2474; BMS-469908; CAY-10402; JNJ-245; JNJ-1661010; JNJ-28833155; JNJ-40413269; JNJ-42119779; JNJ-42165279; LY-2183240; Cannabidiol; MK-3168; MK-4409; MM-433593; OL-92; OL-135; PF-622; PF-750; PF-3845; PF-04457845; PF-04862853; RN-450; SA-47; SA-73; SSR-411298; ST-4068; TK-25; URB524; URB597 (KDS-4103, Kadmus Pharmaceuticals); URB694; URB937; VER-156084; V-158866; and Multiple FAAH inhibitors from ChemCruz® Biochemicals, Dallas, Texas).

In some embodiments, the compound that inhibits the MRP2 is exemplified by one or more compound that inhibits P-glycoprotein (P-gp), such as P-gp RNAi; SipA; and small molecules (e.g., zosuquidar trihydrochloride (LY335979); VALSPODAR® (PSC833) (Inhibitor of P-gp-mediated MDR); CP 100356 hydrochloride (Sigma-Aldrich); and Elacridar hydrochloride (R&D Systems). See also, WO 2004071498 A1; WO 2014106021 A1; WO 2005033101 A1; WO 2004009584 A1; WO 2002030915 A2; US 20100029755 A1; and US 20060073196 A1).

While not intending to limit the type of composition in which the compounds of the present technology are administered, in some embodiments, the compounds of the present technology (e.g., compounds that reduce migration of neutrophils into the target tissue and/or compounds that inhibit the activity and/or level of one or more of MRP2 and $HXA_3$ synthase, and/or compounds that increase the level and/or activity of N-acylethanolamines (NAEs)), and/or compounds that increase multidrug resistance protein 1 (MRP1), are conjugated to a polymer.

Probenecid Conjugates of the Present Technology

In some embodiments, the present technology discloses a probenecid-polymer conjugate defined by Formula I:

Formula I

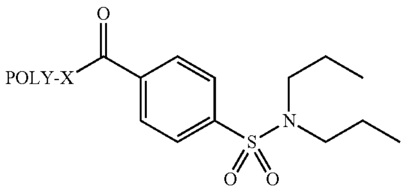

wherein X is a linker and POLY is a polymer.

In some embodiments, POLY is a polymer selected from the group consisting of dextran, polyethylene glycol (PEG), periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly (hydroxyalkylmethaacrylamide), polyglycerol, 25 polyamidoamine (PAMAM), polyethylenimine (PEI), and polypeptides. In some embodiments, PEG polymers are functionalized with amine ($NH_2$) and aldehyde (CHO) that include linear mono-amines and mono-aldehydes, linear bi-amines and bi-aldehydes, multi-arm-amines and multi-arm-aldehydes, branched mono-, bi- and multi-armed-amines and aldehydes and multi-arm-forked-amines and aldehydes. These polymers can be of any molecular weight as described herein.

In some embodiments, the polymer has an average molecular weight in the range of about 100 Da to about 800 kDa. (Unless otherwise indicated, "average molecular weight" means weight average molecular weight.) In some embodiments the polymer has an average molecular weight in the range of about 1 kDa to about 800 kDa. In some embodiments, the polymer has an average molecular weight less than 1 kDa. In some embodiments, the polymer has an average molecular weight less than 10 kDa. In some embodiments, the average molecular weight of the polymer is about 10 kDa, 20 kDa, 30 kDa, 40 kDa, 50 kDa, 60 kDa, 70 kDa, 80 kDa, 90 kDa, 100 kDa, 125 kDa, 150 kDa, 175 kDa, 200 kDa, 225 kDa, 250 kDa, 275 kDa, 300 kDa, 325 kDa, 350 kDa, 375 kDa, 400 kDa, 425 kDa, 450 kDa, 475 kDa, 500 kDa, 550 kDa, 600 kDa, 650 kDa, 700 kDa, 750 kDa, 800 kDa, or any range between and including two of these values.

The polymers described herein can have any of a number of different geometries. For example, in some embodiments, the polymers are linear polymers, branched polymers, forked polymers, or a combination of any of these polymers.

In some embodiments, probenecid is attached to the polymer via a linker X. In some embodiments, the linker can serve as a spacer to distance the probenecid compound and the polymer in order to avoid interference, with, for example, binding capabilities. The linker comprises one or more atoms, e.g., one or more atoms selected from C, N, or O. In some such embodiments the linker may further comprise one or more H atoms, e.g., NH, $N(CH_3)$, or $CH_2$.

In some embodiments, the linker is a biodegradable linker. In some embodiments, the biodegradable linker comprises an oligopeptide having from 2 to 10 amino acid residues. The residues may be selected from the naturally occurring amino acids.

In some embodiments, the linker comprises a substituted or unsubstituted $C_1$-$C_X$ alkylene, cycloalkylene, cycloalkylalkylene, heteroalkylene, alkenylene, or heteroalkenylene group, wherein x may be any integer from 1 to 12, i.e., 1, 2, 3, 4, 5, 6, 7, 8, 9, 10, 11 or 12. For example, the linker may comprise a $C_1$-$C_X$ fluoroalkyl group where one or more of the hydrogen atoms are fluorine atoms, such as 1, 2 or 3 or more fluorines. In some embodiments, X is a heteroalkylene containing one or two NH groups, including but not limited to ($C_1$-$C_{10}$ alkylene)-NH (e.g., $CH_2CH_2NH$, $CH_2CH_2CH_2NH$, $CH_2CH_2CH_2CH_2NH$, $CH_2CH(CH_3)CH(CH_3)CH_2NH$), ($C_n$ alkylene)NH($C_p$ alkylene) where n, p are independently an integer from 1-10, but n+p does not exceed 10 (e.g., $CH_2CH_2CH_2NH$ $CH_2CH_2$), NH—($C_1$-$C_{10}$ alkylene)NH (e.g., $NH(CH_2)_5NH$, $NH(CH_2)_6NH$, $NH(CH_2)_8NH$), or NH($C_n$ alkylene)NH($C_p$ alkylene) where n and p are integers as defined previously (e.g., $NHCH_2CH_2CH_2NH$ $CH_2CH_2$, $NH(CH_2)_6NHCH_2$). In some embodiments, X is a heteroalkylene that contains one or two oxygen atoms, including but not limited to ($C_1$-$C_{10}$ alkylene)-O (e.g., $CH_2CH_2O$, $CH_2CH_2CH_2O$, $CH_2CH_2CH_2CH_2O$, $CH_2CH(CH_3)CH(CH_3)CH_2O$), ($C_n$ alkylene)O($C_p$ alkylene) where n, p are independently an integer from 1-10, but n+p does not exceed 10 (e.g., $CH_2CH_2CH_2OCH_2CH_2$), O—($C_1$-$C_{10}$ alkylene)O (e.g., $O(CH_2)_5O$, $O(CH_2)_6O$, $O(CH_2)_8O$), or O($C_n$ alkylene)O($C_p$ alkylene) where n and p are integers as defined previously (e.g., $OCH_2CH_2CH_2O$ $CH_2CH_2$, $O(CH_2)_6OCH_2$). In some embodiments, X is a heteroalkylene containing an O and an NH group, including but not limited to NH—($C_1$-$C_{10}$ alkylene)O, (e.g., $NH(CH_2)_5O$, $NH(CH_2)_6O$, $NH(CH_2)_8O$), or NH($C_n$ alkylene)O($C_p$ alkylene) where n and p are integers as defined previously (e.g., $NHCH_2CH_2OCH_2CH_2$, $O(CH_2)_6NHCH_2$).

The probenecid-polymer conjugates may be prepared using standard techniques known in the art. In some embodiments, a difunctional linker containing at least two functional groups containing heteroatoms selected from N, O, and S in which one of the functional groups is protected may be conjugated using standard ester, thioester and amide bond forming technology. For example, a diamino-alkylene linker in which one of the amino groups is protected by a urethane protecting group (e.g., Boc. Cbz, etc.) may be coupled to probenecid in the presence of a coupling agent (e.g., DCC, EDC/HOBt, etc.). Alternatively, an active ester, mixed anhydride or acid halide derivative of probenecid may be prepared and reacted with the mono-protected diamine. (See, for example, Bodansky, M. & Bodanszky, A., *The Practice of Peptide Synthesis*, Springer-Verlag, New York, 1984.) The protecting group may be removed and the free amine reacted with an aldehyde derivative of the polymer under reducing conditions to provide the conjugate. Similarly, a linker with a protected aldehyde (e.g., 1,1-dimethoxy) and an amine may be coupled to the probenecid, deprotected to form the aldehyde and subjected to reductive amination with an amino-bearing polymer to form the conjugate. Variations of these schemes using α,ω-carboxy amines, α,ω-aminoalcohols, α,ω-carboxyalcohols, α,ω-aminothiols, and the like to link probenecid and the polymer will be readily understood by those of skill in the art.

C. Compounds that Increase NAEs

While not intending to limit the type of compound that increases N-acylethanolamines (NAEs), in some embodiments, the compound that increases NAEs is a cannabinoid receptor type 2 (CB2) "agonist" (i.e., a compound that specifically binds to, and activates, CB2). Illustrative CB2 agonists include GW-405,833; AM-1241; HU-308; JWH-015; JWH-133; L-759,633; L-759,656; beta-caryophyllene; arachidonylcyclopropylamide; and arachidonyl-2'-chloroethylamide.

IV. Uses of the Compositions of the Present Technology

The present technology provides methods for treating, preventing, or ameliorating neutrophil-mediated inflammation in a target tissue of a mammalian subject in need thereof, comprising administering to the subject a therapeutically effective amount of one or more first compound that inhibits one or more of multidrug resistance protein 2 (MRP2) and hepoxilin A3 ($HXA_3$) synthase, wherein the therapeutically effective amount of the first compound reduces migration of neutrophils into the target tissue. In some embodiments, the first compound is a probenecid conjugate. In some embodiments, the probenecid conjugate is a probenecid-periodate-oxidized 40 kDa dextran conjugate. In some embodiments, the method further comprises administering to the subject a therapeutically effective amount of one or more second compound that increases one or more N-acylethanolamines (NAEs), wherein the therapeutic amount of the second compound reduces migration of neutrophils into the target tissue. In a further embodiment, the method further comprises administering to the subject a therapeutically effective amount of one or more second and/or third compound that increases the level and/or activity of multidrug resistance protein 1 (MRP1), wherein the therapeutic amount of one or more second and/or third compound reduces migration of neutrophils into the target tissue. In another embodiment, the compounds of the present technology are administered singly or in any combination to a topical surface of the target tissue and/or at a luminal surface of the target tissue. In a further embodiment, the first compound that reduces migration of neutrophils into the target tissue is conjugated to a polymer. In another embodiment, the inflammation is non-infectious and/or infectious inflammation.

The present technology also provides methods for treating, ameliorating, or preventing neutrophil-mediated inflammation in a target tissue of a mammalian subject in need thereof, comprising administering to the subject a therapeutically effective amount of one or more first compound that increases one or more N-acylethanolamines (NAEs), wherein the therapeutic amount of the first compound reduces migration of neutrophils into the target tissue. In one embodiment, the method further comprises administering to the subject a therapeutically effective amount of one or more second compound that inhibits one or more of multidrug resistance protein 2 (MRP2) and $HXA_3$ synthase, wherein the therapeutic amount of the second compound reduces migration of neutrophils into the target tissue. In some embodiments, the second compound is a probenecid conjugate. In some embodiments, the probenecid conjugate is a probenecid-periodate-oxidized 40 kDa dextran conjugate. In another embodiment, the method further comprises administering to the subject a therapeutically effective amount of one or more second and/or third compound that increases the level and/or activity of multidrug resistance protein 1 (MRP1), wherein the therapeutic amount of the one or more second and/or third reduces migration of neutrophils into the target tissue. In a further embodiment, the one or more first compound that increases the one or more NAEs is a cannabinoid receptor type 2 (CB2) agonist. In another embodiment, the first compound that reduces migration of neutrophils into the target tissue is conjugated to a polymer.

In one aspect, the methods and compositions of the present technology relate to probenecid-polymer conjugates defined by Formula I:

Formula I

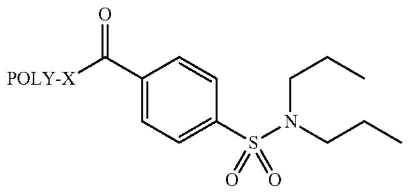

wherein X is a linker and POLY is a polymer, and the use of one or more of these conjugates to treat, ameliorate, or prevent neutrophil-mediated inflammation in a target tissue in a subject in need thereof. In other embodiments, the probenecid conjugates in combination with one or more compounds (e.g., a compound that increases the level and/or activity of MRP1, or a compound that increases NAEs) will show a synergistic effect in this regard.

In some embodiments, the methods and compositions of the present technology relate to the use of one or more of the probenecid conjugates of Formula I to treat, ameliorate, or prevent inflammatory bowel disease (IBD), such as ulcerative colitis (UC), Crohn's disease (CD), and infectious/non-infectious enterocolitis. In other embodiments, the probenecid conjugates in combination with one or more compounds (e.g., a compound that increases the level and/or activity of MRP1, or a compound that increases NAEs) will show a synergistic effect in this regard.

In some embodiments, the methods and compostions of the present technology relate to the use of one or more of the probenecid conjugates of Formula I to treat, ameliorate, or prevent infectious and non-infectious inflammatory lung conditions, including, but not limited to, pneumococcal infection, asthma, chronic obstructive pulmonary disease (COPD), and pulmonary fibrosis. In other embodiments, the probenecid conjugates in combination with one or more compounds (e.g., a compound that increases the level and/or activity of MRP1, or a compound that increases NAEs) will show a synergistic effect in this regard.

In some embodiments, the methods and compositions of the present technology relate to the use of one or more of the probenecid conjugates of Formula I to treat, ameliorate, or prevent inflammatory skin diseases including, but no limited to, dermatitis (eczema), rosacea, seborrheic dermatitis, and psoriasis. In other embodiments, the probenecid conjugates in combination with one or more compounds (e.g., a compound that increases the level and/or activity of MRP1, or a compound that increases NAEs) will show a synergistic effect in this regard.

The methods of the present technology are useful for treating "inflammation," which is a localized physical condition in which part of the body reacts to injury and/or infection. The classic symptoms of inflammation are heat, redness, swelling, pain, and/or loss of function. These are manifestations of the physiologic changes that occur during the inflammatory process. The three major components of this process are: (1) changes in the caliber of blood vessels and the rate of blood flow through them (hemodynamic changes); (2) increased capillary permeability; and (3) leukocytic exudation. "Neutrophil-mediated inflammation" refers to the leukocytic exudation and stage of inflammation, in which neutrophils move to the endothelial lining of the small blood vessels (margination) and line the endothelium in a tightly packed formation (pavementing). Eventually, these neutrophils move through the endothelial spaces and escape into the extravascular space (emigration). Once they are outside the blood vessels they are free to move and, by chemotaxis, are drawn to the site of injury. Accumulations of neutrophils (and macrophages) at the area of inflammation act to neutralize foreign particles by phagocytosis.

Inflammation includes acute inflammation, which is usually of sudden onset, marked by the classical signs of heat, redness, swelling, pain, and loss of function, and in which vascular and exudative processes predominate; catarrhal inflammation, which is a form affecting mainly a mucous surface, marked by a copious discharge of mucus and epithelial debris; chronic inflammation, which is prolonged and persistent inflammation marked chiefly by new connective tissue formation; it may be a continuation of an acute form or a prolonged low-grade form; interstitial inflammation, which is inflammation affecting chiefly the stroma of an organ; traumatic inflammation, which is one that follows a wound or injury; ulcerative inflammation, in which necrosis on or near the surface leads to loss of tissue and creation of a local defect (ulcer).

Inflammation may be infectious and/or non-infectious. "Infectious" inflammation refers to inflammation that is associated with and/or is caused by the invasion and multiplication of microorganisms such as bacteria, viruses, and parasites that are not normally present within the body. In contrast, "non-infectious" inflammation refers to inflammation that is not associated with and/or is not caused by the invasion and multiplication of microorganisms such as bacteria, viruses, and parasites that are not normally present within the body.

In another embodiment, the present technology provides a method for treating neutrophil-mediated inflammation by targeting the pro-inflammatory MRP2/$HXA_3$ pathway (FIG. 10). In a particular embodiment, this method for treating neutrophil-mediated inflammation in a target tissue of a mammalian subject in need thereof, comprises administering to the subject a therapeutically effective amount of one or more first compound that inhibits the activity and/or level of one or more of multidrug resistance protein 2 (MRP2) and hepoxilin A3 ($HXA_3$) synthase, wherein the therapeutic amount of the first compound reduces migration of neutrophils into the target tissue. In some embodiments, the compound is a probenecid conjugate.

Determination of the Biological Effect of Probenecid Conjugates of the Present Technology In various embodiments, suitable in vitro or in vivo assays are performed to determine the effect of a specific composition of the present technology and whether its administration is indicated for treatment. In various embodiments, in vitro assays can be performed with representative cell-based assays, such as the neutrophil migration assay. In other embodiments, in vivo models, typified by animal models, may be used to determine if a given probenecid conjugate alone or in combination with one or more additional compounds (e.g., an additional compound that inhibitis one or more of MRP2 and $HXA_3$ synthase, a compound that increases the level and/or activity of MRP1, or a compound that increases NAEs), exerts the desired effect in treating a disease or condition. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

V. Combination Therapy with Probenecid Conjugates and Other Therapeutic Agents In some embodiments, the probenecid conjugates of the present technology may be combined with one or more additional therapeutic agents for the prevention, amelioration, or treatment of a disease or condition.

In one embodiment, an additional therapeutic agent is administered to a subject in combination with a probenecid conjugate of the present technology such that a synergistic therapeutic effect is produced.

In some embodiments, the probenecid conjugates of the present technology are combined with one or more compounds that increase levels of multidrug resistance protein 1 (MRP1) described above in Section IIIA.

In some embodiments, the probenecid conjugates of the present technology are combined with one or more additional compounds that inhibit one or more of multidrug resistance protein 2 (MRP2) and hepoxilin A3 ($HXA_3$) synthase described above in Section IIIB.

In some embodiments, the probenecid conjugates of the present technology are combined with one or more additional compounds that increase N-acylethanolamines (NAEs) described above in Section IIIC.

In some embodiments, the probenecid conjugates of the present technology are combined with one or more additional therapeutic agents for treating neutrophil-mediated inflammation and conditions associated therewith, including, but not limited to, ulcerative colitis and Crohn's disease. In some embodiments, the present technology provides compositions comprising one or more of a first compound that increases the level and/or activity of multidrug resistance protein 1 (MRP1), a second compound, such as a probenecid conjugate, that inhibits one or more of multidrug resistance protein 2 (MRP2) and hepoxilin A3 ($HXA_3$) synthase, and/or a third compound that increases one or more N-acylethanolamines (NAEs).

The multiple therapeutic agents (e.g., probenecid conjugates, compounds that increase the level and/or activity of MRP1, additional inhibitors of MRP2 and $HXA_3$ synthase, and/or compounds that increase NAEs) may be administered in any order or even simultaneously. If simultaneously, the multiple therapeutic agents may be provided in a single, unified form, or in multiple forms (by way of example only, either as a single formulation or as two separate formulations). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

In some embodiments, the methods of the present technology further comprise administering to the subject a therapeutically effective amount of at least one compound that increases the level and/or activity of one or more N-acylethanolamines (NAEs), wherein the therapeutic amount of the compound reduces migration of neutrophils into the target tissue.

While not intending to limit the type of compound that increases NAEs, in one embodiment, the compound that increases NAEs is a cannabinoid receptor type 2 (CB2) "agonist" (i.e., a compound that specifically binds to, and activates, CB2). CB2 agonists are exemplified by GW-405,833; AM-1241; HU-308; JWH-015; JWH-133; L-759,633; L-759,656; beta-caryophyllene; arachidonylcyclopropylamide; and arachidonyl-2'-chloroethylamide.

In some embodiments, the methods of the present technology may further comprise administering one or more antibiotic and/or anti-inflammatory agent. Examples of antibiotic/anti-inflammatory agents used singly or in combination in the methods of the present technology include, but are not limited to Dalbavancin (DALVANCE©, XYDALBA©), Oritavancin (ORBACTIVE©) Daptomycin (Cubicin©), Tedizolid (SIVEXTRO©), Ceftobiprole (ZEVTERA©, MABELIO©), Ceftobiprole (ZEVTERA©, MABELIO©), Ceftolozane-tazobactam (ZERBAXA©) mupirocin, neomycin sulfate bacitracin, polymyxin B, 1-ofloxacin, clindamycin phosphate, gentamicin sulfate, metronidazole, hexylresorcinol, methylbenzethonium chloride, phenol, quaternary ammonium compounds, tea tree oil, steroidal agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, betamethasone dipropionate, triamcinolone, non-steroidal agents such as COX inhibitors, LOX inhibitors, p38 kinase inhibitors, immunosuppresant agents such as cyclosporin, and cytokine synthesis inhibitors, tetracycline, minocycline, and doxycycline, or any combination thereof.

In some embodiments, the methods of the present technology may further comprise administering one or more antibodies, such as antibodies targeting one or more of *Clostridium difficile* toxins, tumor necrosis factor (TNF), interleukins, metalloproteinase-9 (such as the antibody GS-5745, Gilead).

In some embodiments, the present disclosure encompasses methods for the treatment, amelioration, or prevention of Crohn's disease, comprising administering one or more compounds of the present technology in combination with at least one or more mesalamine products, corticosteroid formulations, both conventional corticosteroids and ileal-release budesonide, glucocorticosteroids/EEN immunomodulatives (such as azathioprine, 6-mercaptopurine, and methotrexate), anti-tumor necrosis factor (TNF) drugs (such as infliximab (Remicade, Janssen), adalimumab (Humira, AbbVie), and certolizumab pegol (Cimzia, UCB)), the anti-alpha-4 beta-7 integrin antibody vedolizumab (Entyvio, Takeda), the JAK inhibitors ABT-494 (AbbVie), and filgotinib (GLPG0634, Galapagos and Gilead) (Sandborn, *Gastroenterology & Hepatology* 12(7) (2016)).

In some embodiments, the present disclosure encompasses methods for the treatment, amelioration, or prevention of ulcerative colitis, comprising administering one or more compounds of the present technology in combination with at least one or more of 5-aminosalycylates, mesalamine, conventional corticosteroids or multimatrix budesonide (Uceris, Salix), which delivers the drug to the colon, azathioprine, 6-mercaptopurine, anti-TNF drugs (such as infliximab, adalimumab, and golimumab (Simponi, Janssen)), vedolizumab, Janus kinase (JAK) inhibitors (e.g., Tofacitinib (Xeljanz, Pfizer) ABT-494 (AbbVie), and filgotinib (GLPG0634, Galapagos and Gilead)) (Sandborn, 2016).

VI. Modes of Administration

Any method known to those in the art for contacting a cell, organ, or tissue with compounds of the present technology may be employed. Suitable methods include in vitro, ex vivo, or in vivo methods.

In vitro methods typically include cultured samples. For example, a cell can be placed in a reservoir (e.g., tissue culture plate), and incubated with a compound under appropriate conditions suitable for obtaining the desired result. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are typically returned to the donor, placed in a recipient, or stored for future use. Thus, the compound is generally in a pharmaceutically acceptable carrier.

In vivo methods typically include the administration of a compound of the present technology to a mammal such as a human. When used in vivo for therapy, a compound of the present technology is administered to a mammal in an amount effective to obtain the desired result, e.g., of treating the mammal. The effective amount is determined during pre-clinical trials and clinical trials by methods familiar to physicians and clinicians. The dose and dosage regimen will depend upon the degree of the disease or condition in the subject, the characteristics of the particular compound of the present technology used, e.g., its therapeutic index, the subject, and the subject's history.

An effective amount of a compound of the present technology useful in the present methods, such as in a pharmaceutical composition or medicament, may be administered to a mammal in need thereof by any of a number of well-known methods for administering pharmaceutical compositions or medicaments. The compounds of the present technology may be administered systemically or locally.

The compounds of the present technology described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

In some embodiments, the pharmaceutical compositions of the present disclosure contain a pharmaceutically acceptable carrier and/or excipient suitable for rendering the compound or mixture administrable orally as a tablet, capsule or pill, or parenterally, intravenously, intradermally, intramuscularly or subcutaneously, or transdermally.

Pharmaceutical compositions are typically formulated to be compatible with the intended route of administration. Administering the pharmaceutical composition of the present disclosure may be accomplished by any means known to the skilled artisan. Routes of administration include, but are not limited to, parenteral, intravenous, intramuscular, intradermal, intraperitoneal, intratracheal, subcutaneous, oral, intranasal/respiratory (e.g., inhalation), transdermal (topical), sublingual, ocular, vaginal, rectal, and transmucosal administration. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In some embodiments, administration is topical and/or at the luminal surface of the tissue to be treated. "Topical" administration of a composition means contacting the composition with the skin. "Luminal surface" refers to the inner open space or cavity of a tubular organ, such as the interior central space in an artery or vein through which blood flows; the interior of the gastrointestinal tract; the pathways of the bronchi in the lungs; the interior of renal tubules and urinary collecting ducts; the pathways of the female genital tract, starting with a single pathway of the vagina, splitting up in two lumina in the uterus, both of which continue through the fallopian tubes.

In some embodiments, the compounds of the present technology are administered topically and/or at a luminal surface of the target tissue. This is advantageous to reduce potential systemic toxic side effects of the compounds.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the disclosure is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

VII. Methods for Delivering Nucleic Acids to Cells

In some embodiments, an inhibitory oligonucleotide (e.g., interfering RNA) and or a protein can be delivered to the cells via an expression vector engineered to express the inhibitor oligonucleotide and or a protein. An expression vector is one into which a desired sequence may be inserted, e.g., by restriction and ligation, such that it is operably joined to regulatory sequences and may be expressed as an RNA transcript. An expression vector typically contains an insert that is a coding sequence for a protein or for an inhibitory oligonucleotide such as an shRNA, a miRNA, or an miRNA. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays or fluorescent proteins, etc.

As used herein, a coding sequence (e.g., protein coding sequence, miRNA sequence, shRNA sequence) and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence may encode an miRNA, shRNA, or miRNA.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses, a modified retrovirus, a nonreplicating retrovirus, a replication defective Semliki Forest virus, canarypox virus and highly attenuated vaccinia virus derivative, non-replicative vaccinia virus, replicative vaccinia virus, Venzuelan equine encephalitis virus, Sindbis virus, lentiviral vectors and Ty virus-like particle.

Another virus useful for certain applications is the adeno-associated virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, New Jersey (1991). In some embodiments, an epigenetic modulator of DUX4 (e.g., an interfering RNA or a gene editing complex) is delivered to a cell (e.g. a cell of a subject) by a lentiviral vector.

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect GeneJuice® Transfection Reagent by Novagen.

EXPERIMENTAL EXAMPLES

The present technology is further illustrated by the following examples, which should not be construed as limiting in any way.

Example 1: Materials and Methods

The following is a brief description of the exemplary materials and methods used in the subsequent Examples.

Human cell lines. T84 intestinal epithelial cells at passages 50-79 (American Type Culture Collection, Rockville, Maryland) were grown in a mixture of Dulbecco's Modified Eagles Medium and Ham's F12 Nutrient mixture supplemented with 14 mM $NaHCO_3$, 15 mM Hepes buffer (pH 7.5), 40 mg/liter penicillin, 8 mg/liter ampicillin, 90 mg/liter streptomycin, and 5% heat-inactivated fetal bovine serum (FBS). HCT-8 colon carcinoma cells (ATCC) and H292 lung epithelial carcinoma cells (ATCC CRL 18-48) were grown in RPMI-1640 with 10% heat inactivated FBS.

*Salmonella* infection of HCT-8 epithelial cells. HCT-8 cell monolayers were grown and maintained on inverted 0.33-$cm^2$ ring-supported, collagen-coated 5 μm pore polycarbonate filters (Costar Corp., Cambridge, MA). Cells were treated apically and basolaterally with probenecid conjugate at 100 μM in Hanks buffered salt solution with $Ca^{2+}$ and $Mg^{2+}$ (HBSS+/+) and incubated for 1 hour at 37° C. Following washing, cells were infected apically with *Salmonella enterica* serovar *Typhimurium* strain SL1344 at an MOI of 375 for 1 hour. Following extensive washing, neutrophils ($1\times10^6$) were added to the basolateral surface and allowed to transmigrate through the monolayer for 2 hr, and quantified as described below.

Production of enriched Hepoxilin A3. *P. aeruginosa* strain PA01 was grown aerobically in LB broth overnight at 37° C. Cultures were washed once in HBSS+/+ and resuspended at a concentration of $6\times10^7$ bacteria/mL. H292 monolayers in 162 $cm^2$ flasks were infected for 1 hr, washed with HBSS, and then incubated in HBSS+/+ for 5 hours. Collected supernatants were captured by reversed-phase chromatography on octadecylsilane (C18) columns (Supelco), washed with water, and eluted with methanol. Samples were stored at −20° C. and the volume necessary for individual experiments dried down and resuspended in HBSS+/+ as needed. Each new batch of enriched $HXA_3$ was quality tested before use in experiments, and were generally used at a concentration of 1:4 to 1:8.

Generation of P-gp knockdown T84 cell lines. Purified DNA containing shRNA constructs targeting the mdr1a gene in a pLK0.1 plasmid background was obtained from the UMass RNAi core. Constructs were as follows: B4 (Clone ID: TRCN0000059683), B5 (Clone ID: TRCN0000059684), B6 (Clone ID: TRCN0000059685), B7 (Clone ID: TRCN0000059686), B8 (Clone ID: TRCN0000059687). Lentiviruses were produced by transfecting packaging cells (293T) with psPAX2, pMD.2G, and pLK0.1 plasmid constructs, using Trans-IT-LT1 lipid (Mirus Bio). After 48 hours, lentiviral supernatants were harvested, combined with 8 μg/mL polybrene (Sigma-Aldrich) and applied to T84 cells in 20% confluent monolayers. This process was repeated 24 hours later, and 48 hours following the second transfection, resistant cells were selected with 5 μg/mL puromycin. Once stable transfectant lines were obtained, reduction of P-gp expression was confirmed by Western blot using anti-P-gp monoclonal antibody C219 (EMD Millipore).

Production of enriched AMEND. T84 cells were grown as confluent monolayers in 162 $cm^2$ flasks and equilibrated in Hanks Buffered Saline Solution with $Mg^{2+}/Ca^{2+}$ (HBSS+/+) at 37° C., 5% $CO_2$. For verapamil treatment of cells, 40 μM verapamil hydrochloride (Sigma) was included during the entire incubation. Cell supernatants collected over the course of five hours were pooled from 30 flasks, lyophilized, resuspended in water and ultrafiltered through Amicon 1,000-Da cutoff membrane (Millipore) with $N_2$ positive pressure. Samples were captured on a C18 Bakerbond® SepPak column, washed with water and hexane, eluted with methanol, dried under $N_2$ gas and stored at −80° C. Before use in migration experiments, samples were resuspended in HBSS+/+ as needed. For screening in the DiscoveRx GPCR β-arrestin activity assay (Fremont, CA), samples were resuspended in PBS to provide a 1000× solution for screening.

96-well neutrophil migration. All studies were performed in accordance with University of Massachusetts Medical School Human Subjects IRB approval. Peripheral blood neutrophils were purified from acid citrate dextrose anti-coagulated peripheral blood by 2% gelatin sedimentation as previously described (Hurley, B. P. et al., *J. Immunol.* 173:5712-5720 (2004)). Red blood cells were removed by lysis in cold $NH_4Cl$ buffer, and neutrophils were washed with HBSS−/− (without $Ca^{2+}$ or $Mg^{2+}$) and resuspended to a final volume of $5\times10^7$/mL. 96 well HTS transwell filter plates (Corning), 3 μm pore size, were coated with 0.1 mg/mL rat tail collagen and allowed to dry overnight. Enriched $HXA_3$ (see above) was added to the lower well along with 1:10 dilution of vehicle control, enriched AMEND (see below), or purified endocannabinoid compounds at the indicated concentrations. $5\times10^5$ neutrophils were added to the top well along with 1:10 vehicle or purified endocannabinoids, placed in a 37° C. incubator with 5% $CO_2$ and allowed to migrate for 2 hr. Top wells were removed, and transmigrated neutrophils were lysed with 1% Triton-X100. Sodium Citrate buffer (pH 4.2) was added to 0.1 M, and an equal volume of 2,2'-azino-bis(3-ethylbenzothiazoline-6-sulphonic acid) (ABTS) in 0.1 M Sodium citrate was added to samples. Myeloperoxidase (mpo) activity was measured. Neutrophil cell equivalents were calculated by comparison with a standard curve, and data from individual experiments were normalized to 100% $HXA_3$ migration. Data are mean+/−SEM from at least three independent experiments. Statistical analysis was performed using GraphPad Prism; data were analyzed by either one-way ANOVA or Mann-Whitney non-parametric U test as appropriate for experimental conditions.

Purified compounds used in migration assays. All compounds were obtained from Cayman Chemical (Ann Arbor, MI), and resuspended at the highest concentration at which they were soluble in PBS, based on the manufacturer's instruction and empirical observation, and were then diluted 1:10 to reach the final concentrations indicated:

Arachidonoyl ethanolamide (AEA), CAS No. 94421-68-8, was used at 0.01 mg/mL.

α-Linolenoyl Ethanolamide (α-LEA), CAS No. 57086-93-8, was used at 0.005 mg/mL.

Linoleoyl Ethanolamide (LEA), CAS No. 68171-52-8, was used at 0.0001 mg/mL.

γ-Linolenoyl Ethanolamide (γ-LEA), CAS No. 150314-37-7, was used at 0.0001 mg/mL.

2-arachidonoyl glycerol (2-AG), CAS No. 53847-30-6, was used at 0.01 mg/mL.

2-linoleoyl glycerol (2-LG), CAS No. 3443-82-1, was used at 0.01 mg/mL.

2-(14,15-Epoxyeicosatrienoyl) Glycerol, CAS No. 848667-56-1, was used at 0.005 mg/mL.

N-arachidoyl ethanolamide (NAE), CAS No. 94421-69-9, was used at 0.005 mg/mL.

O-Arachidonoyl ethanolamine (O-AEA), CAS No. 443129-35-9, was used at 0.001 mg/mL.

Noladin ether (NE), CAS No. 222723-55-9, was used at 0.001 mg/mL.

12-Hydroxyeicosatetraenoic acid (12-HETE), CAS No. 71030-37-0, was used at 0.005 mg/mL.

20-HETE Ethanolamide (20-HETE Eth), CAS No 942069-11-6, was used at 0.005 mg/mL.

Oleoyl ethanolamide (OEA), CAS No. 111-58-0, was used at 0.01 mg/mL.

2 palmitoyl glycerol (2-PG), CAS No. 23470-00-0, was used at 0.05 mg/mL.

2-oleoyl glycerol (2-OG), CAS No. 3443-84-3, was used at 0.002 mg/mL.

Palmitoyl ethanolamide (PEA), CAS No. 544-31-0, was used at 0.0000005 mg/mL.

Arachidonic acid, peroxide free formulation (pfAA), CAS No. 506-32-1, was used at 0.125 mg/mL.

LC/MS analysis of AMEND. MeOH-eluted preparations as above were dried under a stream of $N_2$ (g), re-suspended in MeOH/buffer and separated by HPLC using a Vydac (Hesperia, CA) C18 (10 um; 300 Å) semi-preparative column (10×250 cm). Active AMEND fractions were characterized by HPLC/Mass spectrometry (Genesis C18 (4 um, 120 Å) analytical HPLC column (4.6×150 mm) equilibrated with 5 mM triethylamine acetic acid (pH 7.2) with the effluent analyzed by using a Finnigan LCQDeca electrospray mass spectrometer.

Selected samples were analyzed for high mass accuracy determination and solubilized in 50:50 acetonitrile:$H_2O$ with 0.2% formic acid. A MAXIS-HD ultra-high resolution quadrupole time-of-flight (UHR-ESI-QTOF) mass spectrometer (Bruker Daltonik GmbH, Bremen, Germany) was used; this was coupled to a syringe driver (Hamilton, Bonaduz, Switzerland) with the sample solution being infused at a rate of 3 μL/min.

Nitrogen acted as the nebulizing gas, applied at a pressure of 2 bar. The drying gas was also nitrogen, supplied at a flow rate of 8 L/min and a temperature of 200° C. Positive ion mode was used with a corresponding capillary voltage of −4500V. Only full scan data was acquired. For each batch of samples a solution of 5 mM sodium formate clusters was also analysed. This acted as an external data file calibrant over the mass range 75-1000 m/z. The recalibrated detected mass and isotope pattern were used in the FindFormula tool to generate a list of potential theoretical formulae within 2 mDa of the detected mass. The detected isotope pattern was used to sort this list.

Data acquisition and automated processing was controlled via Compass OpenAccess 1.7 software (Bruker Daltonik GmbH, Bremen, Germany), and data processing was carried out using DataAnalysis 3.4 (Bruker Daltonik GmbH, Bremen, Germany). At each step care was taken to avoid sample degradation and oxidation by maintaining them on ice and under $N_2$ gas as much as possible. Relative quantification by ion intensities was performed by the summation of intensities for protonated and sodiated ions to compensate for possible variation in adduct formation due to varying biological sodium levels.

Mouse experiments. C57BL/6 and cnr2−/− mice were purchased from Jackson laboratories; FVB wt and mdr1a−/− were purchased from Taconic. Female mice were used at age 6-12 weeks, and genotypes were mixed for at 2-4 weeks prior to experiments to equalize the microbiota. Mice were treated with 3% DSS (molecular weight 36,000-50,000, MP Biomedicals) in the drinking water for 7 days, then placed back on normal water and sacrificed at day 9, which represented peak disease. Samples from mid and distal colon were fixed in 10% formalin, paraffin-embedded, sectioned, and stained for histopathological analysis with hematoxylin and eosin. Each sample was graded semi-quantitatively from 0 to 3 for four criteria: (1) degree of epithelial hyperplasia and goblet cell depletion; (2) leukocyte infiltration in the lamina propria; (3) area of tissue affected; and (4) the presence of markers of severe inflammation such as crypt abscesses, submucosal inflammation, and ulcers. Samples were scored by a trained investigator blinded to sample identity, and mid and distal values were averaged to give colon histopathology score.

Isolation of lamina propria leukocytes and flow cytometry. Cell suspensions from the lamina propria were prepared as described previously (Buonocore et al., 2010). Intestinal tissue was cut into small pieces, treated with RPMI with 10% FBS and 5 mM EDTA to remove epithelial cells, and then incubated with 100 U/mL Collagenase Type VIII (Sigma-Aldrich) for two 1 hr periods. Cells were then applied to a discontinuous 30/40/75% gradient of Percoll (GE Healthsciences) and harvested from the 40/70% interface. Cells were washed in PBS/0.1% BSA, incubated with anti-Fc receptor (αCD16/32, eBioscience) and stained with Zombie Live/Dead infrared stain (eBioscience), then surface stained with antibodies to CD45, CD11b, Ly6G, and Ly6C or Gr1. Samples were run on a MACSquant Analyzer 10 (Miltenyi Bioscience) and analyzed using Flowjo software Version 10 (Treestar).

Analysis of myeloperoxidase content in mouse samples. Samples were assayed for myeloperoxidase activity as described (see, e.g. Pulli, B. et al. *PLOS One* 8, e67976 (2013)). Tissue sections of colon were frozen in liquid $N_2$ and stored at −80° C. until use. Sections were put in hexadecyl trimethyl ammonium bromide (HTAB, Sigma) buffer with lysing matrix D (MP Biomedicals) and homogenized with a FastPrep-24 homogenizer at level 6 for 40 s. Samples were combined with ABTS and fluorescence read over 8 min. Slopes were calculated by linear regression using Graphpad Prism, and normalized to protein content for individual samples as measured by Bicinchonic Acid assay (BioRad). For analysis of fecal samples, fecal contents were weighed and HTAB buffer added at a ratio of 10 μL/mg, and calculated slopes were used directly.

Mass Spectrometric Analysis of $HXA_3$ in colonic mucosa. Mice were administered 5% DSS in their drinking water and sacrificed on day 7. The proximal colon from untreated or DSS-treated mice (9 mice/cohort) was harvested and three intestinal segments were pooled. Mucosal scrapings were collected by scraping intestinal surfaces with a rubber policeman in PBS, and $HXA_3$ content was analyzed as previously described (Mumy, K. L. et al., *Infect. Immun.* 76:3614-27 (2008).

Example 2: Synthesis of Probenecid Conjugates

An illustrative example of the general synthesis of a dextran-probenecid conjugate is shown in Scheme 1.

Scheme 1.

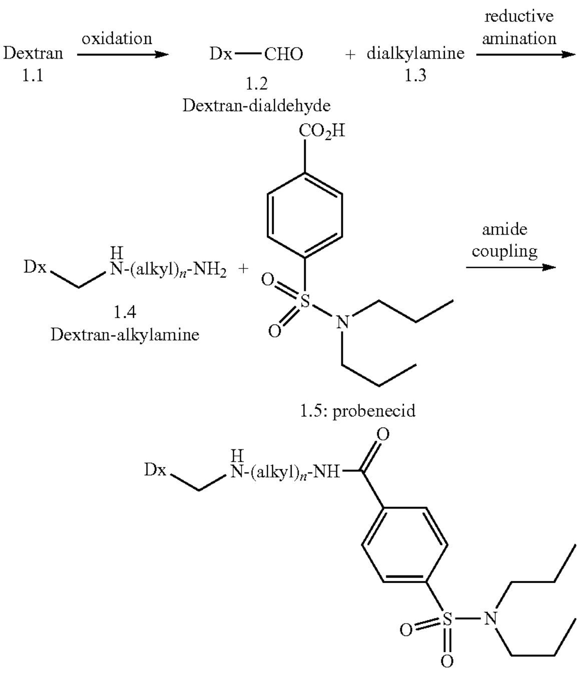

Dextran 1.1

1.2 Dextran-dialdehyde dialkylamine 1.3

1.4 Dextran-alkylamine 1.5: probenecid 1.6 Dextran-probenecid conjugate

General description for synthesis of dextran-probenecid conjugates. Dextran 1.1 is a polysaccharide. Its average molecular weight typically ranges from about 1000 daltons to about 1,000,000 daltons. Oxidation of dextran diol functionality produces dextran-dialdehyde 1.2. Oxidants used for the oxidation include sodium and potassium periodate. Water or alcohol water mixtures are used as solvent for the oxidation reaction. Literature preparations for dextran-dialdehyde 1.2 include that of Hicks & Molday, Invest. Opthalmol. 26:1002-1013 (1985).

Dextran aldehyde 1.2 readily undergoes reductive amination with alkyldiamines 1.3 to yield a dextran-alkyldiamine 1.4. The reaction is carried out by contacting 1.2 with excess of an alkyldiamine 1.3 in the presence of a reducing agent in a suitable solvent. An example of an alkyldiamine is hexyldiamine. Reagents to carry out reductive amination include sodium borohydride and sodium cyanoborohydride. Solvents typically used are water and alcohol-water mixtures with pH maintained between pH 5.5 and 8.5. The resulting dextran-alkylamine 1.4 amine substitution level is about 5% to about 70% depending on the reaction conditions. For the methods described herein, the method of Hicks & Molday (1985) was employed to prepare 1.4 from dextran.

As shown in Scheme 1, dextran-alkyldiamine 1.4 is coupled to probenecid 1.5 to produce dextran-probenecid conjugate 1.6, wherein n may be any integer from 1 to 10. The coupling reaction is an amide-bond forming reaction taking place between the terminal primary amino group of the dextran-alkyldiamine 1.4 and the carboxylic acid group of probenecid 1.5. The carboxylic acid group is first activated by a variety of reagents. Activating reagents include, but are not limited to, dicyclohexylcarbodiimide (DCC), diisopropylcarbodiimide (DIC), ethyl-(N',N'-dimethylamino)propylcarbodiimide hydrochloride (EDC), (benzotriazol-1-yloxy)tris(dimethylamino)phosphonium hexafluorophosphate (BOP), (benzotriazol-1-yloxy) tripyrrolidinophosphonium hexafluorophosphate (PyBOP), (7-azabenzotriazol-1-yloxy)tripyrrolidinophosphonium hexafluorophosphate (PyAOP), bis(2-oxo-3-oxazolidinyl) phosphinic chloride (BOP-chloride), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), and carbonyldiimidazole (CDI). Solvents used to conduct the coupling reaction include, but are not limited to, methylene dichloride, ether, ethyl acetate, toluene, and tetrahydrofuran. Typical reaction times range from about 15 min up to about 12 hours. The reaction progress can be monitored by proton NMR. Amide coupling can result in about 5% to about 95% of the polymer amine derivatization. Analytical characterization includes direct measurement of free amine remaining (extent of coupling reaction) and measurement of probenecid coupled product by proton NMR, mass spectrometry, or other suitable analytical technique.

Synthesis of a Dextran-Probenecid Conjugate:

Scheme 2.

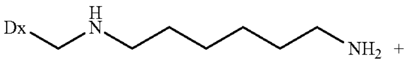

1.1A: Dextran-hexylamine (40 KDa)
1.1B: Dextran-hexylamine (10 KDa)

-continued

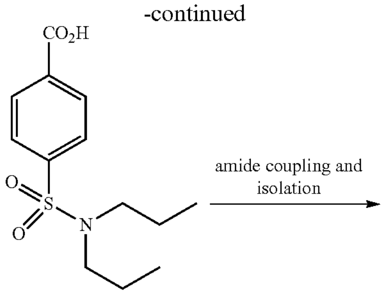

1.2: probenecid

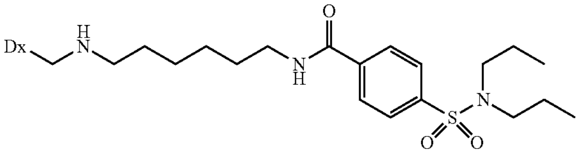

Dextran-probenecid conjugate
(Dx-probenecid)
1.3A = 40 KDa
1.3B = 10 KDa

Preparation of dextran-probenecid conjugate 1.3A. 40-kDa dextran-hexylamine (0.5 g, 0.263 mmoles $NH_2$) was dissolved in 20 mL of MES buffer and probenecid (112 mg, 1.5-fold molar excess) was added. The reaction mixture, pH 6.25, was vigorously stirred at room temperature to yield a clear solution. 1-Ethyl-3-(3-dimethylaminopropyl)carbodiimide (EDC; 200 mg) was added and the reaction mixture was stirred for 15 min. The reaction mixture was transferred to a dialysis tube (15 kDa membrane). Following dialysis, the Dx-probenecid 1.3A was isolated as a dry powder by lyophilization. Probenecid conjugate 1.3B is prepared by the same method using 10-kDa dextran-hexylamine 1.1B.

Alternative Synthesis of Dextran-Probenecid Conjugate:

Scheme 3.

Step A

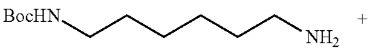

2.1

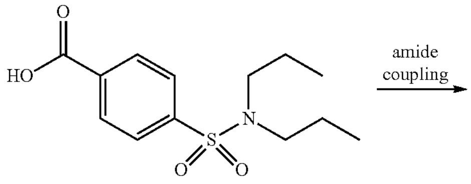

1,2: probenecid

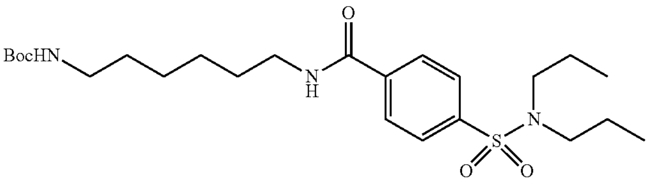

2.2

-continued

Step B

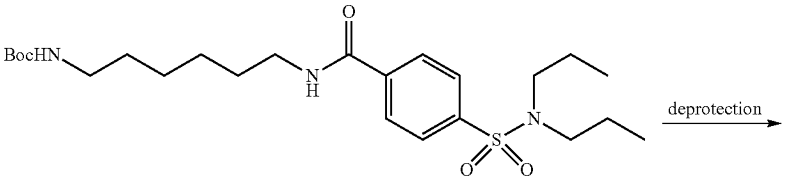

2.2

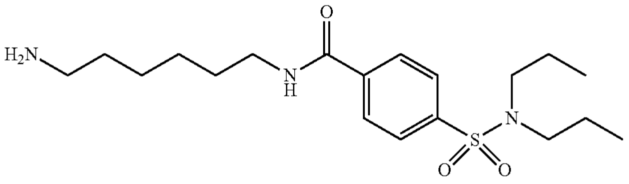

2.3

Step C

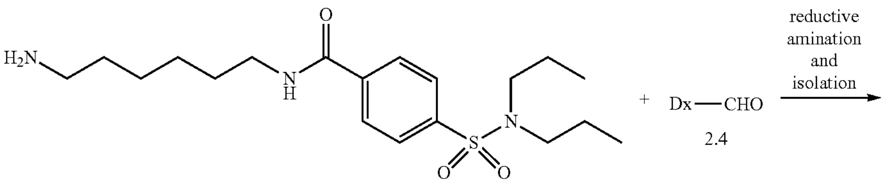

2.3

2.4

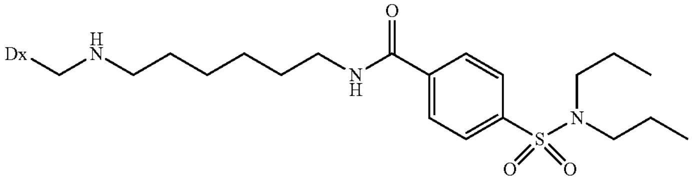

2.5

Preparation of dextran-probenecid conjugate 2.5. Mono-Boc hexane diamine 2.1 (CAS #51857-17-1; 1 gram) and probenecid 1.2 (1.5 molar equivalents) are dissolved in methylene dichloride (15 mL). Dicyclohexylcarbodiimide (1.5 molar equivalents) is added and the reaction mixture is stirred for 3 hours. The solution is filtered to removed discyclohexylurea and the solvent is removed on a rotary evaporator. The residue is purified by silica gel chromatography to provide 750 mg of Boc-amide 2.2. The compound is characterized by NMR and mass spectrometry analysis.

Trifuloroacetic acid (1 mL) is added to a solution of Boc-amide 2.2 (500 mg) in methylene dichloride (10 mL). The reaction mixture is stirred for 2 hours and the solvents removed on a rotary evaporator. The residue is dissolved in ethyl acetate and is washed with saturated aqueous sodium bicarbonate solution. The organic solvent is dried over solid sodium sulfate, filtered and the ethyl acetate solvent is removed using a rotary evaporator to give amine 2.3. Compound 2.3 is obtained in quantitative yield and does not require any further purification. The compound is characterized by NMR and mass spectrometry analysis.

Dextran aldehyde 2.4 (500 mg) is dissolved in an aqueous solution of sodium borate (5 mL of a 400 mM solution, pH 8.5). Probenecid aminohexylamide 2.3 (5 molar equivalents previously dissolved in 2 mL of methanol) is added followed by the addition of a freshly prepared aqueous solution of sodium cyanoborohydride (10 molar equivalents of a 3 molar aqueous solution). The reaction mixture is stirred for 4 hours at 25° C. The reaction mixture is transferred to a dialysis bag and is dialyzed against water for 24 hours (2 exchanges of water, 1 L each). The contents of the dialysis bag are transferred to a glass vial and the solution lyophilized to obtain polymer conjugate 2.5. The compound is characterized by NMR and mass spectrometry analysis.

Synthesis of Glycidal-Based Dextran-Probenecid Conjugate:

Scheme 4.

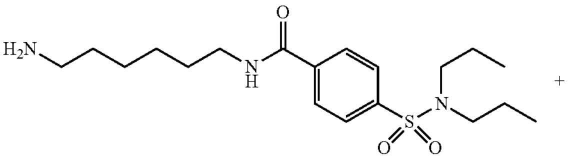

2.3

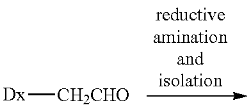

3.1

-continued

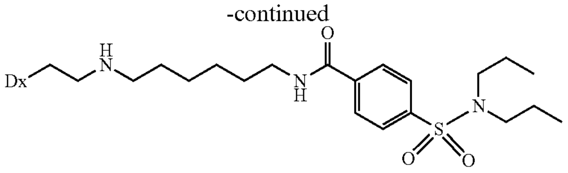

3.2

Preparation of dextran-probenecid conjugate 3.2. Dextran aldehyde polymer 3.1 (500 mg) is dissolved in an aqueous solution of sodium borate (5 mL of a 400 mM solution, pH 8.5). Probenecid aminohexylamide 2.3 (5 molar equivalents previously dissolved in 2 mL of methanol) is added followed by the addition of a freshly prepared aqueous solution of sodium cyanoborohydride (10 molar equivalents of a 3 molar aqueous solution). The reaction mixture is stirred for 4 hours at 25° C. The reaction mixture is transferred to a dialysis bag and is dialyzed against water for 24 hours (2 exchanges of water, 1 L each). The contents of the dialysis bag are transferred to a glass vial and the solution lyophilized to obtain polymer conjugate 3.2. The compound is characterized by NMR and mass spectrometry analysis.

Synthesis of PEG-Probenecid Conjugate:

Scheme 5

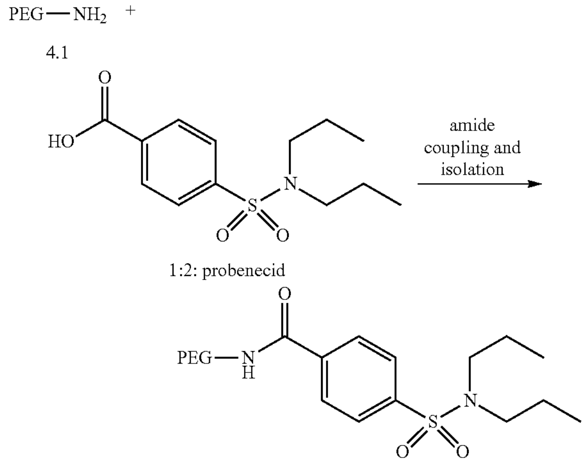

4.1

1:2: probenecid 4.2

Preparation of dextran-probenecid conjugate 4.2. A 25 mL round-bottom flask fitted with a stir bar is charged with an aqueous solution of 0.1 M 2-(N-morpholino)ethanesulfonic acid (MES buffer, pH 6.0) (10 mL) and PEG amine 4.1 (40,000 MW 2-arm branched PEG amine; NOF Corporation catalog no. SUNBRIGHT®GL2-400PA; 500 mg). Probenecid 1.2 (3 molar equivalents) is added and the reaction mixture is stirred vigorously until a clear solution is obtained. 1-Ethyl-3-(3-dimethylaminopropyl)carbodiimide (3 molar equivalents) is added and the reaction mixture is stirred for 30 minutes. The reaction mixture is transferred to a dialysis bag and is dialyzed against water for 24 hours (2 exchanges of water, 1 L each). The contents of the dialysis bag are transferred to a glass vial and the solution lyophilized to obtain polymer conjugate 4.2. The compound is characterized by NMR and mass spectrometry analysis.

Synthesis of additional PEG-probenecid conjugates. Similar to Scheme 5 and Scheme 3, a variety of PEG conjugates of probenecid may be prepared using various derivatives of PEG using either amide coupling or reductive amination. These are depicted in the following Schemes 6-19

Scheme 6.

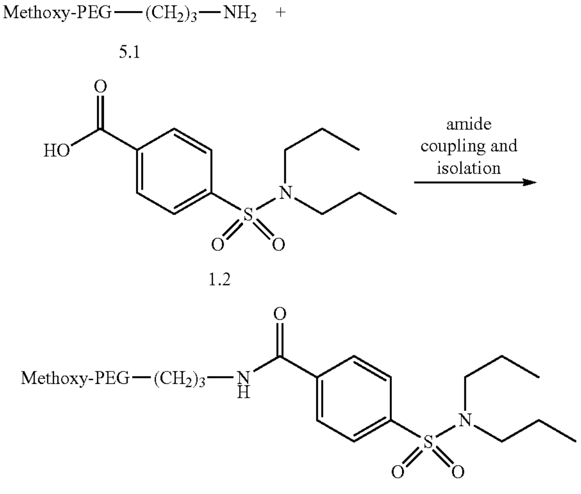

5.1

1.2

5.2

Molecular Weight: 5,000
Chemical Name: α-Aminopropyl-ω-methoxy, polyoxyethylene
CAS#: 116164-53-5
NOF catalog #: SUNBRIGHT MEPA-20H Scheme 7.

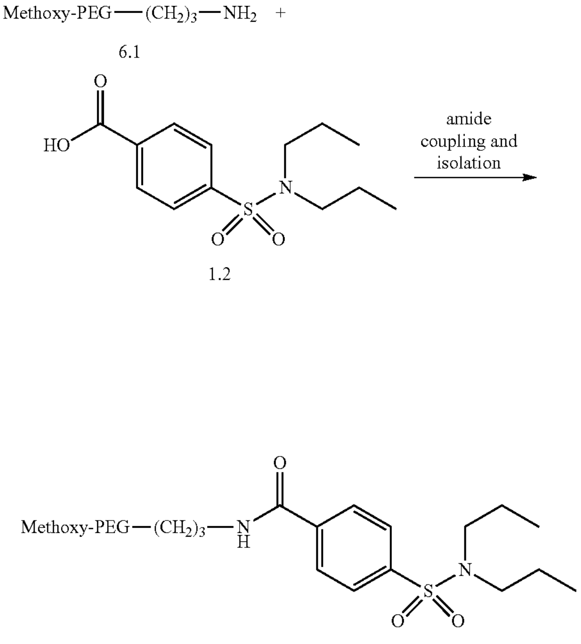

6.1

1.2

6.2

Molecular Weight: 40,000
Chemical Name: α-Aminopropyl-ω-methoxy, polyoxyethylene
CAS#: 116164-53-5
NOF catalog #: SUNBRIGHT MEPA-40T Scheme 8.
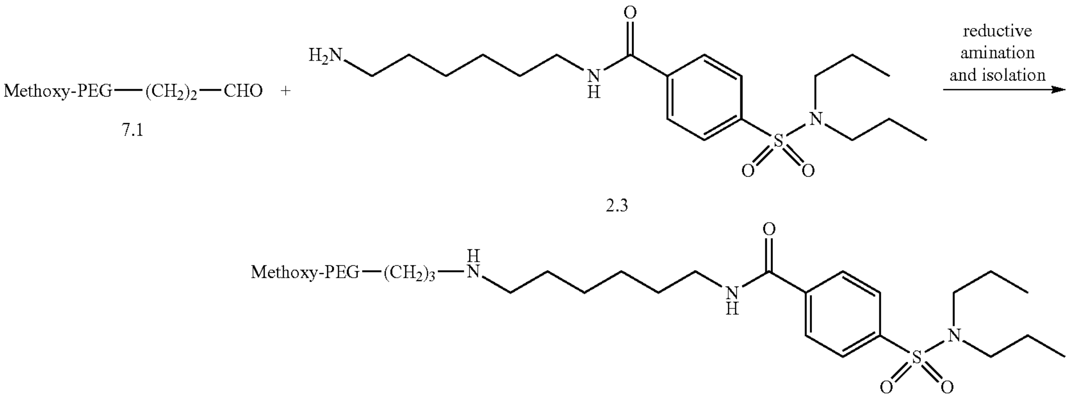
7.1
2.3
7.2
Molecular Weight: 5,000
Chemical Name: α-Methoxy-ω-(3-oxopropoxy), polyoxyethylene
CAS#: 125061-88-3
NOF catalog #: SUNBRIGHT ME-050AL
Scheme 9.
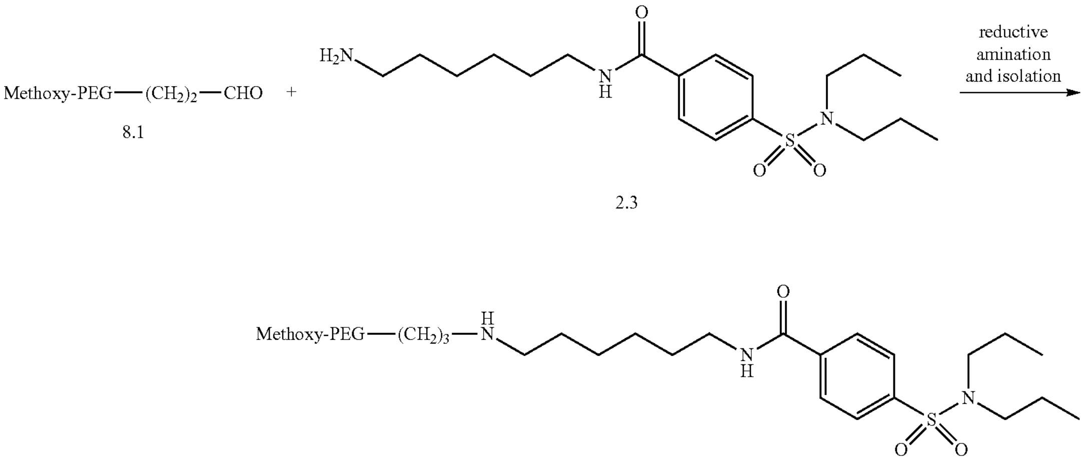
8.1
2.3
8.2
Molecular Weight 40,000
Chemical Name: α-Methoxy-ω-(3-oxopropoxy), polyoxyethylene
CAS#: 125061-88-3
NOF catalog #: SUNBRIGHT ME-400AL2
Scheme 10.
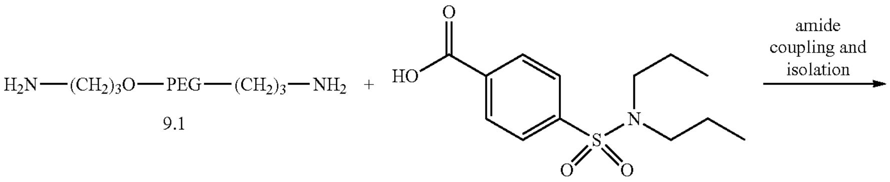
9.1
1.2

-continued
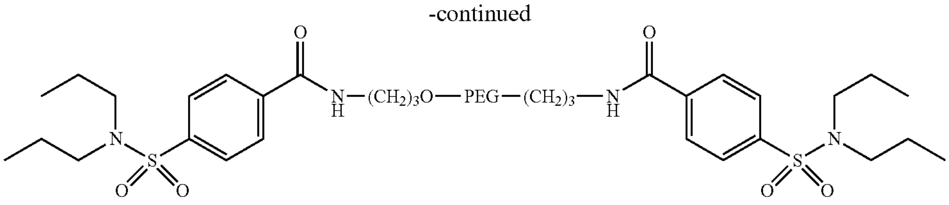
9.2
Molecular Weight 5,000
Chemical Name: α-Aminopropyloxy-ω-(aminopropyloxy), polyoxyethylene
CAS#: 25322-68-3
NANOCS catalog #: PG2-AM-5K
Scheme 11.
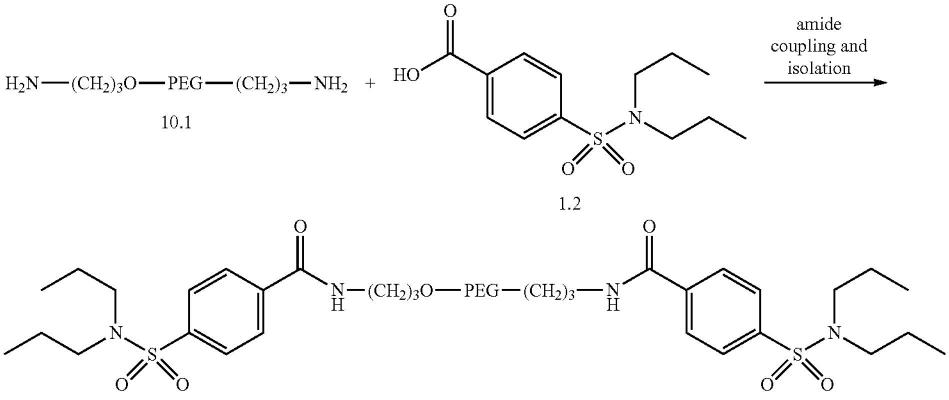
10.1
1.2
10.2
Molecular Weight 30,000
Chemical Name: Di-(α-Aminopropyloxy-ω-(3-oxopropoxy), polyoxyethylene
CAS#: 25322-68-3
NOF catalog #: SUNBRIGHT DE-300PA
Scheme 12.
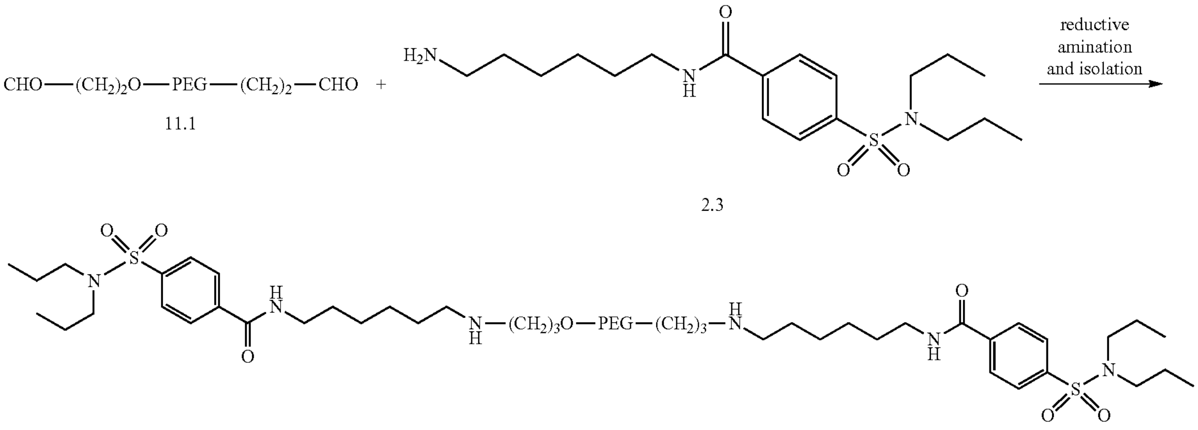
11.1
2.3
11.2
Molecular Weight 5000
Chemical Name: α-Oxoproxy-ω-(3-oxopropoxy), polyoxyethylene
NANOCS catalog #: PG2-AL-5k Scheme 13.
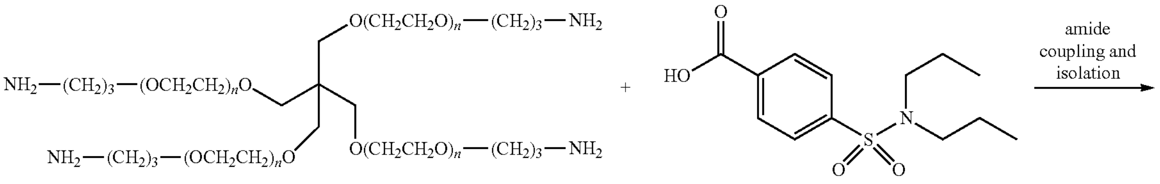
12.1
1.2
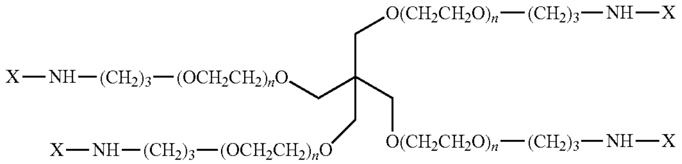
12.2
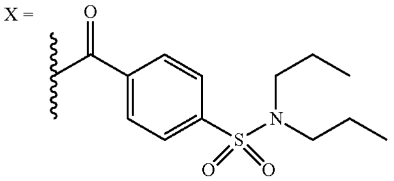
4-arm PEG, —((CH$_2$)$_3$—NH$_2$)
Molecular Weight: 10,000
Chemical Name: Pentaerythritol tetra(aminopropyl) polyoxyethylene
CAS#: 804514-67-8
NOF catalog #: SUNBRIGHT HGEO-100PA
Scheme 14.
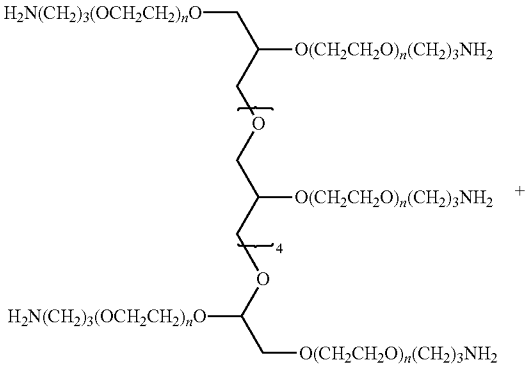
13.1
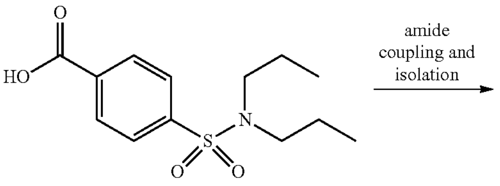
1.2
-continued
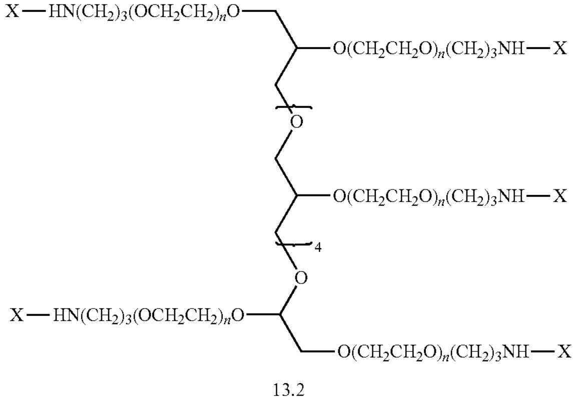
13.2
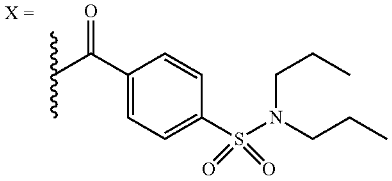
8-arm PEG, —((CH$_2$)$_3$—NH$_2$)$_8$
Molecular Weight: 15,000
Chemical Name: Hexaglycerol octa(aminopropyl) polyoxyethylene
NOF catalog #: SUNBRIGHT HGEO-150PA Scheme 15.
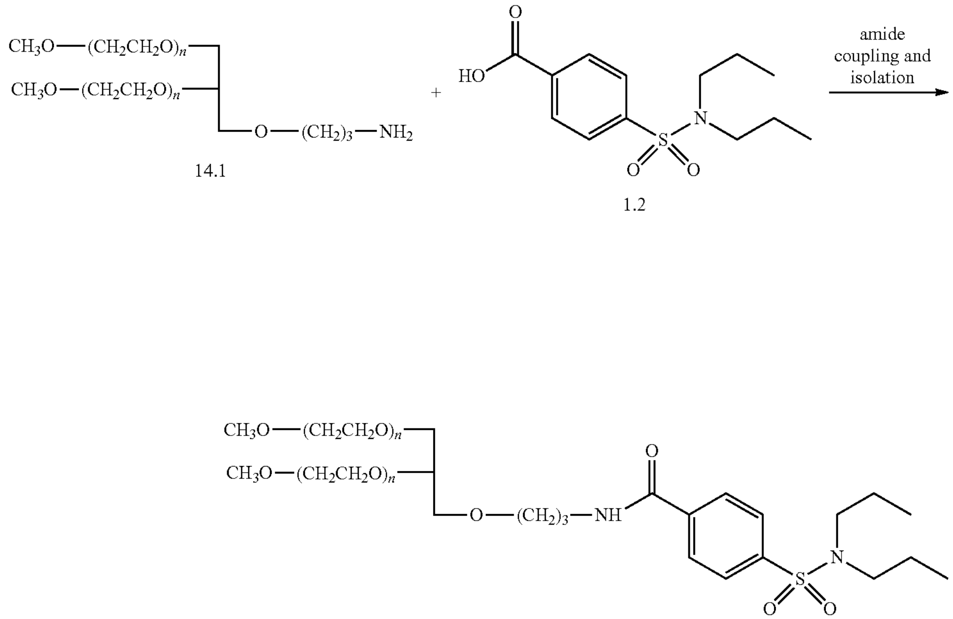
14.1
1.2
14.2
2-arm branched PEG, ——$(CH_2)_3$——$NH_2$
Molecular Weight: 40,000
Chemical Name: 2,3-Bis(methylpolyoxyethylene-oxy)-1-(aminopropyloxy) propane
NOF catalog #: SUNBRIGHT GL2-400PA
Scheme 16.
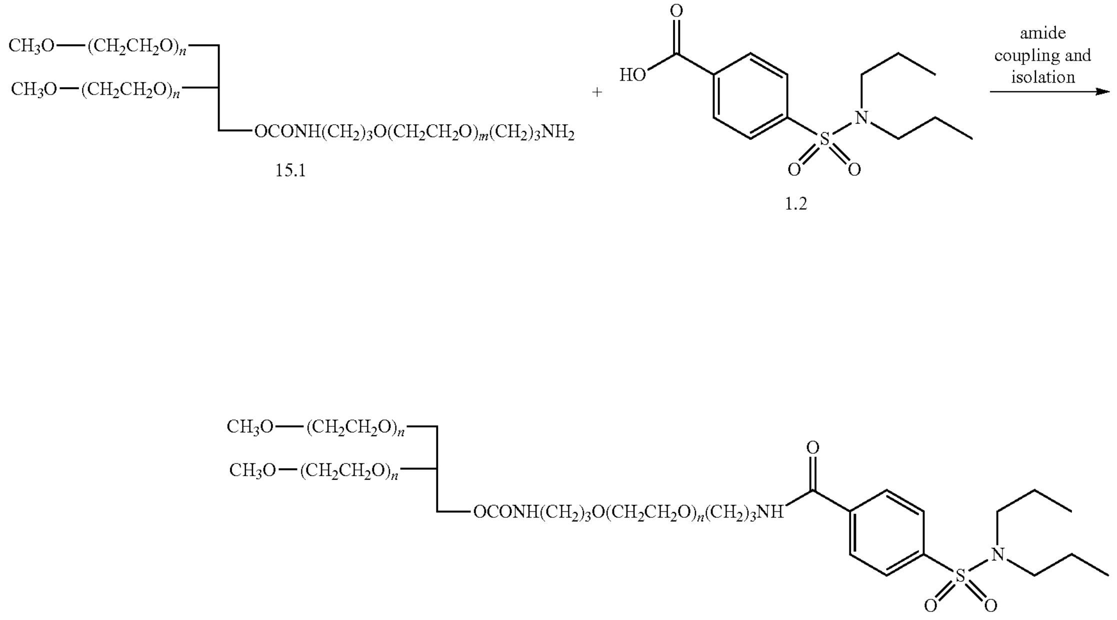
15.1
1.2
15.2
3-arm branched PEG, ——$(CH_2)_3$——NH2
Molecular Weight: 50,000
Chemical Name: 2,3-Bis(methylpolyoxyethylene-oxy)-1[(3-aminopropyl)polyoxyethylene-oxopropylaminocarbonyl-oxy]-propane
NOF catalog #: SUNBRIGHT GL3-400PA100U Scheme 17.

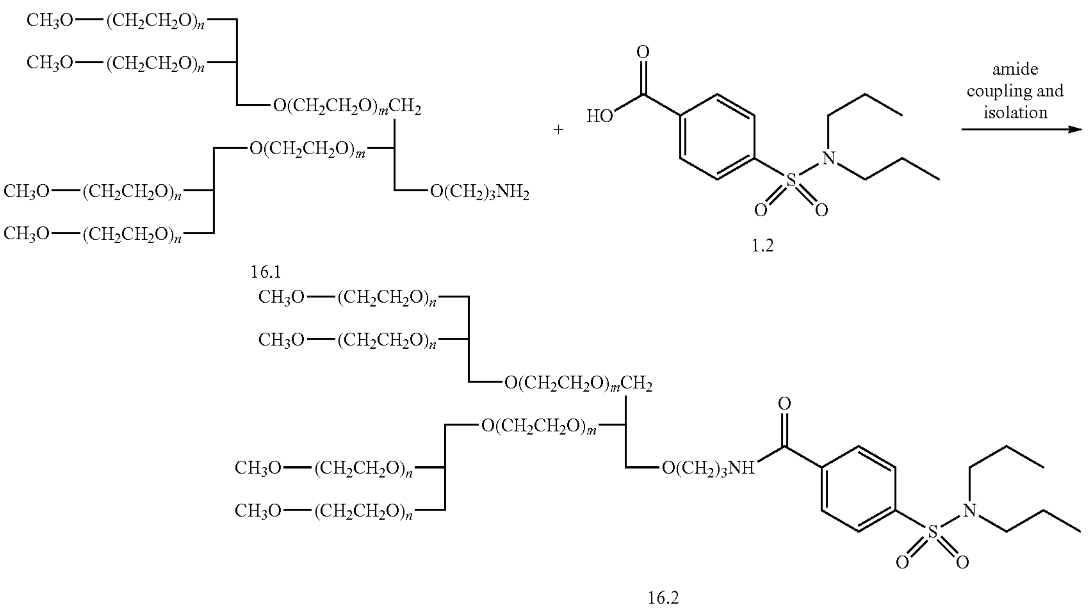

16.1 + 1.2 → 16.2

4-arm branched PEG, $—(CH_2)_3—NH_2$
Molecular Weight 40,000
Chemical Name: 2,3-Bis[2′,3′-di(methylpolyoxyethylene-oxy)-1′-propyl]polyoxyethylene-oxy-1-(aminopropyloxy) propane
NOF catalog #: SUNBRIGHT GL4-400PA Scheme 18.

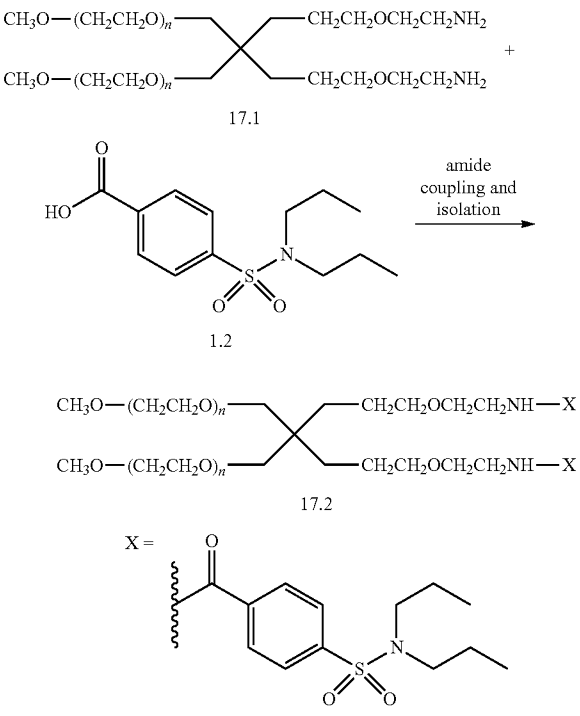

17.1 + 1.2 → 17.2

X =

2-arm PEG, $—((CH_2)_3—NH_2)_2$
Molecular Weight: 40,000
Chemical Name: 1,3-bis(2-aminoethoxy) 2,2-bis(methyl-polyoxyethylene-oxymethyl)propane(aminopropyloxy) propane
NOF catalog #: SUNBRIGHT PTE2-400EA Scheme 19.

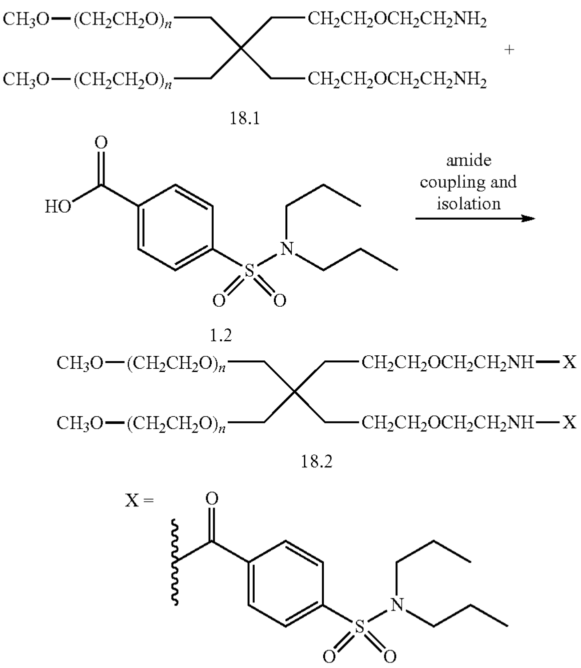

18.1 + 1.2 → 18.2

X =

2-arm PEG, $—((CH_2)_2—NH_2)_2$
Molecular Weight: 20,000
Chemical Name: 1,3-bis(2-aminoethoxy) 2,2-bis(methyl-polyoxyethylene-oxymethyl)propane(aminopropyloxy) propane
NOF catalog #: SUNBRIGHT PTE2-200EA General procedure for preparing PEG amine conjugates 5.2, 6.2, 9.2, 10.2, 12.2, 13.2, 14.2, 15.2, 16.2, 17.2, and 18.2. A 25 mL round-bottom flask fitted with a stir bar is charged with an aqueous solution of 0.1 M 2-(N-morpholino)ethanesulfonic acid (MES buffer, pH 6.0) (10 mL) and amine polymer amine (500 mg). Probenecid 1.2 (3 molar equivalents) is added and the reaction mixture is stirred vigorously until a clear solution is obtained. 1-Ethyl-3-(3-dimethylaminopropyl)carbodiimide (3 molar equivalents) is added and the reaction mixture is stirred for 30 minutes. The reaction mixture is transferred to a dialysis bag and is dialyzed against water for 24 hours (2 exchanges of water, 1 L each). The contents of the dialysis bag are transferred to a glass vial and the solution lyophilized to obtain polymer conjugate. The compound is characterized by NMR and mass spectrometry analysis.

General procedure for preparing PEG aldehyde conjugates 7.2, 8.2, and 11.2. A reaction vessel is charged with polymer aldehyde (500 mg) and an aqueous solution of sodium borate (5 mL of a 400 mM solution, pH 8.5). Probenecid aminohexylamide 2.3 (5 molar equivalents previously dissolved in 2 mL of methanol) is added followed by the addition of a freshly prepared aqueous solution of sodium cyanoborohydride (10 molar equivalents of a 3 molar aqueous solution). The reaction mixture is stirred for 4 hours at 25° C. The reaction mixture is transferred to a dialysis bag and is dialyzed against water for 24 hours (2 exchanges of water, 1 L each). The contents of the dialysis bag are transferred to a glass vial and the solution is lyophilized to obtain the polymer conjugate. The compound is characterized by NMR and mass spectrometry analysis.

Example 3: Probenecid Conjugates Reduce Neutrophil Infiltration into the Colonic Lumen Having shown that the MRP/$HXA_3$ pathway is conserved during infection with multiple pathogens in both lung and intestinal epithelia (Boll, E. J. et al., *Cell. Microbiol.* 14:120-32 (2012); Mumy, K. L. et al., *Infect. Immun.* 76:3614-27 (2008); Hurley, B. P. et al, *J. Immunol.* 173:5712-5720 (2004)), whether it also drives inflammation in the absence of infection was analyzed.

Figure 1B:
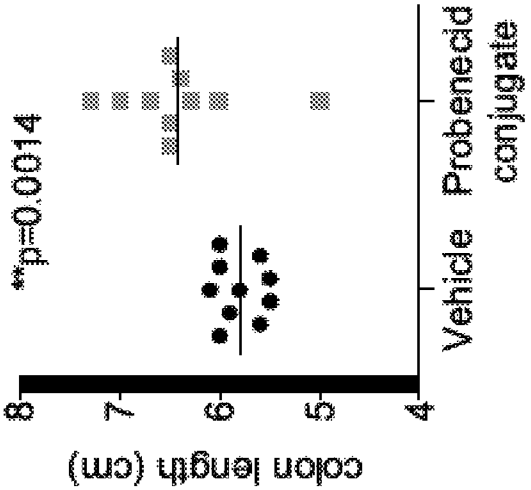
Figure 1C:
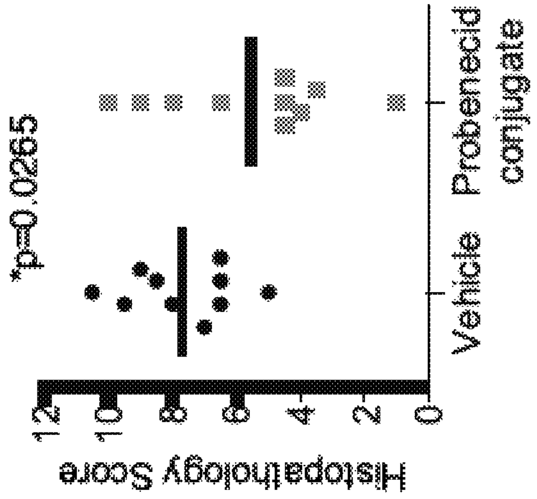
Figure 1D:
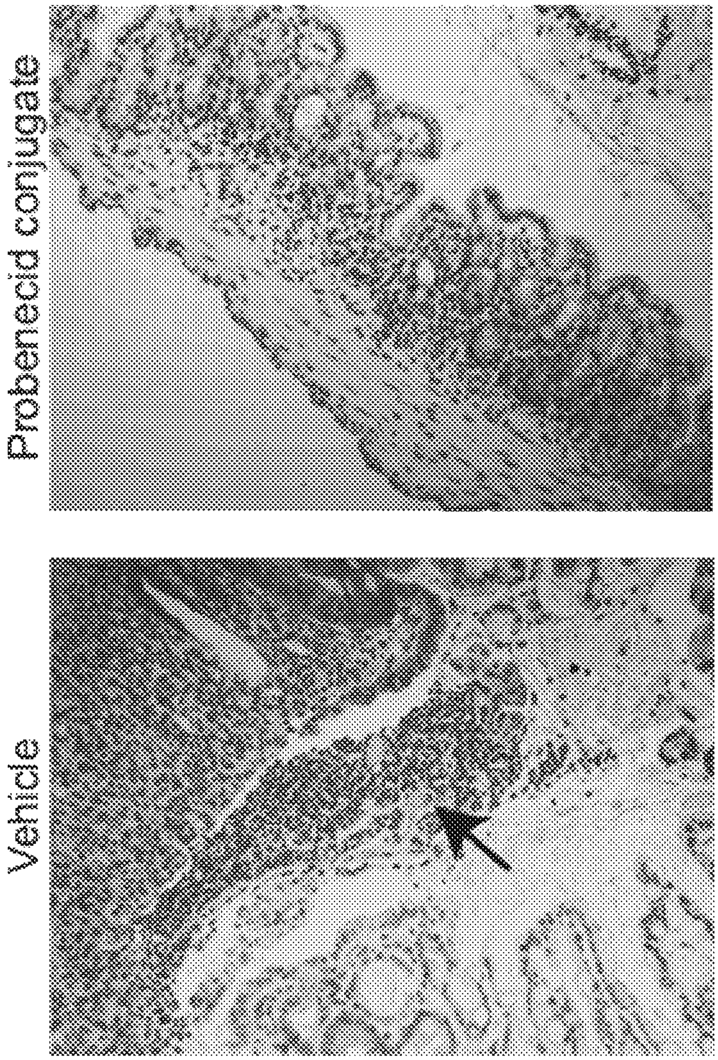
Figure 1E:
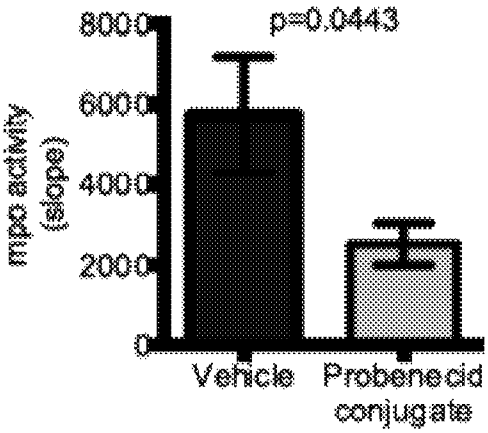
Figure 1F:
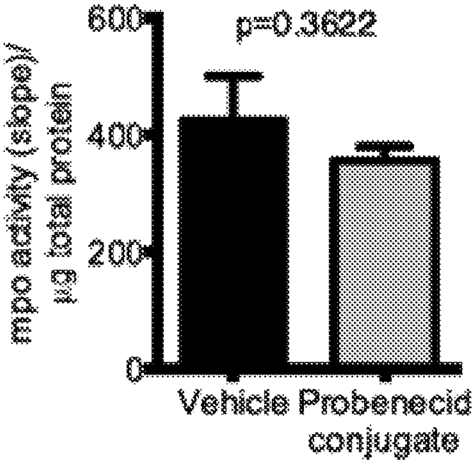
Figure 1G:
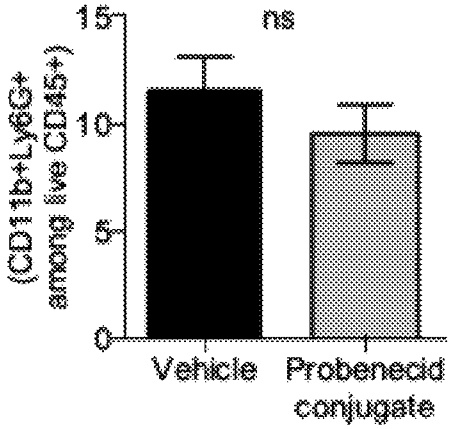
Figure 1H:
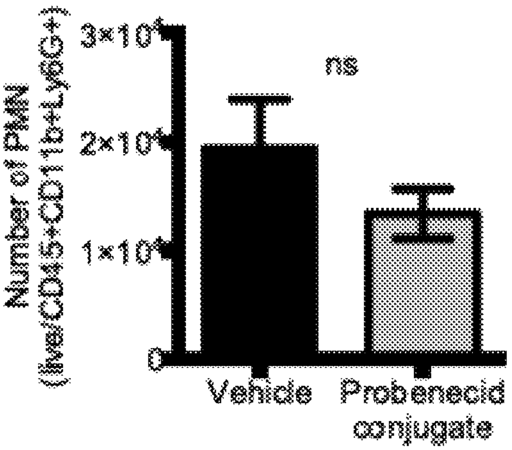
Figure 5:
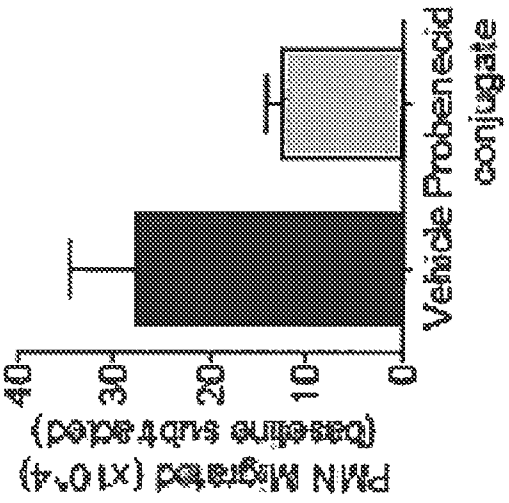
FIG. 5. Probenecid conjugate effectively inhibits $HXA_3$-induced neutrophil migration. HCT-8 epithelial monolayers were grown on inverted transwell inserts, and pretreated for 1 hour with 100 μM probenecid conjugate. Monolayers were then infected apically with *S. typhimurium* strain SL1344 for 1 hr, then washed and inverted. Neutrophils were added to the top of the well (basolateral side) and allowed to migrate for two hours, followed by quantitation of mpo as described. Data shown are mean+/−S.D. of a representative experiment.

Treatment of mice with dextran sodium sulfate (DSS) induces acute colonic inflammation characterized by epithelial damage and neutrophil influx (Okayasu, I. et al., *Gastroenterology* 98:694-702 (1990)). Semi-quantitative LC/MS/MS analysis of colonic mucosal scrapings revealed that DSS treatment strongly induced secretion of $HXA_3$ at the epithelial surface (FIG. 1A). To confirm that this increased $HXA_3$ contributes to disease, $HXA_3$ secretion was blocked via probenecid inhibition of MRP2 (Pazos, M. et al., *J. Immunol.* 181:8044-52 (2008)). Probenecid was chemically conjugated to periodate-oxidized 40 kDa dextran through a reductive amidation reaction. Because of the size of the attached dextran, intrarectal delivery of this compound to the intestine is predicted to target lumenal MRP2 and not reach systemic circulation. This conjugate was functional in vitro in a *Salmonella* infection assay (FIG. 5). In vivo inhibition of the MRP2/$HXA_3$ pathway by intrarectal administration of the probenecid-dextran conjugate significantly reduced intestinal pathology and colon shortening induced by DSS (FIGS. 1B-1D). Analysis of colon histopathology revealed that mice treated with the probenecid-dextran conjugate had reduced neutrophil infiltration into the colonic lumen (FIG. 1D), which was confirmed by a significant reduction in myeloperoxidase in fecal samples (FIG. 1E). Conversely, quantitation of neutrophils in the lamina propria revealed no significant difference with probenecid treatment (FIGS. 1F-1I), indicating that treatment primarily blocked migration across the epithelium into the lumen. These findings are consistent with other studies of the MRP2/$HXA_3$ pathway and suggest that neutrophil transepithelial migration may play a role in exacerbating inflammatory pathology.

Accordingly, these results show that the probenecid conjugates of the present technology are useful in methods of reducing neutrophil infiltration in a tissue and treating inflammatory conditions such as colonic inflammation.

Example 4: P-Glycoprotein Secretes AMEND

Figure 6:
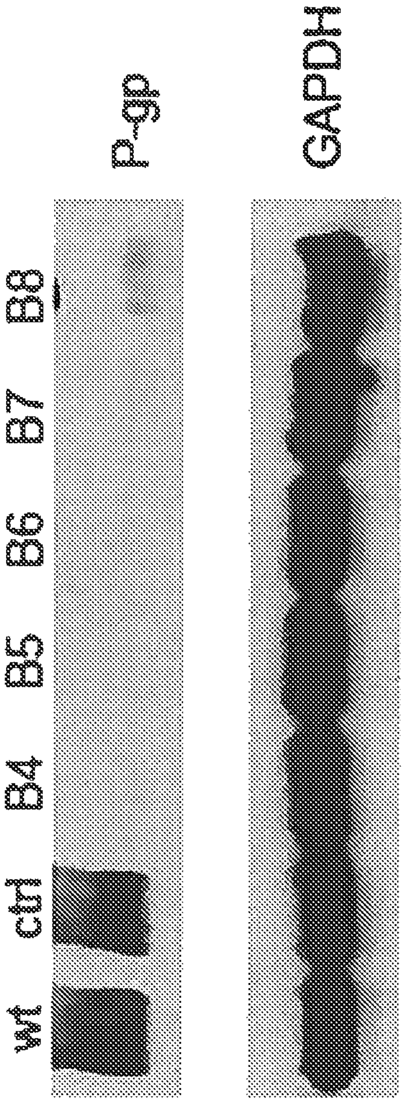
FIG. 6. shRNA knockdown of P-glycoprotein in T84 cells. T84 cells were infected with lentiviral particles carrying shRNA constructs targeting mdr1a. Cell lines B4-B8 contain independent targeting constructs and are compared to non-transfected cells (lane 1) and cells transfected with control shRNA (lane 2). Lysates were separated by gel electrophoresis, transferred to nitrocellulose and probed for (a) P-gp or (b) GAPDH loading control. As all constructs induced significant knockdown of P-gp expression by Western blot, clones B4 and B5 were chosen for further analysis.
Figure 7:
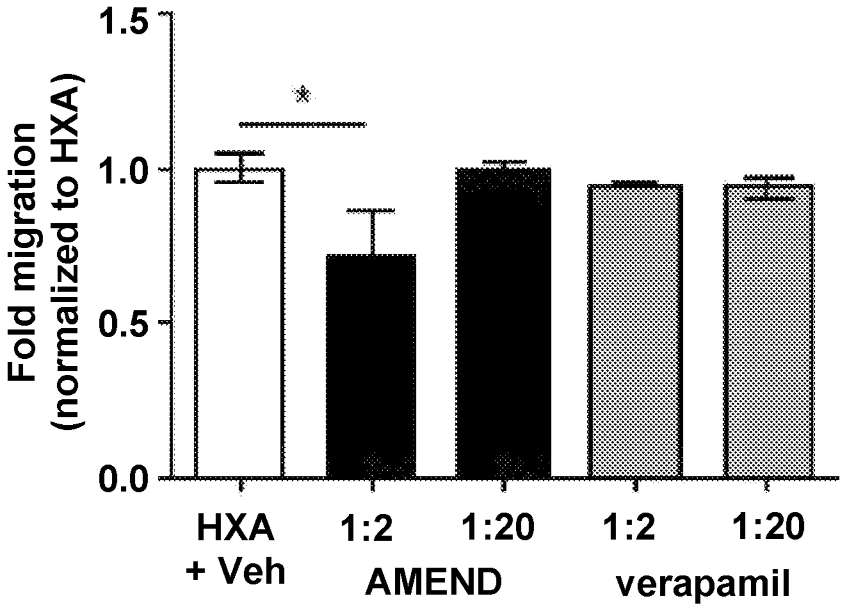
FIG. 7. AMEND secretion is P-gp dependent. T84 epithelial cells were treated with vehicle or with 40 μM verapamil hydrochloride, a P-gp inhibitor. Enriched supernatant fractions were prepared and evaluated for AMEND inhibitory activity in the cell-free migration assay. Pretreatment with verapamil inhibited secretion of the AMEND inhibitory compounds. Data shown are mean+/−SD of a representative of two independent experiments. *=p<0.05 by one-way ANOVA.

Supernatants from resting T84 colonic epithelial cells were collected and ultra-filtered to collect compounds smaller than 1 kDa, followed by enrichment for lipids by reversed-phase liquid chromatography. These lipid-enriched supernatants were capable of inhibiting primary human neutrophil migration stimulated by $HXA_3$ in a cell-free in vitro assay (FIG. 2A). The unknown compound(s) exhibiting this activity were termed "AMEND", for Activity Modulating Epithelial Neutrophil Discourse. To confirm that AMEND is specifically secreted by P-glycoprotein (P-gp), stable knockdown T84 cell lines expressing shRNA targeting mdr1a were created and reduction of P-gp expression was confirmed by Western blot (FIG. 6). Enriched supernatants from P-gp deficient cells lacked AMEND activity and failed to inhibit neutrophil migration (FIG. 2B). Similar results were obtained following treatment of wild-type cells with verapamil (FIG. 7), an inhibitor of P-gp.

Example 5: AMEND Components Responsible for Inhibition of Neutrophil Migration To identify AMEND components responsible for inhibition of neutrophil migration, a target-oriented approach to probe for receptor(s) activation was undertaken. Enriched AMEND was screened for both agonist and antagonist activity against a GPCR panel in an assay for β-arrestin activity that is independent of G protein subtype. Consistent with its role as an inhibitor of migration, AMEND displayed primarily antagonist activity at GPCRs, including chemoattractant receptors (Table 1). However, the strongest signal observed was for agonist activity at CB2, the peripheral cannabinoid receptor, supporting the identification of AMEND as one or more endocannabinoids.

TABLE 1

Results of GPCR activity screen with enriched AMEND.

| | GPCR | Assay Mode | % Activity | Assay Mode | Agonist used | % Inhibition |
|---|---|---|---|---|---|---|
| 1 | CNR2 | Agonist | 18% | Antagonist | CP55940 | −15% |
| 2 | ADORA3 | Agonist | 10% | Antagonist | 2-Cl-IB-MECA | −8% |
| 3 | CXCR4 | Agonist | 16% | Antagonist | CXCL12 | −2% |
| 4 | P2RY1 | Agonist | 11% | Antagonist | 2-methylthio-ADP | −1% |

TABLE 1-continued

Results of GPCR activity screen with enriched AMEND.

| | GPCR | Assay Mode | % Activity | Assay Mode | Agonist used | % Inhibition |
|---|---|---|---|---|---|---|
| 5 | CXCR3 | Agonist | 6% | Antagonist | CXCL11 | −18% |
| 6 | MTNR1B | Agonist | 6% | Antagonist | 2-Iodomelatonin | −14% |
| 7 | GPR120 | Agonist | 9% | Antagonist | GW9508 | −13% |
| 8 | ADCYAP1R1 | Agonist | 4% | Antagonist | PACAP-27 | −17% |
| 9 | AGTRL1 | Agonist | 4% | Antagonist | Apelin-13 | −12% |
| 10 | AVPR2 | Agonist | 5% | Antagonist | Vasopressin | −10% |
| 11 | C5L2 | Agonist | 3% | Antagonist | Complement C5a | −17% |
| 12 | CHRM1 | Agonist | −1% | Antagonist | Acetylcholine | −16% |
| 13 | CRHR2 | Agonist | 3% | Antagonist | Sauvagine | −15% |
| 14 | DRD3 | Agonist | 0% | Antagonist | Dopamine | −15% |
| 15 | EDNRA | Agonist | 3% | Antagonist | Endothelin I | −10% |
| 16 | OXTR | Agonist | 3% | Antagonist | Oxytocin | −10% |
| 17 | PPYR1 | Agonist | 1% | Antagonist | Pancreatic Polypeptide | −11% |
| 18 | CALCR-RAMP3 | Agonist | 10% | Antagonist | Calcitonin | 31% |
| 19 | EDG8 | Agonist | 14% | Antagonist | S-1-P | 18% |
| 20 | CALCR-RAMP2 | Agonist | 6% | Antagonist | Calcitonin | 17% |
| 21 | MTNR1A | Agonist | 11% | Antagonist | 2-Iodomelatonin | 14% |
| 22 | CCKBR | Agonist | 0% | Antagonist | CCK-8 | 22% |
| 23 | CXCR5 | Agonist | 4% | Antagonist | CXCL13 | 19% |
| 24 | PTGER2 | Agonist | 2% | Antagonist | Prostaglandin E2 | 19% |
| 25 | HTR1B | Agonist | −1% | Antagonist | Serotonin/5-HT | 17% |
| 26 | OPRD1 | Agonist | −1% | Antagonist | DADLE | 15% |
| 27 | GPR92 | Agonist | 2% | Antagonist | Oleoyl LPA | 15% |
| 28 | HTR1A | Agonist | 4% | Antagonist | Serotonin/5-HT | 15% |
| 29 | PTGIR | Agonist | −1% | Antagonist | Beraprost | 14% |
| 30 | NPBWR1 | Agonist | 0% | Antagonist | Neuropeptide W23 | 14% |
| 31 | TBXA2R | Agonist | −2% | Antagonist | I-BOP | 14% |
| 32 | OPRL1 | Agonist | 2% | Antagonist | Orphanin FQ | 12% |
| 33 | HTR1E | Agonist | 1% | Antagonist | Serotonin/5-HT | 12% |
| 34 | DRD4 | Agonist | 1% | Antagonist | Dopamine | 12% |
| 35 | HTR1F | Agonist | 3% | Antagonist | Serotonin/5-HT | 12% |
| 36 | P2RY2 | Agonist | −2% | Antagonist | UTP | 12% |
| 37 | EDG7 | Agonist | 0% | Antagonist | Oleoyl LPA | 12% |
| 38 | PTGER3 | Agonist | 0% | Antagonist | Prostaglandin E2 | 12% |
| 39 | FPR1 | Agonist | 3% | Antagonist | WKYMVm-NH2 | 11% |
| 40 | CXCR6 | Agonist | 7% | Antagonist | CXCL16 | 11% |
| 41 | AVPR1B | Agonist | 2% | Antagonist | Vasopressin | 11% |
| 42 | GPR119 | Agonist | 6% | Antagonist | Oleoyl Ethanolamide | 10% |
| 43 | CRTH2 | Agonist | 2% | Antagonist | PGD2 | 10% |
| 44 | NPY1R | Agonist | 1% | Antagonist | Peptide YY | 10% |
| 45 | HRH3 | Agonist | 2% | Antagonist | R-a methylhistamine | 10% |
| 46 | UTR2 | Agonist | 0% | Antagonist | Urotensin II | 10% |

With respect to Table 1, large scale preparations of AMEND from T84 cells were prepared and screened in the DiscoveRx GPCR Beta-arrestin activation assay in both agonist and antagonist mode. Percent activity (% Activity) is shown for both modes; for antagonist activity, percent inhibition of GPCR activation by the listed agonist is shown. Rows 1-2 and rows 3-4 show GPCRs for which AMEND displayed agonist activity above an arbitrary threshold of 10%. GPCRs in rows 5-7 and rows 8-17 had negative inhibition percentages but no corresponding activity in the agonist assay. Rows 18-21 contain GPCRs against which AMEND displayed both agonist and antagonist activity, which may reflect independent components of this mixture. Rows 22-46 contain GPCRs against which AMEND displayed antagonist activity above the arbitrary cutoff of 10%.

Figure 8:
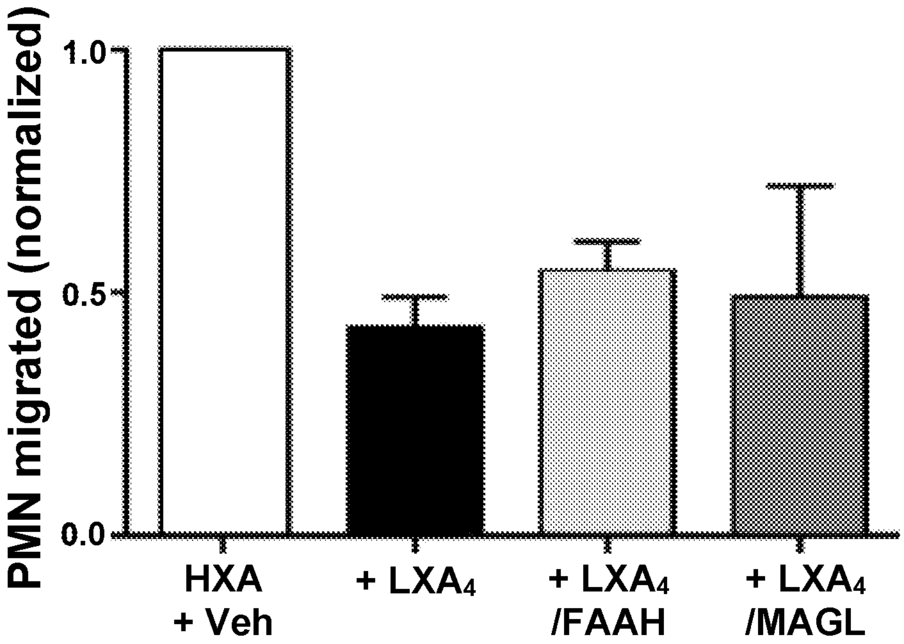
FIG. 8. FAAH and MAGL assays are endocannabinoid specific and do not affect the inhibitory activity of Lipoxin A4. Experiments were performed and normalized as in FIG. 2C. Lipoxin was used at 10 nM. Data are mean+/−S.E.M. combined from two independent experiments.

To confirm that AMEND activity is provided by endocannabinoids, its sensitivity to these enzymes was examined. Treatment of enriched AMEND with FAAH completely eliminated the inhibitory activity of AMEND, whereas treatment with MAGL failed to reduce the ability of AMEND to inhibit $HXA_3$-induced migration (FIG. 2C), suggesting that AMEND belongs to the NAE class. To confirm the specificity of enzyme treatment, a similar experiment was performed with the migration-inhibiting non-endocannabinoid lipid Lipoxin A4, which was not sensitive to deactivation by FAAH or MAGL (FIG. 8).

Example 6: Characterization of AMEND

The identification of AMEND was further narrowed down by mass spectrometry. Enriched AMEND preparation prepared from epithelial cells treated with or without verapamil were subjected to reversed-phase HPLC, revealing a specific peak in the absence of verapamil that contained potential AMEND compounds (FIG. 2D). Enriched AMEND preparations from control and P-gp deficient mice were subjected to electrospray mass spectrometry run in the positive ion mode (LC/MS), and it was found that levels of several endocannabinoids of both NAE and MAG classes were decreased in the absence of P-gp (Table 2). Qualitative analysis of relative abundance revealed a striking difference in peak profiles for $H^+$ and $Na^+$ adduct masses consistent with anandamide (AEA) (FIG. 2E). In order to determine which of these P-gp transported ECs exhibited actual AMEND inhibitory activity, purified compounds were tested in the cell-free migration assay. Only AEA, oleoyl ethanolamide (OEA), and alpha-linolenoyl ethanolamide (α-LEA)

exhibited significant inhibitory activity, identifying these NAEs as putative AMEND components (FIG. 2F).

TABLE 2

Endocannabinoids are secreted from epithelial cells via P-gp.

| | | Average* | Std Error | % of Control |
|---|---|---|---|---|
| Anandamide | control | 3.34 | 0.56 | |
| (AEA) | B4-mdr1a | 1.96 | 0.06 | 59 |
| | B5-mdr1a | 2.04 | 0.13 | 61 |
| Palmitoyl | control | 27.20 | 5.14 | |
| ethanolamide | B4-mdr1a | 10.87 | 1.50 | 40 |
| (PEA) | B5-mdr1a | 2.20 | 0.26 | 8 |
| Oleoyl | control | 5.97 | 0.98 | |
| ethanolamide | B4-mdr1a | 2.53 | 0.12 | 42 |
| (OEA) | B5-mdr1a | 2.57 | 0.21 | 43 |
| 2-Arachidonoyl | control | 35.53 | 6.35 | |
| Glycerol | B4-mdr1a | 32.17 | 1.37 | 91 |
| (2-AG) | B5-mdr1a | 29.47 | 1.19 | 83 |
| Noladin ether | control | 33.43 | 13.32 | |
| | B4-mdr1a | 154.03 | 3.47 | 461 |
| | B5-mdr1a | 56.23 | 1.32 | 168 |
| N-Arachidonoyl | control | 0.00 | 0.00 | |
| Dopamine | B4-mdr1a | 1.97 | 0.06 | N/A |
| | B5-mdr1a | 1.90 | 0.00 | N/A |

*(normalized to anandamide-d8 standard, which was at 1 μg/μL)

With respect to Table 2, semi-quantitative MS analysis was performed to compare enriched AMEND preparations from control T84 cells to those with shRNA-mediated P-gp knockdown (B4-mdr1a and B5-mdr1a). Relative abundance of each compound was calculated by comparison with measured intensity of anandamide-d8 standard; while this is only accurately quantitative for anandamide itself, it allowed for comparison of relative units between samples for the remaining compounds.

Example 7: Endocannabinoid Pathway

Figure 3A:
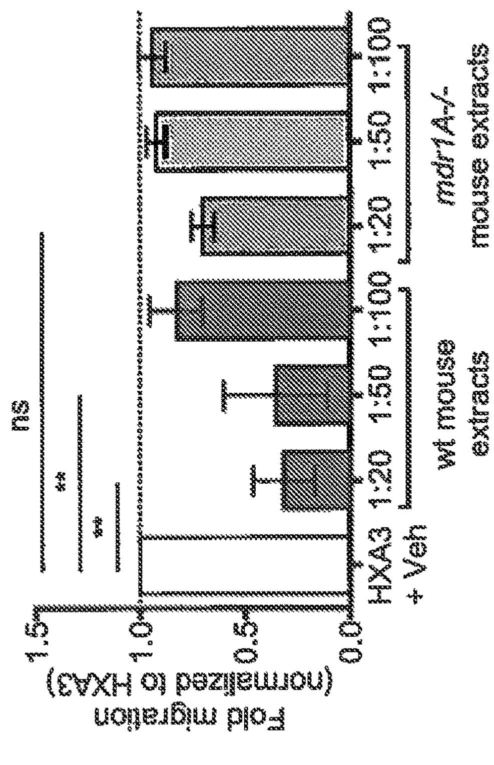
In FIG. 3B, indicated sample was pre-treated with FAAH for 30 min. at 37° C.
Figure 3B:
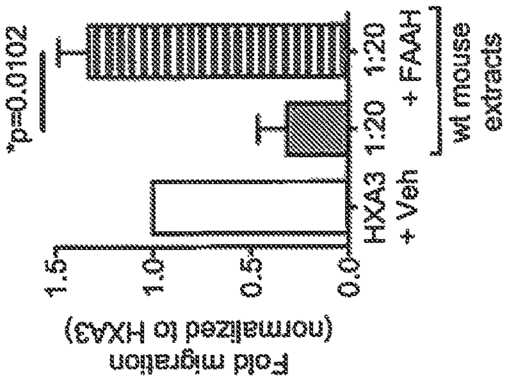

The mechanism of endocannabinoid transport into and out of cells is poorly understood, although it was thought that a membrane protein could transport anandamide and 2-AG across the epithelium. Having now established the identity of this transporter as P-gp, whether this pathway is active in the intestine was examined. Mucosal scrapings from the colon of WT and P-gp deficient (mdr1a−/−) mice were enriched for AMEND and evaluated for their ability to inhibit neutrophil migration. These ex vivo scrapings from WT mice inhibited migration similarly to in vitro AMEND, whereas scrapings from mdr1a−/− mice lacked inhibitory activity (FIG. 3A). When scrapings from WT mice were pre-treated with FAAH, they lost their inhibitory activity, confirming that these samples contained N-acyl ethanolamine endocannabinoids (NAE ECs) (FIG. 3B).

Figures 4A, 4B, 4C, 4D, 4E, 4F, 4G, 4H:
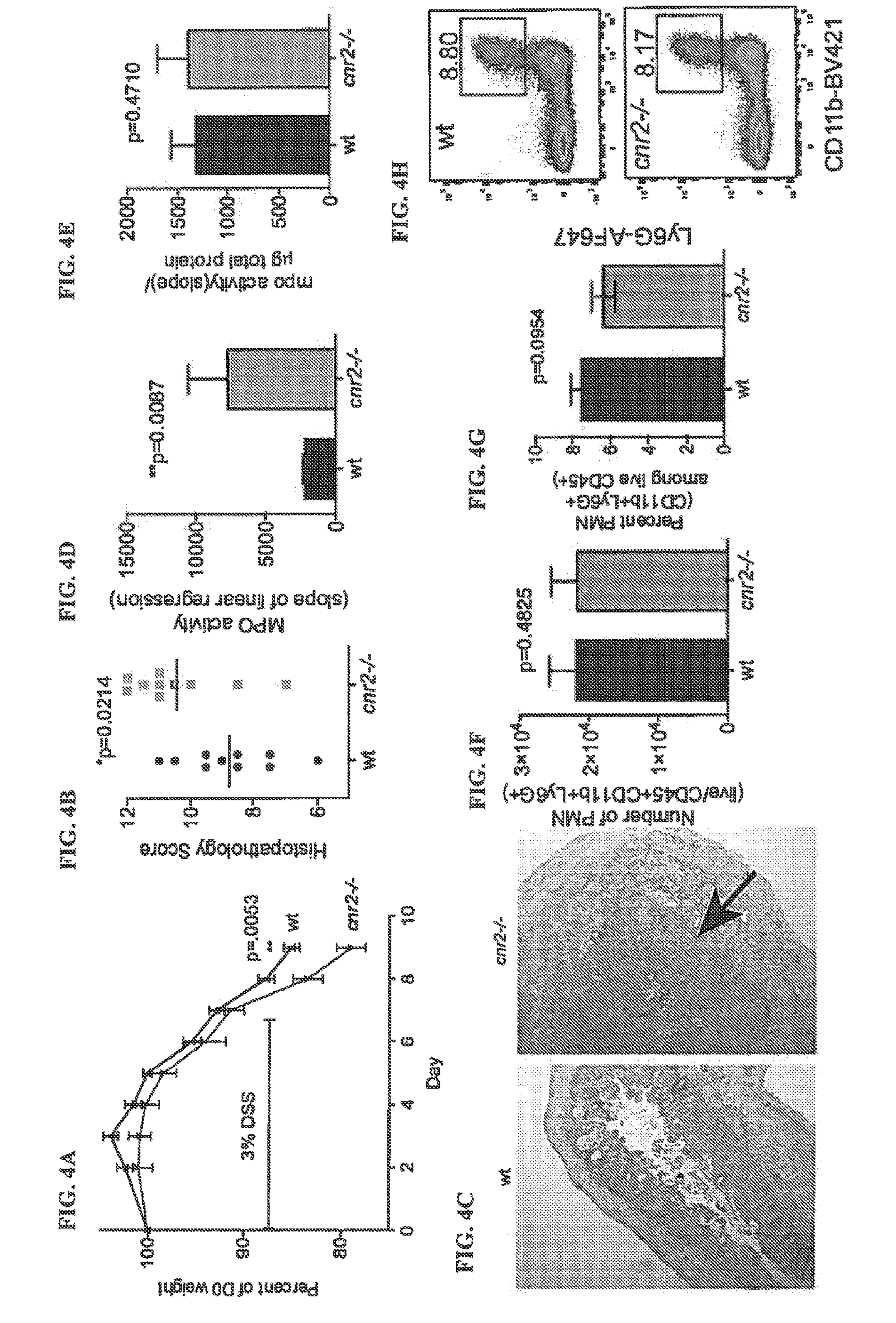
FIGS. 4A-4H. CB2-deficient mice are vulnerable to severe intestinal inflammation with increased neutrophil transmigration. Wt or cnr2−/− mice were treated with 3% DSS for 7 days and sacrificed at day 9. For all experiments, data are mean+/S.E.M, statistical analysis was performed with Mann-Whitney one-tailed nonparametric U test. Methods for histopathology scoring, myeloperoxidase activity measurement and flow cytometry analyses are the same as in FIGS. 1E-1I. Weights are shown as percentage of day 0 weight, n=15 wt and 14 cnr2−/− mice, p value refers to day 9 weight (FIG. 4A).
Figure 9:
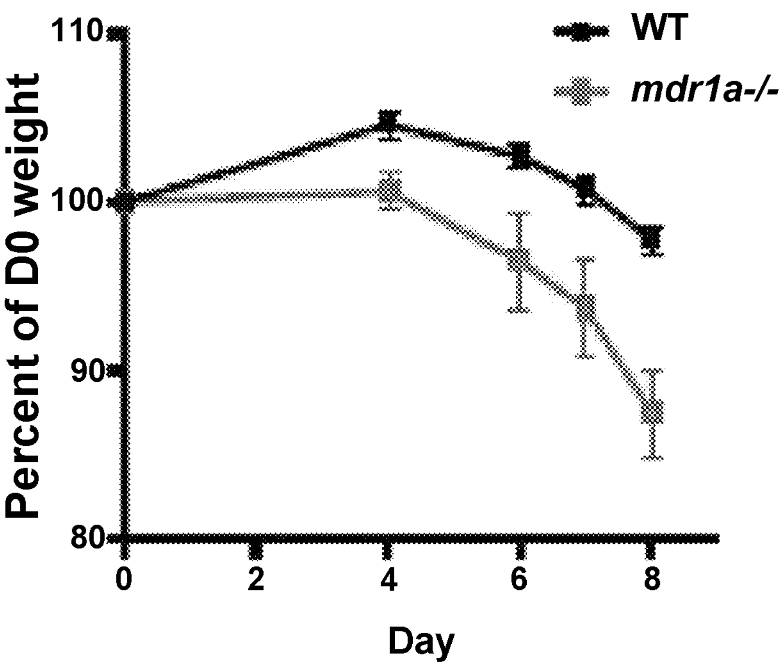
FIG. 9. DSS colitis in P-gp deficient mice. FVB wild-type and mdr1a−/− mice were treated with DSS as in FIG. 1. n=5 mice per group.

Having demonstrated that secretion of ECs by P-gp occurs in vivo, whether it regulates $HXA_3$ function in the intestine was investigated. In keeping with previous reports, mdr1a−/− mice that lack P-gp dependent EC secretion, in addition to developing spontaneous colitis, are more susceptible to DSS colitis (FIG. 9). CB2-deficient mice (cnr2−/−) that are unable to respond to AMEND similarly demonstrated increased susceptibility to DSS-induced colitis (FIGS. 4A-4C). In particular, they displayed dramatic increases in neutrophil migration into the intestinal lumen (FIGS. 4C, 4D), while neutrophil accumulation in the tissue was largely unaffected (FIGS. 4E-4H). These parallel experiments establish that in the absence of a functional P-gp/AMEND pathway, intestinal homeostasis is disturbed and mice are more vulnerable to rapid onset of inflammatory disease. As when normal neutrophil transmigration was blocked during DSS colitis with probenecid (FIG. 1), migration across the epithelium specifically caused significant tissue damage that contributed to disease pathology.

Figure 21A:
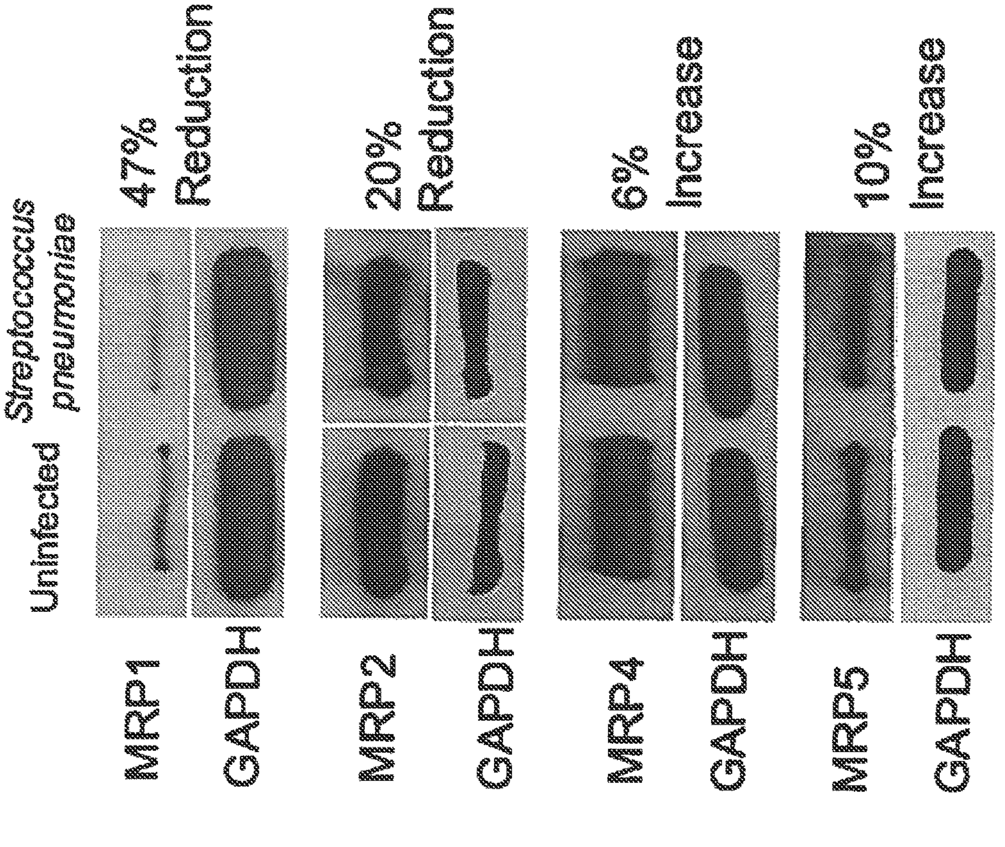
FIGS. 21A-B. MRP inquiry during infection. NIH-H292 cells were infected and then MRP profiles were generated by 3 different techniques: mRNA RT-PCR quantification, protein Western blots, and cell-surface biotinylation (in conjunction with Western blots). MRP1, 2, 3, 4, 5, and P-pg were investigated for possible changes upon infection with *Streptococcus pneumoniae*. RT-PCR revealed a slight reduction in MRP1 and slight increases in MRP2 and MRP5 during pneumococcal infection (FIG. 21B). Total cell lysate revealed the increases or reductions indicated to the right of the Western blot, as normalized to GAPDH and analyzed by ImageJ (FIG. 21A). P-gp and MRP3 were not detectable by any of these methods.
Figure 21B:
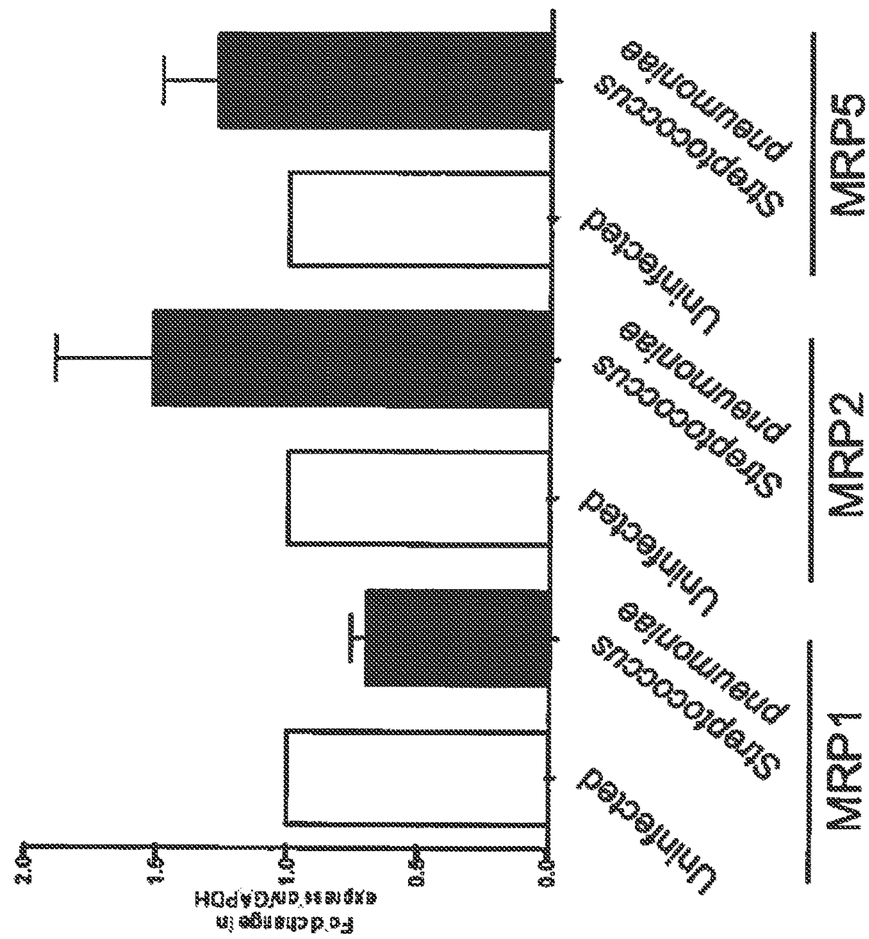

Example 8: Survey of MRP Expression Patterns During *S. pneumoniae* Infection To study inflammatory responses during infection with *S. pneumoniae* an in vitro model of PMN migration was established using polarized monolayers of the human mucoepidermoid pulmonary carcinoma cell line, NCI-H292 (herein identified as "H292"), a type II alveolar epithelial cell type. Given the increasing appreciation that efflux transporters play a role in host defense, this model was used to further examine the expression profiles of MRPs with the objective of analyzing genes that differ in mRNA or protein expression during *S. pneumoniae* infection. mRNA was extracted and the expression levels of MRPs 1, 2, 3, 5 and MDR1 (the gene that encodes for P-glycoprotein, P-gp) were quantified via RT-PCR and it was found that MRP1 was modestly reduced during infection with *S. pneumoniae* whereas expression of MRP2 and MRP5 both showed slight increases; however, none of these changes was statistically significant (FIG. 21B). Also, there was no detectable expression of MDR1 at baseline or during pneumococcal infection. Additionally, cell lysates analyzed via Western blots for protein expression showed a similar reduction in MRP1 during pneumococcal infection (FIG. 21A). MRP2 showed a slight decrease in total cellular content while MRP4 and MRP5 showed slight increases, though these changes are statistically insignificant. Like the RT-PCR data, MRP3 and P-gp were undetectable via Western blot as well. Accordingly, it is surmised that these proteins are not expressed by H292 cells or are not measurable under the conditions examined, which is consistent with previous studies measuring these transporters at basal state.

Example 9: MRP1 and MRP2 Show Diverse Patterns of Expression During *Streptococcus pneumonia* Infection Though there were a few significant changes observed in whole cell mRNA and protein, it is well documented that MRPs undergo post-translational modification that can affect overall cellular localization. The subcellular localization for efflux proteins is critical because the main activity of MRPs is to efflux a payload from the intracellular space to the extracellular milieu. Unless the protein has oriented itself to efflux its ligand to the extracellular space, the activity of such a pump could be useless. Therefore, whether pneumococcal infection could evoke MRP post-translational modifications or subcellular localization was examined. To examine this possibility, the apical surface of polarized cell monolayers was selectively biotinylated following infection with *S. pneumoniae* or uninfected treatment with Hanks Balanced Salt Solution. Since this method allows for the identification of changes in protein expression, specifically at the apical surface in response to pneumococcal infection, apically expressed MRPs were surveyed in the absence and presence of pneumococcal infection. The apical surface was selectively labeled as a means to focus on those transporters likely to efflux immunomodulatory agents into the infected luminal space.

Figure 16:
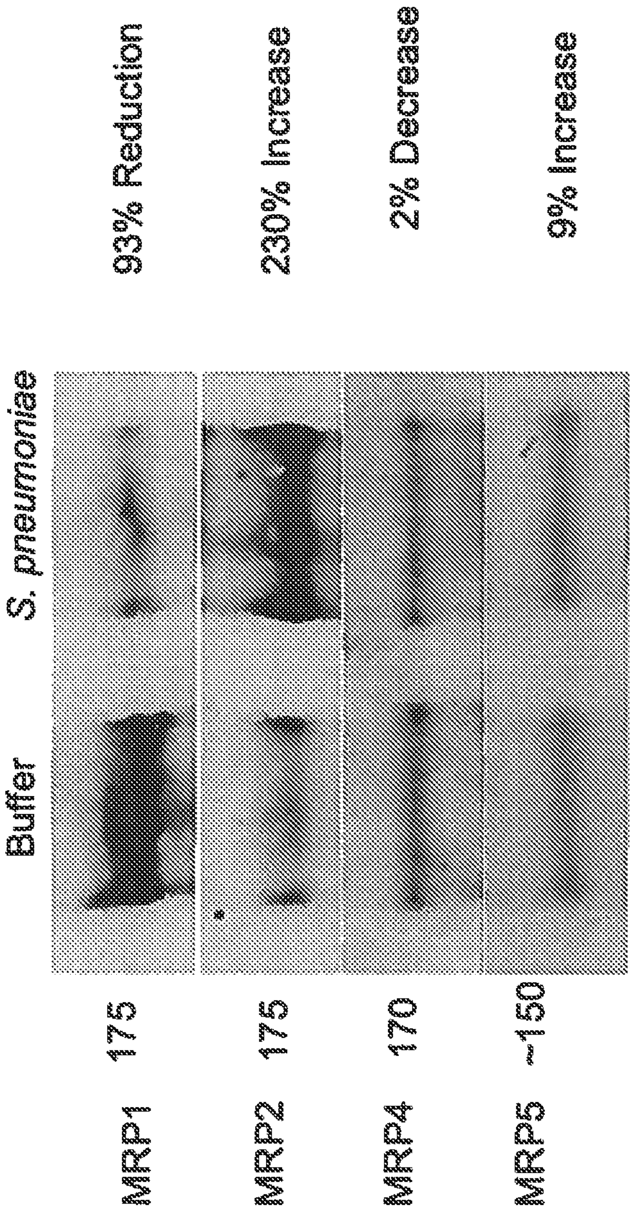
FIG. 16. MRP1 protein on the apical surface reduces during infection with *Streptococcus pneumoniae* while MRP2 increases. Western blot analysis of apical-surface biotinylation comparing uninfected and infected NIH-H292 cells. Cells were infected, washed, then allowed to rest at 37 degrees for 1 hour post-infection. Apical surfaces were then labeled with biotin and lysed. Samples were normalized to GAPDH expression, exposed to beads with antibodies cross-linked for the protein specified on the left-hand column, and probed using streptavidin-HRP. MRP4 and 5 showed little increase upon infection. MRP1 showed a 93% reduction while MRP2 showed a 230% increase when exposed to *Streptococcus pneumoniae.*
Figure 17A:
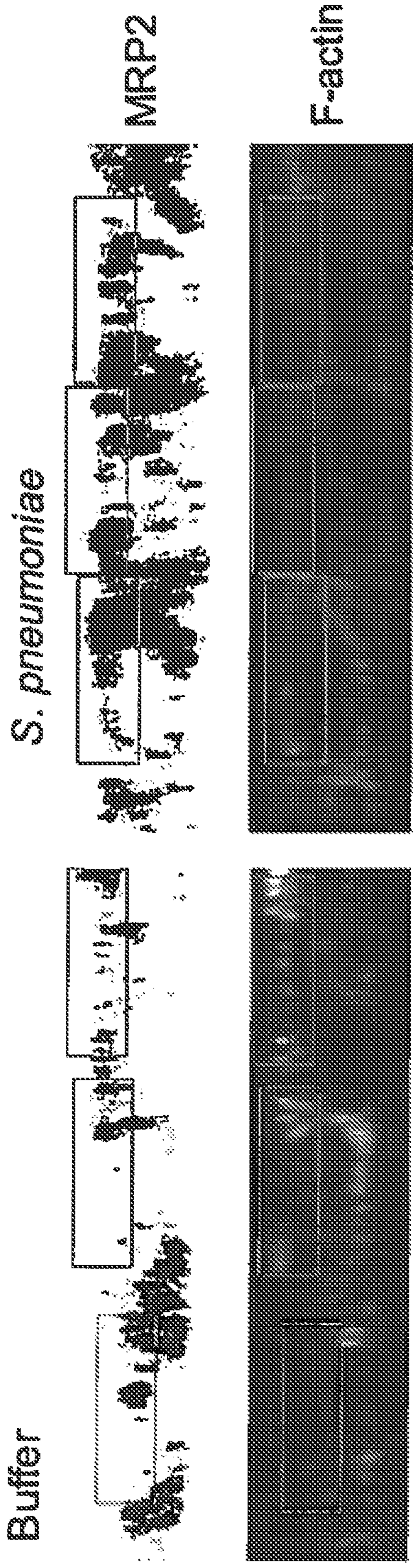
FIGS. 17A and 17B. Immunofluorescence of MRPs during infection. Polarized NIH-H292 were infected with 10 MOI of *Streptococcus pneumoniae*, fixed and then stained for MRP2. IF images were separated into individual channels and apical surface area occupied by MRP2 was measured.
Figure 17B:
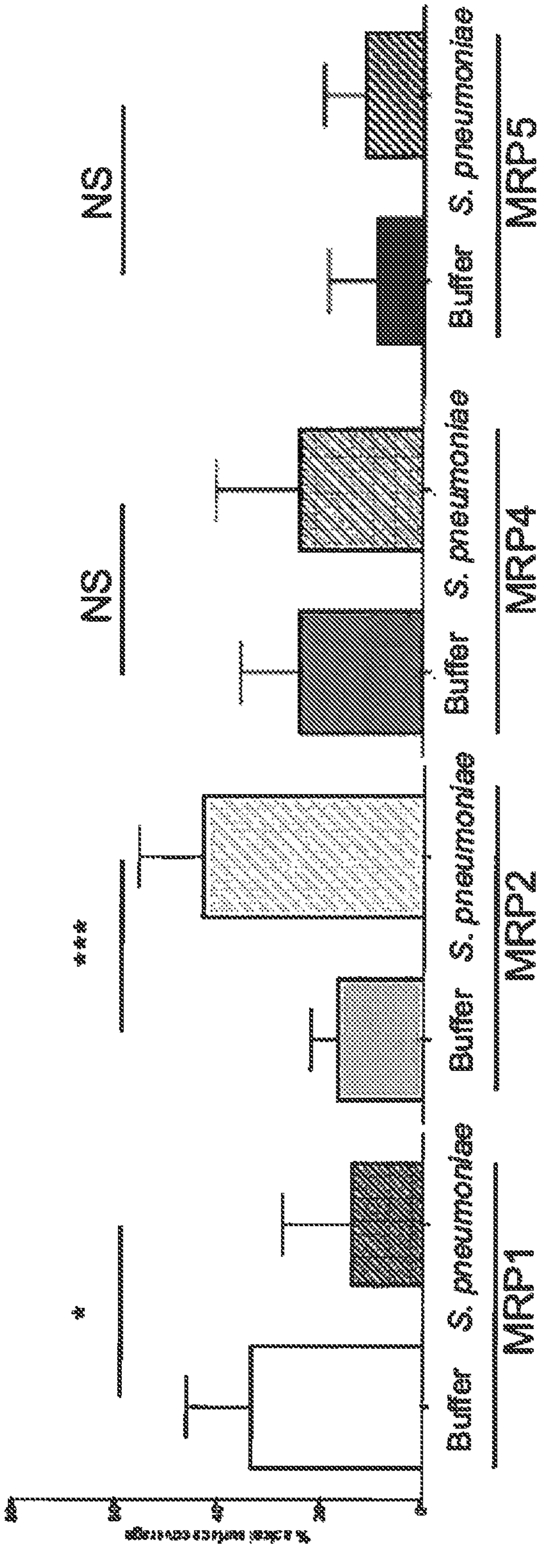

Given that during pneumococcal infection the expression of MRP1, -2, and -5 is modified (FIGS. 21A-B), these transporters were examined. As shown in FIG. 16, following pneumococcal infection, a significant decrease in apical surface MRP1 was detected whereas the apical surface expression of MRP2 was significantly increased. Such results are consistent with the mRNA expression data (and protein expression data with MRP1; FIGS. 21A-B). However, there were only nominal changes of surface-expressed MRP4 and MRP5, and these changes were insignificant compared to the changes observed for MRP1 and MRP2 (FIG. 16). It was further confirmed that pneumococcal infection results in a decrease in MRP1 expression and a reciprocal increase in MRP2 expression by immunocytochemistry (FIG. 17B). No change was observed in MRP4 surface expression and extremely low surface expression of MRP5 via immunofluorescence, which seems to confirm the finding that the majority of pulmonary MRP5 is held intracellularly. In light of the biotinylation and immunofluorescence data, efforts were focused on examination of MRPs 1 and 2 which are detectable, localize to the cellular surface, and modulate during infection with *Streptococcus pneumoniae*.

Figure 18:
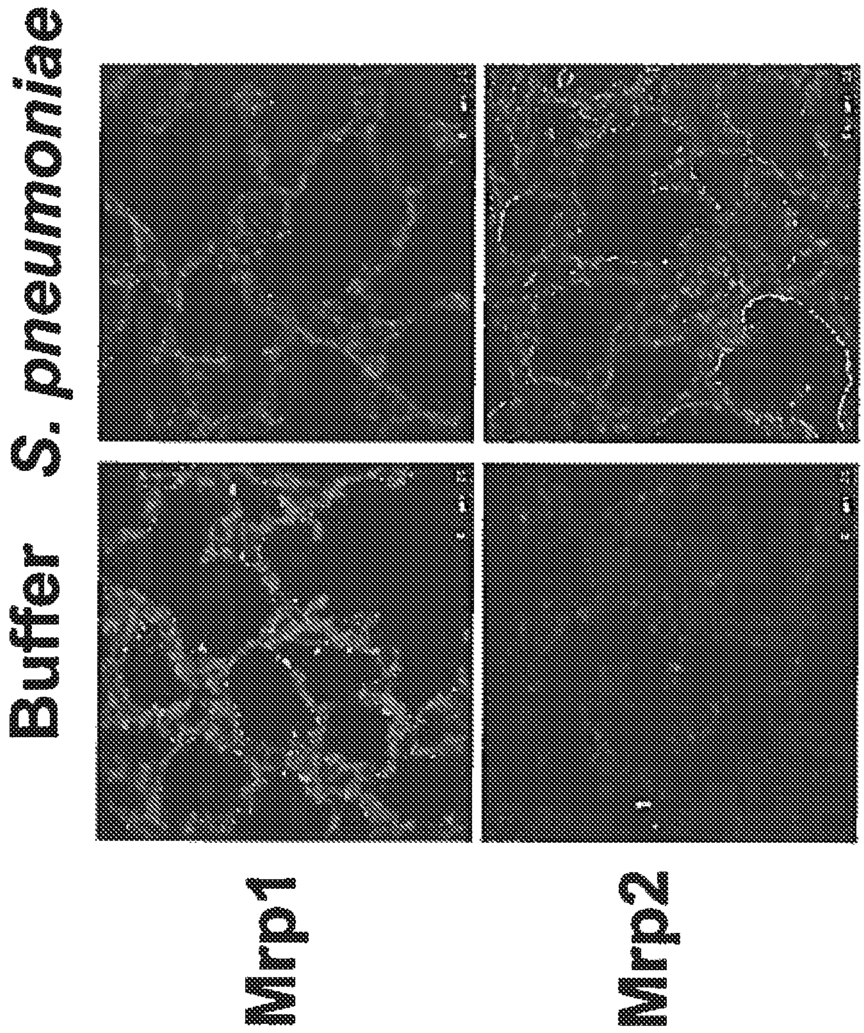
FIG. 18. Expression of MRP1 and MRP2 in mouse lungs. Mice were infected via an intratracheal route with *Streptococcus pneumoniae* and sacrificed 2 days post-infection. Lungs were excised, re-inflated, sectioned, and stained for Mrp1 and Mrp2. Mrp1 expression appears reduced in infected mouse lung as compared to PBS treated mice (Top). Mrp2 appears to have increased expression, especially around the periphery of cells (Bottom).

To examine whether such in vitro observations correlate to changes in in vivo MRP localization, C57BL/6 mice were infected with $2.5\times10^5$ CFU of *S. pneumoniae* or mock treated with PBS. On day two post-infection, after symptoms are first noted, the mice were sacrificed. Afterward, the lungs were excised and sectioned, and immunohistochemistry was performed for both MRP1 and MRP2. Similar to the in vitro findings, pneumococcal infection reduced MRP1 protein expression and reciprocally increased the expression of MRP2 (FIG. 18).

Example 10: Effects of MRP1 and MRP2 on Neutrophil Transmigration

On the balance of these observations, it is thought that since expression of MRP1 is high at a basal state but lower during infection, this transporter might play a role in establishing an immunosuppressive tone during homeostasis, whereas MRP2, which increases during infection, may function in a proinflammatory capacity. To test this hypothesis, the functional consequences of transporter dynamics in the context of infection were analyzed. Expression of the ABC efflux transporter, MRP2, is upregulated in states of epithelial inflammation and the 12/15-LOX pathway has been implicated as a requirement for maximal induction of this MRP2 upregulation. Previously, it was observed that PMN migration into the lung airways during pneumococcal infection required the production of the lipid chemoattractant hepoxilin A3, an eicosanoid derived from arachidonic acid via the action of 12-lipoxygenases (LOX) in lung epithelial cells. Since it has also been shown that MRP2 is an efflux transporter for $HXA_3$, the extent to which pharmacological inhibition of MRP2 also blocks PMN transepithelial migration during pneumococcal infection was analyzed.

*S. pneumoniae* can induce PMN transepithelial migration across model lung epithelia where a well-established in vitro model system is utilized. Briefly, H292 cells are seeded on permeable supports to form a barrier, thereby mimicking the in vivo architecture. Freshly isolated human neutrophils are then applied to the basolateral chamber of the transwell, allowing the neutrophils to transverse the epithelial layer in response to chemoattractants released by the epithelium. To examine how the MRPs may influence PMN transmigration H292 polarized monolayers were exposed to the MRP2 inhibitor probenecid (see Methods) prior to infection, and whether such treatment inhibits PMN migration was tested. As expected, the probenecid-treated samples had significantly fewer migrated neutrophils than mock-treated control samples, indicating some pro-migratory effects mediated through MRP2 activity in this well-established model of neutrophil transmigration.

*S. pneumoniae* infection under conditions where MRP2 function was impeded with probenecid was examined. C57BL/6 mice were infected with between $1\times10^5$ and $3\times10^5$ bacteria via the trachea, leading to lobar pneumonia and progressing to bacteremia and sepsis, after which the mice succumb to infection. Probenecid was delivered 3 hours prior to infection as a primer and again at 3-hours post-infection.

Figure 19A:
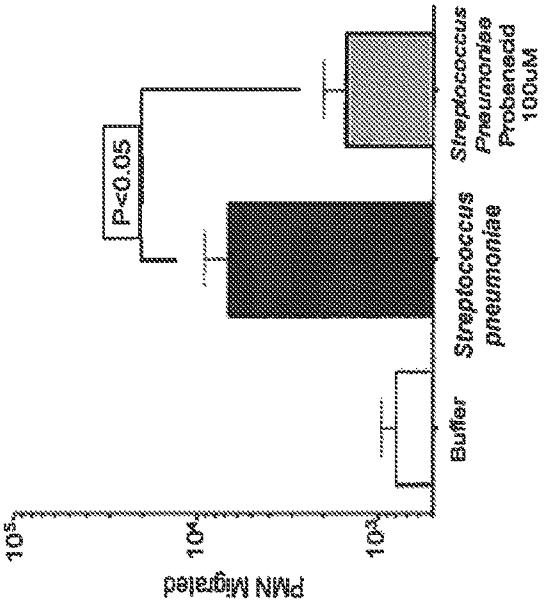
FIGS. 19A-19E. MRP2 inhibition in vivo. Using an in vitro model of neutrophil migration, we examined the results of MRP2 inhibition. MRP2 inhibition via Probenecid treatment results in a reduction of neutrophils migrating in a basolateral-to-apical direction (FIG. 19A). Following this in vitro result, C57/B16 mice were treated with either PBS or Probenecid and subsequently infected with *Streptococcus pneumoniae*. Mice treated with probenecid had fewer Cd11b-positive/Ly6g-positive cells (neutrophils) in the bronchoalveolar lavage (BAL) isolated from infected lungs (FIG. 19B). Probenecid also reduced the number of bacteremic mice and overall bacteremia (FIG. 19C). Statistics resulted from Mann-Whitney test of D1 bacteremia data (FIG. 19D) Cd11b+/Cd45+/Ly6g-granulocytes showed no differences, indicating the effects are likely neutrophil specific. When comparing mice that did not develop bacteremia, probenecid may have had a protective effect as these mice had an approximately 2-fold difference in the bacterial CFU, though these numbers failed to reach statistical significance (FIG. 19E). Mice that developed bacteremia did not appear to have differences in bacterial burden in the lung.
Figure 19B:
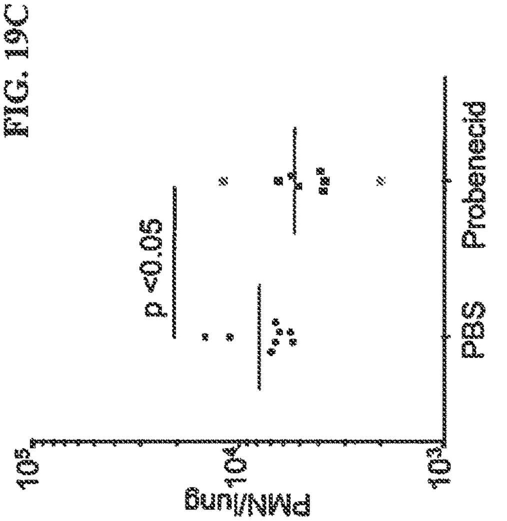
Figure 19C:
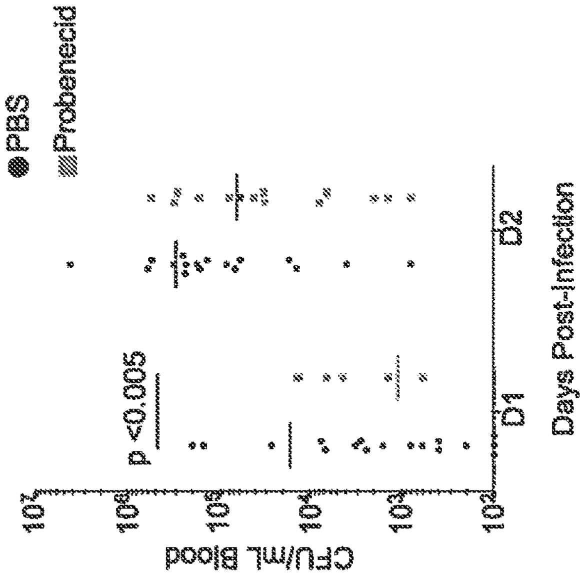
Figure 19E:
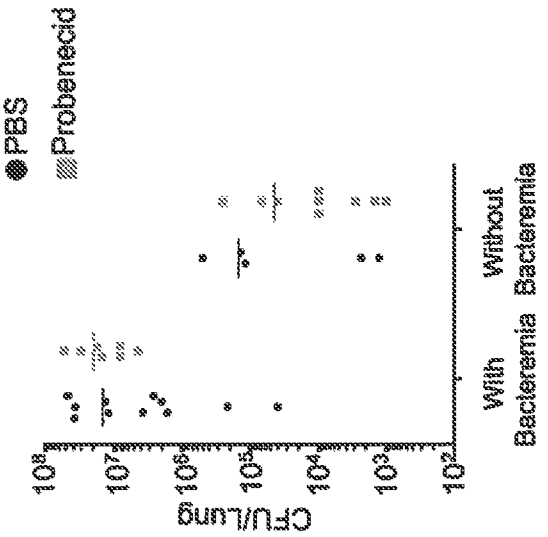
Figure 19D:
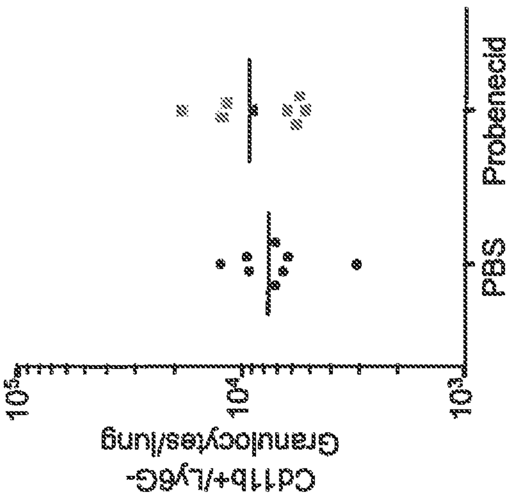

On Day 1 post-infection, the bronchoalveolar lavage fluid (BALF) from probenecid-treated mice exhibited 35% fewer neutrophils than PBS-treated mice (FIG. 19B). Probenecid-treatment lead to fewer cases of bacteremia on D1 and those that did develop bacteremia had approximately 10-fold lower CFU in the blood as compared to PBS-treated mice (FIG. 19C). Despite the reduction in PMNs in the BALF, no reduction in other granulocytes in the mouse lung (FIG. 19D) was observed, leading to the conclusion that the probenecid effect appears to be neutrophil-specific. 48 post-infection, this trend continues to produce a 10-fold reduction in bacteremia in the probenecid-treated mice (FIG. 19C), though these are no longer statistically significant values. The number of bacteria in the lung 48 hours post-infection was the same despite the reduction in the number of bacteria invading the circulation. Therefore, MRP2 inhibition is effective at limiting neutrophil infiltration to the lung 24 hours post-infection and this corresponds to a reduction bacteremia that continues 48 hours post-infection.

To more deeply elucidate how MRP1 or MRP2 activity could impact inflammation, a constitutively-expressed shRNA H292 cell-line was generated that knocked down either MRP1 or MRP2 expression (MRP knockdown). Consistent with the hypothesis that MRP1 is involved in an anti-inflammatory cascade, it was found that MRP1-deficient cells infected with *S. pneumoniae* induced significantly more PMN transepithelial migration, as compared to scrambled-control cells when infected with *S. pneumonia*. In addition, similar to the results with probenecid (FIG. 19A), MRP2 knockdown cells also failed to support PMN transepithelial migration compared to control cells. This suggests that epithelial-derived MRP1 activity represses PMN transepithelial migration while MRP2 expression and activity is necessary for neutrophil transmigration across the epithelium during pneumococcal infection.

Since these results imply that MRP1 effluxes substrates that are immunosuppressive while MRP2 secretes substrates that are pro-inflammatory, an attempt to recapitulate this outcome by isolating the bioactive lipids from the apical supernatants of infected polarized H292 cell monolayers (FIG. 20A) was performed. Previous research shows that MRP2 effluxes $HXA_3$ during bacterial infection in the intestine and PMN transepithelial migration is absolutely reliant on $HXA_3$ production. For these studies, lipid extracts from supernatants were collected and ultra-filtered using an Am icon apparatus (Millipore) fitted with 1,000-Da cutoff membrane. Removal of salt and enrichment of the lipids was achieved using a C18 Backerbond extraction column. Lipid extracts were isolated from either scrambled control or MRP2 knockdown cells, and applied to the apical chamber of naïve H292 cells. As shown in FIG. 20B, enriched lipids from MRP2 knockdown cells (MRP2 KD) showed reduced PMN migration as compared to scrambled control, implying MRP2 effluxes a pro-inflammatory stimulus, most likely $HXA_3$.

Using a similar strategy, Hank's buffer was applied to the apical surface of scrambled control cells or MRP1 knockdown cells to produce conditioned media. Proinflammatory lipids were then resuspended as depicted in FIG. 20C with unconditioned media, conditioned media from scrambled control that contains MRP1, or conditioned media from MRP1-deficient cells. Exposure of the lipid extract to unconditioned media promoted the maximal amount of PMN migration. However, the scrambled control cells conditioned with media from cells with intact MRP1 showed a marked reduction in PMN migration (contains immunosuppressive agent), whereas media conditioned with MRP1 knockdown cells (lacks immunosuppressive agent) failed to reduce PMN migration, and showed levels of PMN migration consistent with unconditioned supernatants. Thus, by stymying secretion of this inhibitor in MRP1 deficient cells, the restraint was removed and resulted in an increase neutrophil migration. We refer to this immunosuppressive agent as L-AMEND (Lung-Activity Modulating Epithelial-Neutrophil Discourse). Collectively, these results provide evidence for an MRP1/L-AMEND pathway that acts to suppress (counter-balance) the ability of MRP2/$HXA_3$ pathway to incite PMN transmigration triggered by *S. pneumoniae.*

Figure 20D:
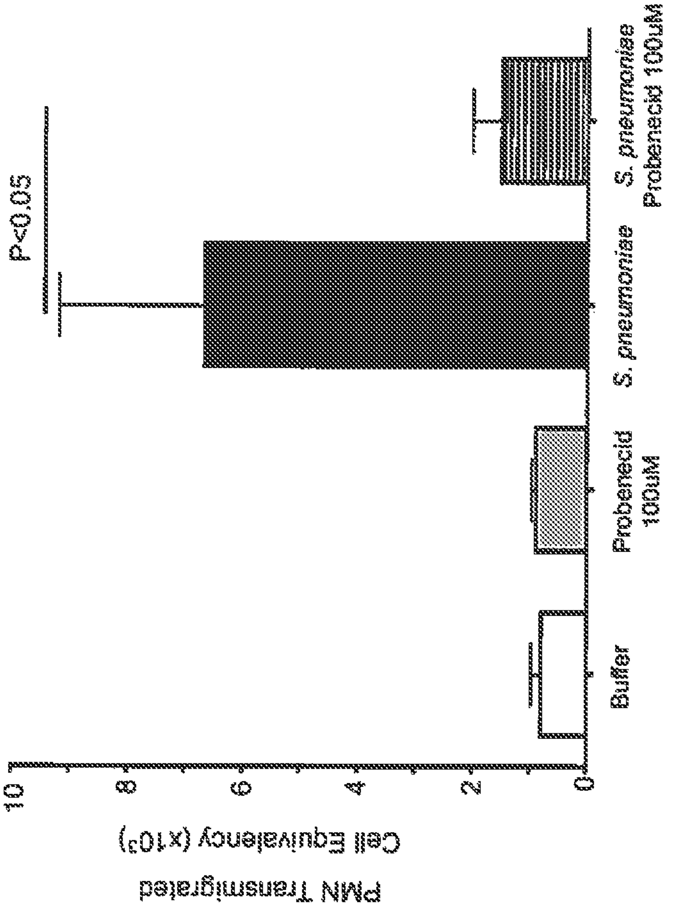

Using an in vitro model of neutrophil (PMN) migration, we examined the results of MRP2 inhibition. NIH-H292 cells were incubated with 100 μM of the MRP2 inhibitor Probenecid (horizontal striped) or mock treated with PBS (black) before infection. Both control and probenecid treated cells were then washed and infected with 10 MOI *Streptococcus pneumoniae*. Neutrophils were placed in the basolateral chamber of the membrane construct and allowed to migrate post-infection. Neutrophils that have traveled to the apical chamber were quantified with a modified myeloperoxidase assay against a standard number of neutrophils. Shown in FIG. 20D is a representative data set that has been repeated at least 3 times. Probenecid pretreatment effectively reduced the number of neutrophils traveling from the basolateral-to-apical chamber through the epithelial cell layer and growth membrane when comparing to mock-treated cells. Uninfected cells are represented in white, labeled "Buffer". Statics performed using unpaired T-test. These results show that MRP2 inhibition with probenecid reduces neutrophil migration.

Example 11: Inhibition of Neutrophil Migration by Compounds of the Present Technology This example will demonstrate the efficacy of compounds of the present technology in inhibiting neutrophil migration in vitro.

Peripheral blood neutrophils are purified from acid citrate dextrose anti-coagulated peripheral blood by 2% gelatin sedimentation as previously described (Hurley, B. P. et al., *J. Immunol.* 173:5712-5720 (2004)). Red blood cells are removed by lysis in cold $NH_4Cl$ buffer, and neutrophils are washed with HBSS−/− (without $Ca^{2+}$ or $Mg^{2+}$) and resuspended to a final volume of $5\times10^7$/mL. 96 well HTS transwell filter plates (Corning), 3 μm pore size, are coated with 0.1 mg/mL rat tail collagen and allowed to dry overnight. Enriched $HXA_3$ (see above) is added to the lower well along with 1:10 dilution of vehicle control or a compound of the present technology at a pre-determined concentration. $5\times10^5$ neutrophils are added to the top well along with 1:10 vehicle or purified endocannabinoids, placed in a 37° C. incubator with 5% $CO_2$ and allowed to migrate for 2 hr. Top wells are removed, and transmigrated neutrophils are lysed with 1% Triton-X100. Sodium Citrate buffer (pH 4.2) is added to 0.1 M, and an equal volume of 2,2'-azino-bis(3-ethylbenzothiazoline-6-sulphonic acid) (ABTS) in 0.1 M Sodium citrate is added to samples. Myeloperoxidase (mpo) activity is measured. Neutrophil cell equivalents are calculated by comparison with a standard curve, and data from individual experiments are normalized to 100% $HXA_3$ migration. Data are mean+/−SEM from at least three independent experiments. Statistical analysis is performed using GraphPad Prism; data are analyzed by either one-way ANOVA or Mann-Whitney non-parametric U test as appropriate for experimental conditions.

It is expected that compounds of the present technology will exhibit a high degree of efficacy in inhibiting neutrophil migration in vitro, such as shown in Example 3, FIGS. 1D-1E. These results will demonstrate that compounds of the current technology are useful in methods for inhibiting neutrophil migration, such as in the prevention or treatment of diseases or conditions caused by, resulting in, or otherwise associated with neutrophil migration.

Example 12: Compounds of the Present Technology for the Prevention and Treatment of Colitis This example demonstrates the use of compounds of the present technology for the prevention and treatment of colitis in animal models and human subjects.

Animal Models

Animal models suitable for use in this example include, but are not limited to, animals having colitis, such as those described herein. One of skill in the art will understand that the following description is illustrative and may be applied as appropriate to other animal models.

General. C57BL/6 and cnr2−/− mice will be purchased from Jackson laboratories; FVB wt and mdr1a−/− will be purchased from Taconic. Female mice are used at age 6-12 weeks, and genotypes are mixed for at 2-4 weeks prior to experiments to equalize the microbiota. Mice are treated with 3% DSS (molecular weight 36,000-50,000, MP Biomedicals) in the drinking water for 7 days, then placed back on normal water and sacrificed at day 9, which represented peak disease. Samples from mid and distal colon are fixed in 10% formalin, paraffin-embedded, sectioned, and stained for histopathological analysis with hematoxylin and eosin. Each sample is graded semi-quantitatively from 0 to 3 for four criteria: (1) degree of epithelial hyperplasia and goblet cell depletion; (2) leukocyte infiltration in the lamina propria; (3) area of tissue affected; and (4) the presence of markers of severe inflammation such as crypt abscesses, submucosal inflammation, and ulcers. Samples are scored by a trained investigator blinded to sample identity, and mid and distal values are averaged to give colon histopathology score.

Subjects are administered compounds of the present technology according to methods described herein, such as by intrarectal administration. In some embodiments, the compound is administered once daily, once weekly, or once monthly. In some embodiments, compounds are administered multiple times daily, multiple times weekly, or multiple times monthly. Control subjects are administered vehicle alone.

Isolation of lamina propria leukocytes and flow cytometry. Cell suspensions from the lamina propria are prepared as described previously (Buonocore et al., 2010). Intestinal tissue is cut into small pieces, treated with RPMI with 10% FBS and 5 mM EDTA to remove epithelial cells, and then incubated with 100 U/mL Collagenase Type VIII (Sigma-Aldrich) for two 1 hr periods. Cells are then applied to a discontinuous 30/40/75% gradient of Percoll (GE Healthsciences) and harvested from the 40/70% interface. Cells are washed in PBS/0.1% BSA, incubated with anti-Fc receptor (αCD16/32, eBioscience) and stained with Zombie Live/Dead infrared stain (eBioscience) then surface stained with antibodies to CD45, CD11b, Ly6G, and Ly6C or Gr1. Samples are run on a MACSquant Analyzer 10 (Miltenyi Bioscience) and analyzed using Flowjo software Version 10 (Treestar).

Analysis of myeloperoxidase content in mouse samples. Samples are assayed for myeloperoxidase activity as described. Tissue sections of colon are frozen in liquid $N_2$ and stored at −80° C. until use. Sections are put in hexadecyl trimethyl ammonium bromide (HTAB, Sigma) buffer with lysing matrix D (MP Biomedicals) and homogenized with a FastPrep-24 homogenizer at level 6 for 40 s. Samples are combined with ABTS and fluorescence read over 8 min. Slopes are calculated by linear regression using Graphpad Prism, and normalized to protein content for individual samples as measured by Bicinchonic Acid assay (BioRad). For analysis of fecal samples, fecal contents are weighed and HTAB buffer added at a ratio of 10 μL/mg, and calculated slopes are used directly.

Mass spectrometric analysis of $HXA_3$ in colonic mucosa. Mice are administered 5% DSS in their drinking water and sacrificed on day 7. The proximal colon from untreated or DSS-treated mice (9 mice/cohort) is harvested and three intestinal segments pooled. Mucosal scrapings are collected by scraping intestinal surfaces with a rubber policeman in PBS, and $HXA_3$ content is analyzed as previously described (Mumy, K. L. et al., *Infect. Immun.* 76:3614-3627 (2008).

Results. It is expected that intrarectal administration of compounds of the present technology will significantly reduce intestinal pathology and colon shortening induced by DSS as compared to control animals. Analysis of colon histopathology will show that mice treated with the compounds have reduced neutrophil infiltration into the colonic lumen, which will be confirmed by a significant reduction in myeloperoxidase in fecal samples.

Accordingly, these results show that the compounds of the present technology are useful in methods of reducing neutrophil infiltration in vivo, such as in the prevention and treatment of inflammatory condition associated with neutrophil migration, such as colitis.

Human Subjects

Human subjects diagnosed as having or suspected to have colitis or a related disorder and presently displaying one or more symptoms and/or pathologies of colitis or a related disorder, are recruited using selection criteria known and accepted in the art.

Methods of Prevention and Treatment: Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of colitis or related disorders and assessed for reversal of symptoms/pathologies or attenuation of expected symptoms/pathologies using methods known in the art.

Results: It is expected that compounds of the present technology will induce reversal of symptoms and/or pathologies of colitis and related disorders in human subjects. These results will show that compounds of the present technology are useful and effective for the prevention and treatment of such disorders.

Example 13: Compounds of the Present Technology for the Prevention and Treatment of Cystic Fibrosis This example demonstrates the use of compounds of the present technology for the prevention and treatment of cystic fibrosis in animal models and human subjects.

Animal Models

Animal models suitable for use in this example include cystic fibrosis animal models known in the art, including but not limited to murine, porcine, and ferret models having cystic fibrosis transmembrane conductance regulator (CFTR) mutations. One of skill in the art will understand that the following description is illustrative and may be applied as appropriate to other animal models.

Young adult female CF mice homozygous for the ΔF508 mutation in the 129/FVB outbred background and their wild-type littermates are housed in static isolator cages. In order to prevent intestinal obstruction CF mice are weaned to a liquid diet (Peptamen®, Nestlé Clinical Nutrition, France). Peptamen is replaced daily. Non-CF mice are fed with standard diet (Pavan Service-Carfil, Oud-Tournhout, Belgium) changed out once a week when cages are sanitized and furnished with fresh bedding. Demineralized and acidified water is supplied ad libitum. The genotype of each animal is checked at 21 days of age using Taqman quantitative PCR multiplex analysis (Taqman, ABI PRISM® 7700 Sequence Detection System, Applied Biosystems, Foster, CA, USA) of tail clip DNA. Primers and Minor Groove Binder (MGB) probes designed for allele specific PCR using Primer Express Software (Applied Biosystems, Foster City, CA, USA) as follows: forward primer=5'-TTTCTTGGATTATGCCGGGTA-3' (SEQ ID NO: 07); reverse prime=5'-GTTGGCAAGCTTTGACAACACT-3' (SEQ ID NO: 08); wild-type specific probe=5'-FAM-AAACACCAAAGATGATATT-MGB-3' (SEQ ID NO: 09); mutant specific probe=5'-VIC-AACACCAATAATATTTTC-MGB-3' (SEQ ID NO: 10).

Induction of lung inflammation. For methods of prevention, sex and weight-matched CF and normal homozygous wild-type mice, 10 to 14 weeks of age, are pre-treated with compounds of the present technology by inhalation of an aerosol once per day for 4 weeks. Control subjects are administered vehicle alone. Acute lung inflammation is induced by instillation into the trachea through the mouth, using a laryngoscope and fine pipette tip, of 10 μg/20 g body weight of LPS (Sigma Chemical, St. Louis, MO, USA) in 50 μl saline. Administration of compounds of the present technology is stopped when LPS is administered.

For methods of treatment, sex- and weight-matched CF and normal homozygous wild-type mice are administered LPS as described above with no pre-treatment. Following confirmation of lung inflammation, subjects are administered compounds of the present technology according to methods described herein. Control subjects are administered vehicle alone. Parameters of lung inflammation are assessed at the completion of treatment protocols using methods described herein or otherwise known in the art.

Bronchoalveolar lavage (BAL). At selected time points after LPS instillation, mice are sacrificed by i.p. injection of 20 mg sodium pentobarbital (Abbott, Chicago, IL, USA). BAL is performed by cannulating the trachea and lavaging with 1 ml sterile saline as described. The BAL fluid (BALF)

is centrifuged (250×g, 10 min, 4° C.) and the supernatant aliquoted and stored at −20° C. for further biochemical measurements. Differential cell counts are performed on cytospin preparations using DiffQuick staining (Dade, Brussels, Belgium).

Myeloperoxidase (MPO) activity. After BAL is performed, lungs are perfused via the right ventricle with saline and excised. MPO activity in lung homogenates is assessed at 490 nm over 10 min as previously described.

Lactate dehydrogenase (LDH). LDH activity in BALF samples is assessed spectrophotometrically using methods known in the art.

Cytokine assays. Mouse macrophage inflammatory protein (MIP)-2, (R&D Systems, Minneapolis, MN, USA), tumor necrosis factor (TNF)-α and IL-10 (BD Pharmingen, San Diego, CA, USA) concentrations are measured in BALF using a standard sandwich enzyme-linked immunosorbent assay (ELISA) following the respective manufacturer's protocols.

Histopathology. Non-lavaged whole lungs are excised and inflation fixed via the trachea in 4% buffered paraformaldehyde and processed at 5 μm thickness for light microscopy. Slides are stained with hematoxilin and eosin or with Masson trichrome stain.

Bacteriology. BALF samples are plated onto Columbia agar base with 5% sheep blood, a polyvalent non-selective medium. Sabouraud agar (Becton Dickinson, Franklin Lakes, NJ, USA) and Mac Conkey culture media is used to select for yeasts and fungi and for Gram negative bacteria, respectively. Plates are placed in a traditional incubator at 35° C. for a minimum of 24 h. All tests are performed in duplicate.

Statistics. Results are expressed as means±SEM. Statistical data are analyzed using SAS-JMP software (SAS Institute, Cary, NC, USA). Between-group comparisons are evaluated using one-way analysis of variance. Posthoc comparisons are made using Student's t test or Tukey-Kramer HSD test, as appropriate. Null hypothesis are rejected at $p<0.05$. The alpha level is adjusted following Benferroni correction for pooled data from different experiments after identifying that means of normally distributed variables are not different (t test) and variances of populations are homogeneous (Snedecor's F test).

Results. It is predicted that administration of compounds of the present technology will be effective for the treatment and prevention of lung inflammation cystic fibrosis animal models. These results will show that compounds of the present technology are useful for methods of treating cystic fibrosis and treating/preventing lung inflammation associated with the disease.

Human Subjects

Human subjects diagnosed as having or suspected to have cystic fibrosis and presently displaying one or more symptoms and/or pathologies of cystic fibrosis, are recruited using selection criteria known and accepted in the art.

Methods of Prevention and Treatment. Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of cystic fibrosis and assessed for reversal of symptoms/pathologies or attenuation of expected symptoms/pathologies using methods known in the art. For example, subjects are administered compounds of the present technology prior to or subsequent to the development of lung inflammation associated with cystic fibrosis. Subjects are then assessed for prevention, reversal, or attenuation of lung inflammation using methods known in the art Results. It is expected that compounds of the present technology will induce reversal of symptoms and/or pathologies of cystic fibrosis such as lung inflammation in human subjects. These results will show that compounds of the present technology are useful and effective for the prevention and treatment of cystic fibrosis and cystic fibrosis associated lung inflammation.

Example 14: Compounds of the Present Technology for the Prevention and Treatment of Neutrophil-Mediated Skin Disorders This example demonstrates the use of compounds of the present technology for the prevention and treatment of neutrophil-mediated skin disorders such as dermatitis (eczema), rosacea, seborrheic dermatitis, and psoriasis in animal models and human subjects. One of skill in the art will understand that the example set forth below relating to psoriasis is illustrative of neutrophil-mediated skin disorders, with methods generally applicable to any neutrophil-mediated skin disorder.

Animal Models

Animal models suitable for this example include any accepted psoriasis model, including, but not limited to, models having spontaneous mutations, genetically engineered animals, immunological models, and pharmacological models. Spontaneous mutation models include but are not limited to mice homozygous for the asebia ($Scd1^{ab}/Scd1^{ab}$), chronic proliferative dermatitis ($Sharpin^{cpdm}/Sharpin^{cpdm}$), flaky skin ($Ttc7^{fsn}/Ttc7^{fsn}$) mutations. Genetically engineered models include animals ectopically expressing key regulatory molecules or lacking key regulatory molecules as known in the art. Immunological models include animal subjects subjected to adoptive transfer or related methods as known in the art. Pharmacological models include subjects administered agents that induce psoriasis or psoriasis-related conditions. For example, subjects topically administered imiquimod (IMQ), a toll-like receptor (TLR)-7 and TLR-8 agonist.

One of skill in the art will understand that the following description is illustrative and may be applied as appropriate to other animal models.

Materials. Imiquimod (IMQ, 5% cream, Beselna®) is purchased from Mochida Pharmaceutical (Tokyo, Japan). Betamethasone butyrate propionate (0.05% ointment, Antebate®) is purchased from Torii Phar maceutical (Tokyo, Japan). Real-time PCR probes and related agents is purchased from Applied Biosystems (Massachusetts, USA).

Animals. Female BALB/c mice and male CB-17 scid mice aged 7-12 weeks old are housed under specific pathogen-free conditions at a room temperature of 23±3° C. and air humidity of 55±15% in a 12-hour light/dark cycle environment, and provided with food and water ad libitum.

Induction of skin inflammation. IMQ 5% cream is applied on inner and/or outer sides of the left ear skin once daily. The dose of IMQ is either 250 μg on outer side, 500 μg on outer side, or 250 μg on both inner and outer sides of the ear. Betamethasone ointment or relevant ointment base is applied twice daily on to the left ear, at a volume of 5 μL to both the inner and/or outer sides. Thickness of the left ear is measured as a quantitative index of skin inflammation utilizing a thickness gauge (IDA-112M, Mitutoyo, Kawasaki, Japan) once daily before the application of IMQ. Control subjects are administered vehicle alone.

For methods of prevention, subjects are pre-treated with compounds of the present technology by topical application for a pre-determined period prior to IMQ exposure.

For methods of treatment, subjects are topically administered compounds of the present technology for a pre-determined period following confirmation of IMQ-induced inflammation using methods known in the art.

Subjects are euthanized by carbon dioxide gas, and the left ear harvested after examination of gross morphology for erythema and scaling. A portion of the harvested tissue is sliced, fixed with buffered 10% formalin solution, and processed for preparation of histological paraffin sections. The sections are stained with hematoxyline and eosin, and subjected to light microscopic examination. The remaining tissue is stored at −80° C. for mRNA analysis by real time PCR.

Real time PCR assays. Total RNA samples in the ear tissues are obtained with RNeasy® Lipid Tissue Mini Kit (QIAGEN, Venlo, the Netherlands), following the manufacturer's instructions. The level of transcripts coding cytokines of interest in the present study are measured by the TaqMan Gene Expression Assays using the RNA-to-Ct™ 1-Step Kit.

Illustrative targets include but are not limited to IFN-γ, IL-13, IL-17, IL-22, IL-23, TNF-α, and IL-1β. Target transcript levels are normalized to GAPDH transcript levels.

Statistical Analysis. Values of ear thickness are shown as increases from the pre-treatment values measured at Day 1 and expressed as mean±standard deviation (S.D.). Statistical significance is analyzed by F-test followed by Aspin-Welch's t-test and Bartlett's test followed by Dunnett's test or Steel test in ear thicknesses, and by Bartlett's test followed by Tukey's test or Steel-Dwass test in mRNA transcript levels. A p value of less than 0.05 was considered statistically significant.

Results. It is predicted that administration of compounds of the present technology will prevent or reduce IMQ-induced inflammation as measured by tissue thickness, inflammatory gene expression, and dermal neutrophil infiltration. These results will show that compounds of the present technology are useful in the prevention and treatment of conditions associated with inflammation and dermal neutrophil infiltration, including but not limited to dermatitis (eczema), rosacea, seborrheic dermatitis, and psoriasis.

Human Subjects

Human subjects diagnosed as having or suspected to have a neutrophil-mediated skin disorder, such as dermatitis (eczema), rosacea, seborrheic dermatitis, or psoriasis, and presently displaying one or more symptoms and/or pathologies of the disorder, are recruited using selection criteria known and accepted in the art.

Methods of Prevention and Treatment. Subjects are administered compounds of the present technology at a dosage and frequency commensurate with the stage and severity of disease. In some embodiments a compound is administered once daily, once weekly, or once monthly. In some embodiments, a compound is administered multiple times daily, weekly, or monthly.

To demonstrate methods of prevention and treatment in humans, subjects are administered compounds of the present technology prior to or subsequent to the development of symptoms and/or pathologies of neutrophil-mediated skin disorder and assessed for reversal of symptoms/pathologies or attenuation of expected symptoms/pathologies using methods known in the art. For example, subjects are administered compounds of the present technology prior to or subsequent to the development of a neutrophil-mediated skin disorder or symptoms thereof. Subjects are then assessed for prevention, reversal, or attenuation of the disorder or symptom using methods known in the art.

Results. It is expected that compounds of the present technology will induce reversal of symptoms and/or pathologies of neutrophil-mediated skin disorders, such as dermatitis (eczema), rosacea, seborrheic dermatitis, and psoriasis. These results will show that compounds of the present technology are useful and effective for the prevention and treatment of neutrophil-mediated skin disorders in human subjects.

REFERENCES

1. Mrsny, R. J. et al. Identification of hepoxilin A3 in inflammatory events: a required role in neutrophil migration across intestinal epithelia. *Proc. Natl. Acad. Sci. U.S.A* 101, 7421-6 (2004).
2. Pazos, M. et al. Multidrug resistance-associated transporter 2 regulates mucosal inflammation by facilitating the synthesis of hepoxilin A3. *J. Immunol.* 181, 8044-52 (2008).
3. Boll, E. J. et al. Enteroaggregative *Escherichia coli* promotes transepithelial migration of neutrophils through a conserved 12-lipoxygenase pathway. *Cell. Microbiol.* 14, 120-32 (2012).
4. Mumy, K. L. et al. Distinct isoforms of phospholipase A2 mediate the ability of *Salmonella enterica* serotype *typhimurium* and *Shigella flexneri* to induce the transepithelial migration of neutrophils. *Infect. Immun.* 76, 3614-27 (2008).
5. Hurley, B. P., Siccardi, D., Mrsny, R. J. & Mccormick, B. A. Polymorphonuclear Cell Transmigration Induced by *Pseudomonas aeruginosa* Requires the Eicosanoid Hepoxilin A 3. *J. Immunol.* 173, 5712-5720 (2004).
6. Okayasu, I. et al. A Novel Method in the Induction of Reliable Experimental Acute and Chronic Ulcerative Colitis in Mice. *Gastroenterology* 98, 694-702 (1990).
7. Siccardi, D., Mumy, K. L., Wall, D. M., Bien, J. D. & McCormick, B. A. *Salmonella enterica* serovar *Typhimurium* modulates P-glycoprotein in the intestinal epithelium. *Am. J. Physiol. Gastrointest. Liver Physiol.* 294, G1392-400 (2008).
8. Brant, S. R. et al. MDR1 Ala893 polymorphism is associated with inflammatory bowel disease. *Am. J. Hum. Genet.* 73, 1282-92 (2003).
9. Ho, G., Gaya, D. R. & Satsangi, J. Multidrug Resistance (MDR1) Gene in Inflammatory Bowel Disease: A Key Player? *Inflamm. Bowel Dis.* 11, 1013-1019 (2005).
10. Brinar, M. et al. MDR1 polymorphisms are associated with inflammatory bowel disease in a cohort of Croatian IBD patients. *BMC Gastroenterol.* 13, 57 (2013).
11. Panwala, C. M., Jones, J. C. & Viney, J. L. A novel model of inflammatory bowel disease: mice deficient for the multiple drug resistance gene, mdr1a, spontaneously develop colitis. *J. Immunol.* 161, 5733-44 (1998).
12. Wilk, J. N., Bilsborough, J. & Viney, J. L. The mdr1a−/− Mouse Model of Spontaneous Colitis. *Immunol.* Res. 31, 151-159 (2005).
13. Yusa, K., Tsuruo, T., Yusa, K. & Tsuruo, T. Reversal Mechanism of Multidrug Resistance by Verapamil: Direct Binding of Verapamil to P-Glycoprotein on Specific Sites and Transport of Verapamil Outward across the Plasma Membrane of K562/ADM Cells Reversal Mechanism of Multidrug Resistance by Verap. 5002-5006 (1989).

14. Ryberg, E. et al. The orphan receptor GPR55 is a novel cannabinoid receptor. *Br. J. Pharmacol.* 152, 1092-1101 (2007).
15. Syed, S. K. et al. Regulation of GPR119 receptor activity with endocannabinoid-like lipids. *Am. J. Physiol. Endocrinol. Metab.* 303, E1469-78 (2012).
16. Patricelli, M. P. & Cravatt, B. F. Characterization and manipulation of the acyl chain selectivity of fatty acid amide hydrolase. Biochemistry 40, 6107-15 (2001).
17. Dinh, T. P. et al. Brain monoglyceride lipase participating in endocannabinoid inactivation. *Proc. Natl. Acad. Sci. U.S.A* 99, 10819-24 (2002).
18. Chicca, A., Marazzi, J., Nicolussi, S. & Gertsch, J. Evidence for bidirectional endocannabinoid transport across cell membranes. *J. Biol. Chem.* 287, 34660-34682 (2012).
19. Staley, E. M., Schoeb, T. R. & Lorenz, R. G. Differential susceptibility of P-glycoprotein deficient mice to colitis induction by environmental insults. *Inflamm. Bowel Dis.* 15, 684-96 (2009).
20. Singh, U. P. et al. Cannabinoid receptor-2 (CB2) agonist ameliorates colitis in IL-10(−/−) mice by attenuating the activation of T cells and promoting their apoptosis. *Toxicol. Appl. Pharmacol.* 258, 256-67 (2012).
21. Pulli, B. et al. Measuring myeloperoxidase activity in biological samples. *PLOS One* 8, e67976 (2013).
22. Bhowmick, et al., *J Immunol,* 191(10):5115-5123 (2013) .]).
23. Pazos, et al., *J Immunol,* 181(11):8044-8052 (2008).]).
24. Van Schilfgaarde, et al., *Infection and Immunity* 1995; 63(12): 4729-4737.
25. Galka, et al., *Infection and Immunity."* 2008; 76(5): 1825-1836.
26. Clark, et al., *Clinical and Vaccine Immunology* 2009; 16(3): 397-407.
27. Sakamoto, et al., *Journal of Pharmaceutical Sciences* 2015; 104(9): 1-10.
28. Stolarczyk, et al., *Current Pharmaceutical Biotechnology* 2011; 12(4): 621-635.
29. Westlake, et al., *Molecular Biology of the Cell* 2005; 16: 2483-2492.
30. Agbor, et al., *Cell Microbiol,* 13(12):2007-2021 (2011).
31. Strohmeier, et al., *Journal of Clininical Investigation* 1997; 99: 2588-2601.
32. Torky, et al., *Toxicology* 2005; 207: 437-450.
33. Parkos, et al., *Molecular Medicine* 1996; 2(4): 489-505.
34 Parkos, et al., *Journal of Clinical Investigation* 1991; 88(5): 1605-1612.
35. Chiavolini, et al., *Clinical Microbiology Reviews* 2008; 21(4): 666-685.

Each and every publication and patent mentioned in the above specification is herein incorporated by reference in its entirety for all purposes. Various modifications and variations of the described methods and system of the present technology will be apparent to those skilled in the art without departing from the scope and spirit of the present technology. Although the present technology has been described in connection with specific embodiments, the present technology as claimed should not be unduly limited to such specific embodiments. Indeed, various modifications of the described modes for carrying out the present technology which are obvious to those skilled in the art and in fields related thereto are intended to be within the scope of the following claims.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A compound having the formula:

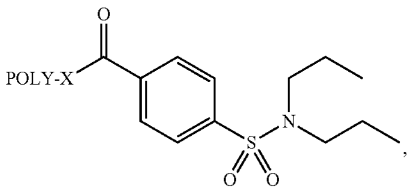

wherein X is a $C_6$ linker and POLY is a polymer.

2. The compound of claim 1, wherein said $C_6$ linker is selected from the group consisting of a substituted or unsubstituted alkylene, a cycloakylene, a cycloalkylalkylene, a heteroalkylene, an alkenylene, and a heteroalkenylene group.

3. The compound of claim 1, wherein POLY is a polymer selected from the group consisting of: dextran, polyethylene glycol (PEG), periodate-oxidized dextran, polysialic acids (PSAs), hyaluronic acid (HA), dextrin, hydroxyethyl-starch (HES), poly(2-ethyl 2-oxazoline) (PEOZ), polyglutamic acid (PGA), polylactic acid (PLA), polylactic-co-glycolic (PLGA), poly(D,L-lactide-co-glycolide) (PLA/PLGA), poly (hydroxyalkylmethaacrylamide), polyglycerol, 25 polyamidoamine (PAMAM), polyethylenimine (PEI), polypeptides, and any combination thereof.

4. A pharmaceutical composition comprising a therapeutically effective amount of the compound of claim 1 and a pharmaceutically acceptable carrier.

5. A method for treating or preventing inflammation in a subject in need thereof, comprising administering to the subject a therapeutically effective amount of the compound of claim 1.

6. The method of claim 5, wherein the treatment reduces the number of neutrophils migrating in a basolateral-to-apical direction.

* * * * *

SEQUENCE LISTING

```
Sequence total quantity: 10
SEQ ID NO: 1            moltype = DNA  length = 2335
FEATURE                 Location/Qualifiers
source                  1..2335
                        mol_type = genomic DNA
                        organism = Homo sapiens
SEQUENCE: 1
cggctcccct cgcctaagct gctgggggc gccatgggcc gctaccgcat ccgcgtggcc  60
accggggcct ggctcttctc cgggtcgtac aaccgcgtgc agctttggct ggtcgggacg  120
cgcggggagg cggagctgga gctgcagctg cggccggcgc ggggcgagga ggaggagttt  180
gatcatgacg ttgcagagga cttggggctc ctgcagttcg tgaggctgcg caagcaccac  240
tggctggtgg acgacgcgtg gttctgcgac cgcatcacgg tgcagggccc tggagcctgc  300
gcggaggtgg ccttcccgtg ctaccgctgg gtgcagggcg aggacatcct gagcctgccc  360
gagggcaccg cccgcctgcc aggagacaat gctttggaca tgttccagaa gcatcgagag  420
aaggaactga aagacagaca gcagatctac tgctgggcca cctggaagga agggttaccc  480
ctgaccatcg ctgcagaccg taaggatgat ctacctccaa atatgagatt ccatgaggag  540
aagaggctgg actttgaatg gacactgaag gcaggggctc tggagatggc cctcaaacgt  600
gtttacaccc tcctgagctc ctggaactgc ctagaagact ttgatcagat cttctggggc  660
cagaagagtg ccctggctga gaaggttcgc cagtgctggc aggatgatga gttgttcagc  720
taccagttcc tcaatggtgc caaccccatg ctgttgagac gctcgacctc tctgccctcc  780
aggctagtgc tgccctcagg gatggaagag cttcgggctc aactggagaa agaacttcag  840
aatggttccc tgtttgaagc tgacttcatc cttctggatg gaattccagc caacgtgatc  900
```

```
cgaggagaga agcaatacct ggctgccccc ctcgttatgc tgaagatgga gcccaatggg  960
aagctgcagc ccatggtcat ccagattcag cctcccaacc ccagctctcc aaccccaaca  1020
ctgttcctgc cctcagaccc cccacttgcc tggctcctgg caaagtcctg ggtccgaaat  1080
tcagatttcc aactgcacga gatccagtat cacttgctga acacgcacct ggtggctgag  1140
gtcatcgctg tcgccaccat gcggtgcctc ccaggactgc accccatctt caagttcctg  1200
atcccccata tccgctacac catggaaatc aacacccggg cccggaccca actcatctca  1260
gatggaggaa tttttgataa ggcagtgagc acaggtggag ggggccatgt acagttgctc  1320
cgtcgggcgg cagctcagct gacctactgc tccctctgtc ctcctgacga cctggctgac  1380
cggggcctgc tgggactccc aggtgctctc tatgcccatg atgctttacg gctctgggag  1440
atcattgcca ggtatgtgga ggggatcgtc cacctcttct accaaaggga tgacatagtg  1500
aagggggacc ctgagctgca ggcctggtgt cgggagatca cggaggtggg gctgtgccag  1560
gcccaggacc gaggtttccc tgtctccttc cagtcccaga gtcaactctg ccatttcctc  1620
accatgtgcg tcttcacgtg cactgcccag catgccgcca tcaaccaggg ccagctggac  1680
tggtatgcct gggtccctaa tgctccatgc acaatgcgga tgcccccacc caccaccaag  1740
gaagatgtga cgatggccac agtgatgggg tcactacctg atgtccggca ggcctgtctt  1800
caaatggcca tctcatggca tctgagtcgc cgccagccag acatggtgcc tctggggcac  1860
cacaaagaaa aatatttctc aggccccaag cccaaagctg tgctaaacca attccgaaca  1920
gatttggaaa agctggaaaa ggagattaca gcccggaatg agcaacttga ctggccctat  1980
gaatatctga agcccagctg catagagaac agtgtcacca tctgagccct agagtgactc  2040
tacctgcaag atttcacatc agctttagga ctgacatttc tatcttgaat ttcatgcttt  2100
cctaaagtct ctgctgctaa ggctctattt cctcccccag ttaaaccccc tacattagta  2160
tcccactagc ccaggggagc agtaaacttt ctctgcaaag actagatcct tttttacgct  2220
ttgcagaccg catagtcact gtctcaacta ctcagctctc ctgctgcagc atgaaggcag  2280
ccacagacaa catggaaatg agtgtgacta tgttccaata aaactttatg gacac       2335

SEQ ID NO: 2           moltype = DNA  length = 5446
FEATURE                Location/Qualifiers
source                 1..5446
                       mol_type = genomic DNA
                       organism = Homo sapiens
SEQUENCE: 2
tactttggga actggtgagt ctccctgtcc ctagggcttt ttagtcacat gtccatccac  60
tgtttcaatg taacatgcat ctaggcaagg ttaacgatta aatggttggg atgaaaggtc  120
atcctttacg gagaacatca gaatggtaga taattcctgt tccactttct ttgatgaaac  180
aagtaaagaa gaaacaacac aatcatatta atagaagagt cttcgttcca gacgcagtcc  240
aggaatcatg ctggagaagt tctgcaactc tactttttgg aattcctcat tcctggacag  300
tccggaggca gacctgccac tttgttttga gcaaactgtt ctggtgtgga ttcccttggg  360
cttcctatgg ctcctggccc cctggcagct tctccacgtg tataaatcca ggaccaagag  420
atcctctacc accaaactct atcttgctaa gcaggtattc gttggttttc ttcttattct  480
agcagccata gagctggccc ttgtactcac agaagactct ggacaagcca cagtccctgc  540
tgttcgatat accaatccaa gcctctacct aggcacatgg ctcctggttt tgctgatcca  600
atacagcaga caatggtgtg tacagaaaaa ctcctggttc ctgtccctat tctggattct  660
ctcgatactc tgtggcactt tccaatttca gactctgatc cggacactct tacagggtga  720
caattctaat ctagcctact cctgcctgtt cttcatctcc tacggattcc agatcctgat  780
cctgatcttt tcagcatttt cagaaaataa tgagtcatca aataatccat catccatagc  840
ttcattcctg agtagcatta cctacagctg gtatgacagc atcattctga aaggctacaa  900
gcgtcctctg acactcgagg atgtctggga agttgatgaa gagatgaaaa ccaagacatt  960
agtgagcaag tttgaaacgc acatgaagag agagctgcag aaagccaggc gggcactcca  1020
gagacggcag gagaagagct cccagcagaa ctctggagcc aggctgcctg gcttgaacaa  1080
gaatcagagt caaagccaag atgcccttgt cctggaagat gttgaaaaga aaaaaaagaa  1140
gtctgggacc aaaaaagatg ttccaaaatc ctggttgatg aaggctctgt tcaaaacttt  1200
ctacatggtg ctcctgaaat cattcctact gaagctagtg aatgacatct tcacgtttgt  1260
gagtcctcag ctgctgaaat tgctgatctc ctttgcaagt gaccgtgaca catatttgtg  1320
gattggatat ctctgtgcaa tcctcttatt cactgcggct ctcattcagt ctttctgcct  1380
tcagtgttat ttccaactgt gcttcaagct gggtgtaaaa gtacggacag ctatcatggc  1440
ttctgtatat aagaaggcat tgaccctatc caacttggcc aggaaggagt acaccgttgg  1500
agaaacagtg aacctgatgt ctgtggatgc ccagaagctc atggatgtga ccaacttcat  1560
gcacatgctg tggtcaagtg ttctacagat tgtcttatct atcttcttcc tatggagaga  1620
gttgggaccc tcagtcttag caggtgttgg ggtgatggtg cttgtaatcc caattaatgc  1680
gatactgtcc accaagagta agaccattca ggtcaaaaat atgaagaata aagacaaacg  1740
tttaaagatc atgaatgaga ttcttagtgg aatcaagatc ctgaaatatt ttgcctggga  1800
accttcattc agagaccaag tacaaaacct ccggaagaaa gagctcaaga acctgctggc  1860
ctttagtcaa ctacagtgtg tagtaatatt cgtcttccag ttaactccag tcctggtatc  1920
tgtggtcaca ttttctgttt atgtcctggt ggatagcaac aatattttgg atgcacaaaa  1980
ggccttcacc tccattaccc tcttcaatat cctgcgcttt cccctgagca tgcttcccat  2040
gatgatctcc tccatgctcc aggccagtgt ttccacagag cggctagaga agtacttggg  2100
aggggatgac ttggacacat ctgccattcg acatgactgc aattttgaca aagccatgca  2160
gttttctgag gcctccttta cctgggaaca tgattcggaa gccacagtcc gagatgtgaa  2220
cctggacatt atggcaggcc aacttgtggc tgtgataggc cctgtcggct ctgggaaatc  2280
ctccttgata tcagccatgc tgggagaaat ggaaaatgtc cacgggcaca tcaccatcaa  2340
gggcaccact gcctatgtcc cacagcagtc ctggattcag aatggcacca taaaggacaa  2400
catccttttt ggaacagagt ttaatgaaaa gaggtaccag caagtactgg aggcctgtgc  2460
tctcctccca gacttggaaa tgctgcctgg aggagatttg gctgagattg gagagaaggg  2520
tataaatctt agtgggggtc agaagcagcg gatcagcctg gccagagcta cctaccaaaa  2580
tttagacatc tatcttctag atgacccccct gtctgcagtg gatgctcatg taggaaaaca  2640
tatttttaat aaggtcttgg gccccaatgg cctgttgaaa ggcaagactc gactcttggt  2700
tacacatagc atgcactttc ttcctcaagt ggatgagatt gtagttctgg ggaatggaac  2760
aattgtagag aaaggatcct acagtgctct cctggccaaa aaaggagagt ttgctaagaa  2820
tctgaagaca tttctaagac atacaggccc tgaagaggaa gccacagtcc atgatggcag  2880
```

-continued

```
tgaagaagaa gacgatgact atgggctgat atccagtgtg gaagagatcc ccgaagatgc  2940
agcctccata accatgagaa gagagaacag ctttcgtcga acacttagcc gcagttctag  3000
gtccaatggc aggcatctga agtccctgag aaactccttg aaaactcgga atgtgaatag  3060
cctgaaggaa gacgaagaac tagtgaaagg acaaaaacta attaagaagg aattcataga  3120
aactggaaag gtgaagttct ccatctacct ggagtaccta caagcaatag gattgttttc  3180
gatattcttc atcatccttg cgtttgtgat gaattctgtg gcttttattg gatccaacct  3240
ctggctcagt gcttggacca gtgactctaa aatcttcaat agcaccgact atccagcatc  3300
tcagagggac atgagagttg gagtctacgg agctctggga ttagcccaag gtatatttgt  3360
gttcatagca catttctgga gtgcctttgg tttcgtccat gcatcaaata tcttgcacaa  3420
gcaactgctg aacaatatcc ttcgagcacc tatgagattt tttgacacaa cacccacagg  3480
ccggattgtg aacaggtttg ccggcgatat ttccacagtg gatgacaccc tgcctcagtc  3540
cttgcgcagc tggattacat gcttcctggg gataatcagc acccttgtca tgatctgcat  3600
ggccactcct gtcttcacca tcatcgtcat tcctcttggc attatttatg tatctgttca  3660
gatgttttat gtgtctacct cccgccagct gaggcgtctg gactctgtca ccaggtcccc  3720
aatctactct cacttcagcg agaccgtatc aggtttgcca gttatccgtg cctttgagca  3780
ccagcagcga tttctgaaac acaatgaggt gaggattgac accaaccaga aatgtgtctt  3840
ttcctggatc acctccaaca ggtggcttgc aattcgcctg gagctggttg ggaacctgac  3900
tgtcttcttt tcagccttga tgatggttat ttatagagat accctaagtg gggacactgt  3960
tggctttgtt ctgtccaatg cactcaatat cacacaaacc ctgaactggc tggtgaggat  4020
gacatcagaa atagagacca acattgtggc tgttgagcga ataactgagt acacaaaagt  4080
ggaaaatgag gcaccctggg tgactgataa gaggcctccg ccagattggc ccagcaaagg  4140
caagatccag tttaacaact accaagtgcg gtaccgacct gagctggatc tggtcctcag  4200
agggatcact tgtgacatcg gtagcatgga gaagattggt gtggtgggca ggacaggagc  4260
tggaaagtca tccctcacaa actgcctctt cagaatctta gaggctgccg gtggtcagat  4320
tatcattgat ggagtagata ttgcttccat tgggctccac gacctccgag agaagctgac  4380
catcatcccc caggacccca tcctgttctc tggaagcctg aggatgaatc tcgacccttt  4440
caacaactac tcagatgagg agatttggaa ggccttggag ctggctcacc tcaagtcttt  4500
tgtggccagc ctgcaacttg ggttatccca cgaagtgaca gaggctggtg gcaacctgag  4560
cataggccag aggcagctgc tgtgcctggg cagggctctg cttcggaaat ccaagatcct  4620
ggtcctggat gaggccactg ctgcggtgga tctagagaca gacaacctca ttcagacgac  4680
catccaaaac gagttcgccc actgcacagt gatcaccatc gcccacaggc tgcacaccat  4740
catggacagt gacaaggtaa tggtcctaga caacgggaag attatagagt gcggcagccc  4800
tgaagaactg ctacaaatcc ctggaccctt ttactttatg gctaaggaag ctggcattga  4860
gaatgtgaac agcacaaaat tctagcagaa ggccccatgg gttagaaaag gactataaga  4920
ataatttctt atttaatttt attttttata aaatacagaa tacatacaaa agtgtgtata  4980
aaatgtacgt tttaaaaaag gataagtgaa cacccatgaa cctactaccc aggttaagaa  5040
aataaatgtc accaggtact tgagaaaccc ctcgattgtc tacctcgatc gtacttcctt  5100
gctacccacc cctcccaggg acaaccactg tcctgaattt cacgataatt attcctttgc  5160
ctttcatttc tgttttatca cctttgtatg tatctttaaa caacatatac cctttttttac  5220
ttatgtaaat ggactgactc atactgcata catcttctat gacttgattc ttttgttcaa  5280
tattatatct gagattcatc catggtgatg caaataggtg cattattttt tttcactgct  5340
ctgtagtctg gcattgtatg aatacagcac aatgtatcag ttttaatatt ggggatcatt  5400
agcattattc tcaggttttt aaaaattata agcagtacta ctatgg                5446

SEQ ID NO: 3            moltype = DNA  length = 4718
FEATURE                 Location/Qualifiers
source                  1..4718
                        mol_type = genomic DNA
                        organism = Homo sapiens
SEQUENCE: 3
aaacacttgt attaccattt taaaggctat cattactctt tacctgtgaa gagtagaaca  60
tgaagaaatc tactttattc agatattctc cagattccta aagattagag atcatttctc  120
attctcctag gagtactcac ttcaggaagc aaccagataa aagagaggtg caacggaagc  180
cagaacattc ctcctggaaa ttcaacctgt ttcgcagttt ctcgaggaat cagcattcag  240
tcaatccggg ccgggagcag tcatctgtgg tgaggctgat tggctgggca ggaacagcgc  300
cggggcgtgg gctgagcaca gccgcttcgc tctctttgcc acaggaagcc tgagctcatt  360
cgagtagcgg ctcttccaag ctcaaagaag cagaggccgc tgttcgtttc ctttaggtct  420
ttccactaaa gtcggagtat cttcttccaa aatttcacgt cttggtggcc gttccaagga  480
gcgcgaggtc ggaatggatc ttgaagggga ccgcaatgga ggagcaaaga agaagaactt  540
ttttaaactg aacaataaaa gtgaaaaaga taagaaggaa aagaaaccaa ctgtcagtgt  600
attttcaatg tttcgctatt caaattggct tgacaagttg tatatggtgg tgggaacttt  660
ggctgccatc atccatgggg ctggacttcc tctcatgatg ctggtgtttg gagaaatgac  720
agatatcttt gcaaatgcag gaaatttaga agatctgatg tcaaacatca ctaatagaag  780
tgatatcaat gatacagggt tcttcatgaa tctggaggaa gacatgacca ggtatgccta  840
ttattacagt ggaattggtg ctggggtgct ggttgctgct tacattcagg tttcattttg  900
gtgcctggca gctggaagac aaatacacaa aattagaaaa cagtttttc atgctataat  960
gcgacaggag ataggctggt ttgatgtgca cgatgttggg gagcttaaca cccgacttac  1020
agatgatgtc tccaagatta atgaaggaat tggtgacaaa attggaatgt tctttcagtc  1080
aatggcaaca tttttcactg ggtttatagt aggatttaca cgtggttgga agctaaccct  1140
tgtgattttg gccatcagtc ctgttcttgg actgtcagct gctgtctggg caaagatact  1200
atcttcattt actgataaag aactcttagc gtatgcaaaa gctggagcag tagctgaaga  1260
ggtcttggca gcaattagaa ctgtgattgc atttggagga caaaagaaag aacttgaaag  1320
gtacaacaaa aatttagaag aagctaaaag aattgggata aagaaagcta ttacagccaa  1380
tatttctata ggtgctgctt tcctgctgat ctatgcatct tatgctctgg ccttctggta  1440
tgggaccacc ttggtcctct caggggaata ttctattgga caagtactca ctgtattctt  1500
ttctgtatta attggggctt ttagtgttgg acaggcatct ccaagcattg aagcatttgc  1560
aaatgcaaga ggagcagctt atgaaatctt caagataatt gataataagc caagtattga  1620
cagctattcg aagagtgggc acaaaccaga taatattaag ggaaatttgg aattcagaaa  1680
tgttcacttc agttacccat ctcgaaaaga agttaagatc ttgaagggtc tgaacctgaa  1740
```

-continued

```
ggtgcagagt gggcagacgg tggccctggt tggaaacagt ggctgtggga agagcacaac  1800
agtccagctg atgcagaggc tctatgaccc cacagagggg atggtcagtg ttgatggaca  1860
ggatattagg accataaatg taaggtttct acgggaaatc attggtgtgg tgagtcagga  1920
acctgtattg tttgccacca cgatagctga aaacattcgc tatggccgtg aaaatgtcac  1980
catggatgag attgagaaag ctgtcaagga agccaatgcc tatgacttta tcatgaaact  2040
gcctcataaa tttgacaccc tggttggaga gagaggggcc cagttgagtg gtgggcagaa  2100
gcagaggatc gccattgcac gtgccctggt tcgcaacccc aagatcctcc tgctggatga  2160
ggccacgtca gccttggaca cagaaagcga agcagtggtt caggtggctc tggataaggc  2220
cagaaaaggt cggaccacca ttgtgatagc tcatcgtttg tctacagttc gtaatgctga  2280
cgtcatcgct ggtttcgatg atggagtcat tgtggagaaa ggaaatcatg atgaactcat  2340
gaaagagaaa ggcatttact tcaaacttgt cacaatgcag acagcaggaa atgaagttga  2400
attagaaaat gcagctgatg aatccaaaag tgaaattgat gccttggaaa tgtcttcaaa  2460
tgattcaaga tccagtctaa taagaaaaag atcaactcgt aggagtgtcc gtggatcaca  2520
agcccaagac agaaagctta gtaccaaaga ggctctggat gaaagtatac ctccagtttc  2580
cttttggagg attatgaagc taaatttaac tgaatggcct tattttgttg ttggtgtatt  2640
ttgtgccatt ataaatggag gcctgcaacc agcatttgca ataatatttt caaagattat  2700
aggggttttt acaagaattg atgatcctga aacaaaacga cagaatagta acttgttttc  2760
actattgttt ctagcccttg gaattatttc ttttattaca tttttccttc agggtttcac  2820
atttggcaaa gctggagaga tcctcaccaa gcggctccga tacatggttt tccgatccat  2880
gctcagacag gatgtgagtt ggtttgatga ccctaaaaac accactggag cattgactac  2940
caggctcgcc aatgatgctg ctcaagttaa aggggctata ggttccaggc ttgctgtaat  3000
tacccagaat atagcaaatc ttgggacagg aataattata tccttcatct atggttggca  3060
actaacactg ttactcttag caattgtacc catcattgca atagcaggag ttgttgaaat  3120
gaaaatgttg tctggacaag cactgaaaga taagaaagaa ctagaaggtt ctgggaagat  3180
cgctactgaa gcaatagaaa acttccgaac cgttgtttct ttgactcagg agcagaagtt  3240
tgaacatatg tatgctcaga gtttgcaggt accatacaga aactctttga ggaaagcaca  3300
catctttgga attacatttt ccttcaccca ggcaatgatg tatttttcct atgctggatg  3360
tttccggttt ggagcctact tggtggcaca taaactcatg agctttgagg atgttctgtt  3420
agtattttca gctgttgtct ttggtgccat ggccgtgggg caagtcagtt catttgctcc  3480
tgactatgcc aaagccaaaa tatcagcagc ccacatcatc atgatcattg aaaaaacccc  3540
tttgattgac agctacagca cggaaggcct aatgccgaac acattggaag gaaatgtcac  3600
atttggtgaa gttgtattca actatcccac ccgaccggac atcccagtgc ttcagggact  3660
gagcctggag gtgaagaagg gccagacgct ggctctggtg ggcagcagtg gctgtgggaa  3720
gagcacagtg gtccagctcc tggagcggtt ctacgacccc ttggcaggga aagtgctgct  3780
tgatggcaaa gaaataaagc gactgaatgt tcagtggctc cgagcacacc tgggcatcgt  3840
gtcccaggag cccatcctgt ttgactgcag cattgctgag aacattgcct atggagacaa  3900
cagccgggtg gtgtcacagg aagagattgt gagggcagca aaggaggcca acatacatgc  3960
cttcatcgag tcactgccta ataaatatag cactaaagta ggagacaaag gaactcagct  4020
ctctggtggc cagaaacaac gcattgccat agctcgtgcc cttgttagac agcctcatat  4080
tttgcttttg gatgaagcca cgtcagctct ggatacagaa agtgaaaagg ttgtccaaga  4140
agccctggac aaagccagag aaggccgcac ctgcattgtg attgctcacc gcctgtccac  4200
catccagaat gcagacttaa tagtggtgtt tcagaatggc agagtcaagg agcatggcac  4260
gcatcagcag ctgctggcac agaaaggcat ctatttttca atggtcagtg tccaggctgg  4320
aacaaagcgc cagtgaactc tgactgtatg agatgttaaa tactttttaa tatttgttta  4380
gatatgacat ttattcaaag ttaaaagcaa acacttacag aattatgaag aggtatctgt  4440
ttaacatttc ctcagtcaag ttcagagtct tcagagactt cgtaattaaa ggaacagagt  4500
gagagacatc atcaagtgga gagaaatcat agtttaaact gcattataaa ttttataaca  4560
gaattaaagt agattttaaa agataaaatg tgtaattttg tttatatttt cccatttgga  4620
ctgtaactga ctgccttgct aaaagattat agaagtagca aaaagtattg aaatgtttgc  4680
ataaagtgtc tataataaaa ctaaactttc atgtgaaa                         4718

SEQ ID NO: 4           moltype = DNA  length = 2216
FEATURE                Location/Qualifiers
source                 1..2216
                       mol_type = genomic DNA
                       organism = Rattus norvegicus
SEQUENCE: 4
tgcaagatgg gtgtctaccg catccgcgtc tccaccggag actccaagta cgcgggctcc  60
aacaacgagg tctacctgtg gttggttgga cagcatggag aggcatctct cgggaagctg  120
ctacgaccct gtcgggactc ggaagcagaa ttcaaagtgg atgtgtcagg ataccttggg  180
ccactgctgt tcgtaagagt gcagaaatgg cattatctca cggatgacgc ctggttctgc  240
aactggattt ctgtgaaggg ccccggagac caaggatcag agtacatgtt cccctgttac  300
cgatgggttc agggcagaag catcctgagc ctccctgagg gcactggctg caccgtggtt  360
gaagattctc aaggactgtt caggaaacat agggaagagg agcttgaaga gaggaggagt  420
ctgtacaggt ggggcaactg gaaggatggc tcaatcctga atgtggcggc ggccagtata  480
tctgacctcc ctgtagacca acgatttcga gaggacaaaa gaattgaatt tgaagcttca  540
caggttatag gggtaatgga tactgttgtc aactttccta taaacactgt gacctgctgg  600
aaaagcctag atgacttcaa ctgcgttttc aagagtggcc ataccaaaat ggctgagcgg  660
gttcgaaact cctggaagga agatgcgttc tttgggtacc aattcctcaa tggtgctaac  720
cccatggtgc tgaagcgctc tacttgtctt cctgcccgcc tggtattccc tccaggaatg  780
gagaagctac aggcccagct gaacaaggag ctccagaaag gcactctgtt tgaagcggat  840
ttcttccttc tggatgggat caaggccaat gtcatccttt gtagccagca gtacctggct  900
gcccctctcg tcatgctgaa gctgatgcct gatggacaac tcttgcccat agccatccag  960
cttgaacttc ccaaaactgg gtctactcca ccacctattt tcacgccctc ggatcccccca  1020
atggactggc tcctagccaa atgctgggtc cggagctccg acttacagct ccatgagctg  1080
caggctcatc ttctgagggg acacttgatg gctgaggtct ttgctgtggc caccatgagg  1140
tgcctgcctt ccgtgcaccc tgtttttaag cttctagttc ctcatctgct ttacaccatg  1200
gaaattaatg tccgggccag gagtgacctg atctcagaga gaggcttttt tgacaaggca  1260
atgagcacag gtgggggagg ccacctggat cttctcaagc aagctggagc ctttctgacc  1320
```

-continued

```
tattgctcat tgtgtccccc cgatgacttg gctgagcgag gactcttgga tatcgagact  1380
tgcttctatg ctaaagacgc cctgcgactc tggcagatca tgaatcggta cgtggtggga  1440
atgttcaatc tccactacaa gaccgacaaa gctgtgcaag acgactatga actgcagagc  1500
tggtgtcgag agatcactga cattggtctt caaggggccc aggacagagg cttccctacc  1560
tctcttcagt cccgggctca ggcttgctac ttcatcacca tgtgcatctt cacgtgcacc  1620
gcacagcact cttccgtcca tcttggccag ctggattggt tctactgggt tcctaatgca  1680
ccctgcacca tgcggctgcc accacccacc accaaggaag caacaatgga gaagctgatg  1740
gctacactgc ccaaccctaa tcagtctact ctccagataa atgtcgtttg gctcctgggc  1800
agacgccagg ctgttatggt gcccctgggc cagcattcag aggaacactt tccaaaccct  1860
gaggccaagg ctgtgctgaa gaagttcaga gaggaactgg ctgccttgga taaggaaatt  1920
gagattcgta ataagagctt ggacatacct tatgagtacc tgcggcccag catggtggaa  1980
aacagcgtgg ccatatgagc atccccagac tcctgctttg ttgtttagtt aagaccaccc  2040
aagtacatcc ctgtgcttga gtggtggcag tcctgccctc ccaagccccg ccctctgacc  2100
ctcaaagccc cacccccctgc ccatgtggga ccctcctcca agctgtccat tgtctgctgc  2160
aatgaataca ttttgctttg gatgcattaa aaaaaaaaaa aaaaaaaaaa aaaaaa      2216
```

```
SEQ ID NO: 5            moltype = DNA  length = 2105
FEATURE                 Location/Qualifiers
source                  1..2105
                        mol_type = genomic DNA
                        organism = Homo sapiens
SEQUENCE: 5
tccgggtttt gcggcggagc gggcgggctg cgcgtgcggc ggcttcaact gtcgcggtag  60
gcagcagcag gctgaaggga tcatggtgca gtacgagctg tgggccgcgc tgcctggcgc  120
ctccggggtc gccctggcct gctgcttcgt ggcggcggcc gtggccctgc gctggtccgg  180
gcgccggacg gcgcggggcg cggtggtccg ggcgcgacag aggcagcgag cgggcctgga  240
gaacatggac agggcggcgc agcgcttccg gctccagaac ccagacctgg actcagaggc  300
gctgctagcc ctgcccctgc ctcagctggt gcagaagtta cacagtagag agctggcccc  360
tgaggccgtg ctcttcacct atgtgggaaa ggcctgggaa gtgaacaaag ggaccaactg  420
tgtgacctcc tatctggctg actgtgagac tcagctgtct caggccccaa ggcagggcct  480
gctctatggc gtccctgtga gcctcaagga gtgcttcacc tacaagggcc aggactccac  540
gctgggcttg agcctgaatg aaggggtgcc ggcggagtgc gacagcgtag tggtgcatgt  600
gctgaagctg cagggtgccg tgcccttcgt gcacaccaat gttccacagt ccatgttcag  660
ctatgactgc agtaaccccc tctttggcca gaccgtgaac ccatggaagt cctccaaaag  720
cccagggggc tcctcagggg gtgaaggggc cctcatcggg tctggaggct ccccccctggg  780
cttaggcact gatatcggag gcagcatccg cttcccctcc tccttctgcg gcatctgcgg  840
cctcaagccc acagggaacc gcctcagcaa gagtggcctg aagggctgtg tctatggaca  900
ggaggcagtg cgtctctccg tgggccccat ggcccgggac gtggagagcc tggcactgtg  960
cctgcgagcc ctgctgtgcg aggacatgtt ccgcttggac cccactgtgc ctcccttgcc  1020
cttcagagaa gaggtctaca ccagctctca gcccctgcgt gtggggtact atgagactga  1080
caactatacc atgccctccc cggccatgag gcgggccgtg ctggagacca aacagagcct  1140
tgaggctgcg gggcacacgc tggttccctt cttgccaagc aacatacccc atgctctgga  1200
gaccctgtca acaggtgggc tcttcagtga tggtggccac accttcctac agaacttcaa  1260
aggtgatttc gtggacccct gcctggggga cctggtctca attctgaagc ttccccaatg  1320
gcttaaagga ctgctggcct tcctggtgaa gcctctgctg ccaaggctgt cagctttcct  1380
cagcaacatg aagtctcgtt cggctggaaa actctgggaa ctgcagcacg agatcgaggt  1440
gtaccgcaaa accgtgattg cccagtggag ggcgctggac ctggatgtgg tgctgacccc  1500
catgctggcc cctgctctgg acttgaatgc cccaggcagg gccacagggg ccgtcagcta  1560
cactatgctg tacaactgcc tggacttccc tgcaggggtg gtgcctgtca ccacggtgac  1620
tgctgaggac gaggcccaga tggaacatta caggggctac tttggggata tctgggacaa  1680
gatgctgcag aagggcatga agaagagtgt ggggctgccg gtggccgtgc agtgtgtggc  1740
tctgccctgg caagaagagt tgtgtctgcg gttcatgcgg gaggtggagc gactgatgac  1800
ccctgaaaag cagtcatcct gatggctctg gctccagagg acctgagact cacactctct  1860
gcagcccagc ctagtcaggg cacagctgcc ctgctgccac agcaaggaaa tgtcctgcat  1920
ggggcagagg cttccgtgtc ctctccccca accccctgca agaagcgccg actccctgag  1980
tctggacctc catccctgct ctggtcccct ctcttcgtcc tgatccctcc acccccatgt  2040
ggcagcccat gggtatgaca taggccaagg cccaactaac agtcaagaaa cagctaaaaa  2100
aaaaa                                                             2105
```

```
SEQ ID NO: 6            moltype = AA  length = 1531
FEATURE                 Location/Qualifiers
source                  1..1531
                        mol_type = protein
                        organism = Homo sapiens
SEQUENCE: 6
MALRGFCSAD GSDPLWDWNV TWNTSNPDFT KCFQNTVLVW VPCFYLWACF PFYFLYLSRH  60
DRGYIQMTPL NKTKTALGFL LWIVCWADLF YSFWERSRGI FLAPVFLVSP TLLGITMLLA  120
TFLIQLERRK GVQSSGIMLT FWLVALVCAL AILRSKIMTA LKEDAQVDLF RDITFYVYFS  180
LLLIQLVLSC FSDRSPLFSE TIHDPNPCPE SSASFLSRIT FWWITGLIVR GYRQPLEGSD  240
LWSLNKEDTS EQVVPVLVKN WKKECAKTRK QPVKVVYSSK DPAQPKESSK VDANEEVEAL  300
IVKSPQKEWN PSLFKVLYKT FGPYFLMSFF FKAIHDLMMF SGPQILKLLI KFVNDTKAPD  360
WQGYFYTVLL FVTACLQTLV LHQYFHICFV SGMRIKTAVI GAVYRKALVI TNSARKSSTV  420
GEIVNLMSVD AQRFMDLATY INMIWSAPLQ VILALYLLWL NLGPSVLAGV AVMVLMVPVN  480
AVMAMKTKTY QVAHMKSKDN RIKLMNEILN GIKVLKLYAW ELAFKDKVLA IRQEELKVLK  540
KSAYLSAVGT FTWVCTPFLV ALCTFAVYVT IDENNILDAQ TAFVSLALFN ILRFPLNILP  600
MVISSIVQAS VSLKRLRIFL SHEELEPDSI ERRPVKDGGG TNSITVRNAT FTWARSDPPT  660
LNGITFSIPE GALVAVVGQV GCGKSSLLSA LLAEMDKVEG HVAIKGSVAY VPQQAWIQND  720
SLRENILFGC QLEEPYYRSV IQACALLPDL EILPSGDRTE IGEKGVNLSG GQKQRVSLAR  780
AVYSNADIYL FDDPLSAVDA HVGKHIFENV IGPKGMLKNK TRILVTHSMS YLPQVDVIIV  840
```

-continued

```
MSGGKISEMG SYQELLARDG AFAEFLRTYA STEQEQDAEE NGVTGVSGPG KEAKQMENGM  900
LVTDSAGKQL QRQLSSSSSY SGDISRHHNS TAELQKAEAK KEETWKLMEA DKAQTGQVKL  960
SVYWDYMKAI GLFISFLSIF LFMCNHVSAL ASNYWLSLWT DDPIVNGTQE HTKVRLSVYG  1020
ALGISQGIAV FGYSMAVSIG GILASRCLHV DLLHSILRSP MSFFERTPSG NLVNRFSKEL  1080
DTVDSMIPEV IKMFMGSLFN VIGACIVILL ATPIAAIIIP PLGLIYFFVQ RFYVASSRQL  1140
KRLESVSRSP VYSHFNETLL GVSVIRAFEE QERFIHQSDL KVDENQKAYY PSIVANRWLA  1200
VRLECVGNCI VLFAALFAVI SRHSLSAGLV GLSVSYSLQV TTYLNWLVRM SSEMETNIVA  1260
VERLKEYSET EKEAPWQIQE TAPPSSWPQV GRVEFRNYCL RYREDLDFVL RHINVTINGG  1320
EKVGIVGRTG AGKSSLTLGL FRINESAEGE IIIDGINIAK IGLHDLRFKI TIIPQDPVLF  1380
SGSLRMNLDP FSQYSDEEVW TSLELAHLKD FVSALPDKLD HECAEGGENL SVGQRQLVCL  1440
ARALLRKTKI LVLDEATAAV DLETDDLIQS TIRTQFEDCT VLTIAHRLNT IMDYTRVIVL  1500
DKGEIQEYGA PSDLLQQRGL FYSMAKDAGL V                                1531

SEQ ID NO: 7           moltype = DNA  length = 21
FEATURE                Location/Qualifiers
misc_feature           1..21
                       note = Synthetic
source                 1..21
                       mol_type = other DNA
                       organism = synthetic construct
SEQUENCE: 7
tttcttggat tatgccgggt a                                           21

SEQ ID NO: 8           moltype = DNA  length = 22
FEATURE                Location/Qualifiers
misc_feature           1..22
                       note = Synthetic
source                 1..22
                       mol_type = other DNA
                       organism = synthetic construct
SEQUENCE: 8
gttggcaagc tttgacaaca ct                                          22

SEQ ID NO: 9           moltype = DNA  length = 19
FEATURE                Location/Qualifiers
misc_feature           1..19
                       note = Synthetic
source                 1..19
                       mol_type = other DNA
                       organism = synthetic construct
SEQUENCE: 9
aaacaccaaa gatgatatt                                              19

SEQ ID NO: 10          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 10
aacaccaata atattttc                                               18
```